(12) United States Patent
Ikegami et al.

(10) Patent No.: US 9,593,081 B2
(45) Date of Patent: Mar. 14, 2017

(54) 4-ALKYNYL IMIDAZOLE DERIVATIVE AND MEDICINE COMPRISING SAME AS ACTIVE INGREDIENT

(71) Applicant: KAKEN PHARMACEUTICAL CO., LTD., Tokyo (JP)

(72) Inventors: Satoru Ikegami, Kyoto (JP); Atsushi Watanabe, Kyoto (JP); Kimio Hirano, Kyoto (JP); Tadashi Ohyama, Kyoto (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/897,324

(22) PCT Filed: Jun. 12, 2014

(86) PCT No.: PCT/JP2014/065643
§ 371 (c)(1),
(2) Date: Dec. 10, 2015

(87) PCT Pub. No.: WO2014/200075
PCT Pub. Date: Dec. 18, 2014

(65) Prior Publication Data
US 2016/0130232 A1    May 12, 2016

(30) Foreign Application Priority Data

Jun. 12, 2013 (JP) ................................ 2013-123968

(51) Int. Cl.
*C07D 233/90* (2006.01)
*C07D 403/12* (2006.01)
*C07D 401/06* (2006.01)
*C07D 401/12* (2006.01)
*C07D 413/12* (2006.01)

(52) U.S. Cl.
CPC ......... *C07D 233/90* (2013.01); *C07D 401/06* (2013.01); *C07D 401/12* (2013.01); *C07D 403/12* (2013.01); *C07D 413/12* (2013.01)

(58) Field of Classification Search
CPC .................................................. C07D 233/90
See application file for complete search history.

(56) References Cited

U.S. PATENT DOCUMENTS

| 2006/0258728 A1 | 11/2006 | Tani et al. |
| 2011/0028463 A1 | 2/2011 | Nozawa et al. |
| 2011/0144153 A1 | 6/2011 | Nozawa et al. |

FOREIGN PATENT DOCUMENTS

| CN | 1551866 A | 12/2004 |
| JP | 2010-519260 A | 6/2010 |
| WO | 02060898 A1 | 8/2002 |
| WO | 2005/021508 A1 | 3/2005 |
| WO | 2005/105732 A1 | 11/2005 |
| WO | 2005/105733 A1 | 11/2005 |
| WO | 2007/121578 A1 | 11/2007 |
| WO | 2007/143825 A1 | 12/2007 |
| WO | 2008/017164 A1 | 2/2008 |
| WO | 2008/104055 A1 | 9/2008 |
| WO | 2009/005076 A1 | 1/2009 |
| WO | 2009/139373 A1 | 11/2009 |
| WO | 2010/019796 A1 | 2/2010 |
| WO | 2012/039972 A1 | 3/2012 |
| WO | 2012/076063 A1 | 6/2012 |
| WO | 2012/103071 A2 | 8/2012 |
| WO | 2013/004290 A1 | 1/2013 |

OTHER PUBLICATIONS

International Search Report dated Jul. 15, 2014 from the International Searching Authority in counterpart International Application No. PCT/JP2014/065643.

(Continued)

*Primary Examiner* — Laura L. Stockton
(74) *Attorney, Agent, or Firm* — Sughrue Mion, PLLC

(57) ABSTRACT

There are provided 4-alkynylimidazole derivatives represented by the following general formula (I) or pharmaceutically acceptable salts thereof; the derivatives have a superior EP4 receptor antagonistic action and are useful as pharmaceuticals for the treatment of diseases associated with the EP4 receptor, for example, as anti-inflammatory and/or analgesic drugs for inflammatory diseases and diseases that involve various kinds of pains, and further as pharmaceuticals for the treatment of immune diseases that result from inflammations as evoked by tissue destruction due to the activation of Th1 cells and/or Th17 cells:

[Formula 1]

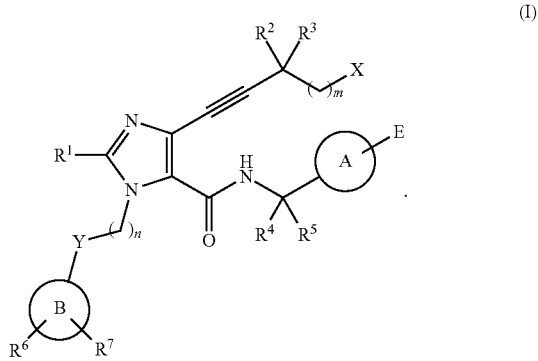

15 Claims, No Drawings

(56) References Cited

OTHER PUBLICATIONS

Blouin et al., The Discovery of 4-{1-[({2,5 Dimethyl-4-[4-(triflouromethyl)benzyl]-3-thienyl}carbonyl)amino]cyclopropyl}benzoic Acid (MK-2894), A Potent and Selective Prostaglandin E2 Subtype 4 Receptor Antagonist, Journal of Medicinal Chemistry, 2010, vol. 53, pp. 2227-2238.
Colucci et al., "Discovery of 4-{I-[({I-[4-(trifluoromethyl)benzyl]-1H-indol-7-yl}carbonyl)amino]cyclopropyl}benzoic acid (MF-766), a highly potent and selective EP4 antagonist for treating inflammatory pain," Bioorganic & Medicinal Chemistry Letters, 2010, vol. 20, pp. 3760-3763.
Boyd et al., "A novel series of potent and selective EP4 receptor ligands: Facile modulation of agonism and antagonism," Bioorganic & Medicinal Chemistry Letters, 2011, vol. 21, pp. 484-487.
Flesch et al., "Novel prostaglandin receptor modulators—Part II: EP receptor modulators; a patent review (2002-2012)," Expert Opinion on Therapeutic Patents, Taylor & Francis Group, 2013, vol. 23, pp. 233-267 (18 pages total.).
Communication dated Sep. 21, 2016, issued by the European Patent Office in corresponding European Application No. 14811154.5.
Communication dated Dec. 22, 2016, from the State Intellectual Property Office of People's Republic of China in corresponding Chinese Application No. 201480044505.6.

4-ALKYNYL IMIDAZOLE DERIVATIVE AND MEDICINE COMPRISING SAME AS ACTIVE INGREDIENT

CROSS REFERENCE TO RELATED APPLICATIONS

This is a National Stage of International Application No. PCT/JP2014/065643 filed Jun. 12, 2014, claiming priority based on Japanese Patent Application No. 2013-123968 filed Jun. 12, 2013.

TECHNICAL FIELD

The present invention relates to novel 4-alkynylimidazole derivatives and pharmaceutical comprising them as an active ingredient. More particularly, the present invention relates to novel compounds having an antagonistic action on the prostaglandin E2 (PGE2) receptor EP4.

BACKGROUND ART

Prostaglandins (PGs) are a series of physiologically active substances having the prostanoic acid skeleton. Being a member of this class, prostaglandin E2 (PGE2) is generated from arachidonic acid by a four-stage synthesis reaction called the arachidonic acid cascade and is known to have a variety of actions including a pain triggering action, inflammatory response, a cell protecting action, uterine contraction, peristaltic promotion of the digestive canal, antihypnotic action, a gastric acid secretion suppressing action, a hypotensive action, an angiogenic action, a diuretic action, etc. Conventionally, as therapeutics for diseases associated with such PGs, non-steroidal anti-inflammatory drugs (NSAIDs) are extensively used that suppress prostaglandin production by means of inhibiting cyclooxygenase (COX) which is one of the synthases participating in the arachidonic acid cascade; NSAIDs, however, present the problem that on account of their inhibiting the upstream stage of the arachidonic acid cascade, various side-effects including gastrointestinal disorders occur as complications. In view of such side-effects, drugs are desired that inhibit the binding of PGE2 to PGE2 receptors.

The PGE2 receptors exist in four subtypes, EP1, EP2, EP3 and EP4, which are distributed widely among a variety of tissues.

The actions of PGE2 as mediated by the EP4 receptor are involved in inflammatory responses (including immune inflammatory response), relaxation of smooth muscle, pain triggering, differentiation of lymphocytes, enlargement or proliferation of mesangial cells, secretion of gastrointestinal mucus, for example. Hence, EP4 receptor antagonistic drugs are considered to be promising as anti-inflammatory and/or analgesic drugs for diseases associated with the receptor EP4-mediated PGE2 actions (such as, for example, inflammatory diseases and diseases that involve various kinds of pain). Further, it has recently been reported that the action of PGE2 mediated by the receptor EP4 on the surfaces of dendritic cells or T cells causes activation of Th1 cells or Th17 cells; the activated Th1 or Th17 cells cause tissue destruction and evoke inflammation, eventually triggering multiple sclerosis and various other immune diseases; hence, the EP4 receptor antagonistic drugs are also attracting researchers' attention as therapeutics for such immune diseases (Non-Patent Documents 1 and 2). In this regard, it has been verified that a plurality of EP4 receptor antagonists having different skeletons are actually effective in EAE (experimental autoimmune encephalomyelitis) models which are animal models for immune diseases typified by multiple sclerosis (Non-Patent Documents 2 and 3).

Thus, compounds that are antagonistic against the EP4 receptor-mediated actions of PGE2 hold promise as drugs for the treatment of diseases involving various inflammations including acute and/or chronic as well as immune inflammations, and various studies have heretofore been conducted on EP4 receptor antagonistic drugs.

EP4 receptor antagonistic drugs so far known include, for example, compounds represented by the following formula (Patent Documents 1, 2 and 3):

[Formula 1]

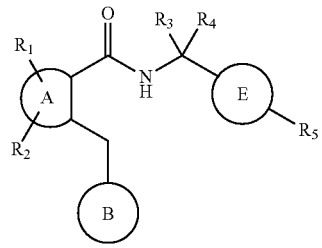

(wherein ring A represents phenyl or pyridyl; for details, see the documents cited above).

As EP4 receptor antagonists, compounds represented by the following formula are also known (Patent Document 4):

[Formula 2]

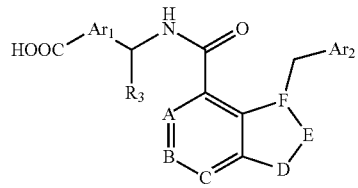

(for the symbols in the formula, see the document cited above).

As EP4 receptor antagonists, compounds represented by the following formula are also known (Patent Document 5):

[Formula 3]

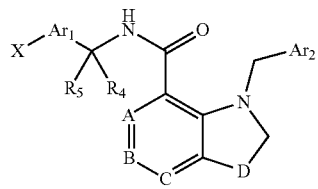

(for the symbols in the formula, see the document cited above).

As EP4 receptor antagonists, compounds represented by the following formula are also known (Patent Document 6):

[Formula 4]

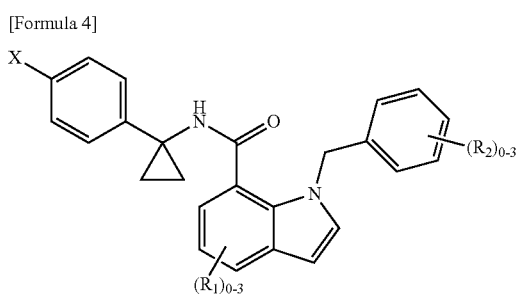

(for the symbols in the formula, see the document cited above).

As EP4 receptor antagonists, compounds represented by the following formula are also known (Patent Document 7):

[Formula 5]

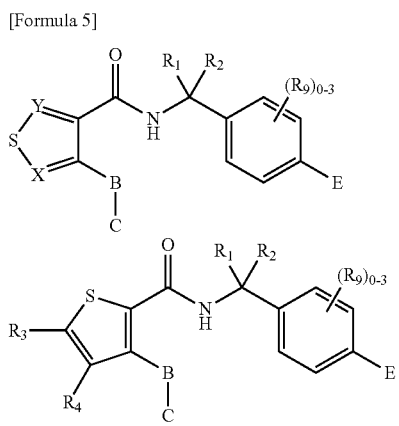

(for the symbols in the formulae, see the document cited above).

As EP4 receptor antagonists, compounds represented by the following formula are also known (Patent Document 8):

[Formula 6]

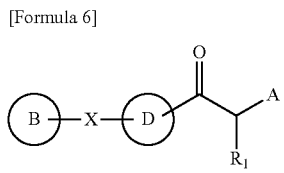

(for the symbols in the formula, see the document cited above).

As EP4 receptor antagonists, compounds represented by the following formula are also known (Patent Document 9):

[Formula 7]

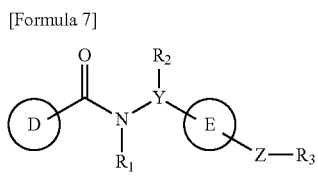

(wherein ring D is a group represented by:

[Formula 8]

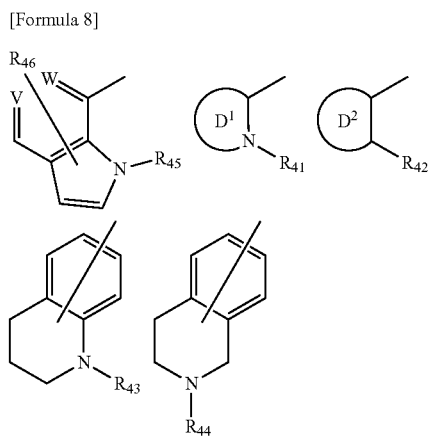

for details see the document cited above).

As EP4 receptor antagonists, compounds represented by the following formula are also known (Patent Document 10):

[Formula 9]

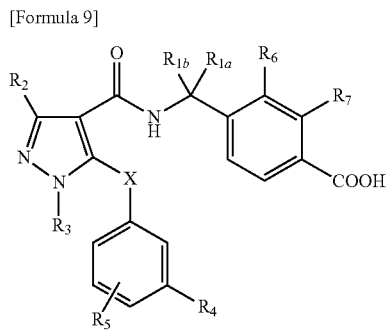

(for the symbols in the formula, see the document cited above).

As EP4 receptor antagonists, compounds represented by the following formula are also known (Patent Document 11):

[Formula 10]

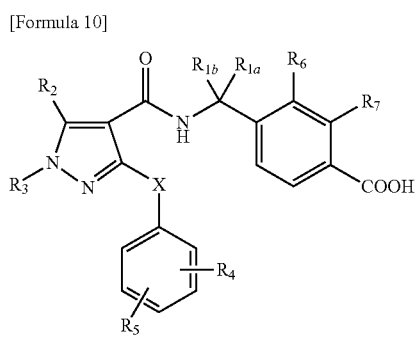

(for the symbols in the formula, see the document cited above).

Neither of these prior art documents disclose or suggest 4-alkynylimidazole derivatives.

CITATION LIST

Patent Literature

Patent Document 1: WO2005/021508
Patent Document 2: WO2005/105732
Patent Document 3: WO2005/105733
Patent Document 4: WO2007/121578
Patent Document 5: WO2007/143825
Patent Document 6: WO2008/104055
Patent Document 7: WO2008/017164
Patent Document 8: WO2009/005076
Patent Document 9: WO2009/139373
Patent Document 10: WO2012/039972
Patent Document 11: WO2012/103071

Non-Patent Literature

Non-Patent Document 1: Sakata D, et al, J Pharmacol Sci, 112, 1-5, 2010
Non-Patent Document 2: Yao C, et al, Nature Medicine, 15, 633-640, 2009
Non-Patent Document 3: Kenzo Muramoto, "The regulation of immune response by a novel synthetic compound E6201 and EP4 antagonists and their pharmacological effects" in the Repository of Kumamoto University, Issue date: 2011 Jan. 4, (http://hdl.handle.net/2298/22144)

SUMMARY OF INVENTION

Technical Problem

One object the present invention is to provide novel compounds that have an EP4 receptor antagonistic action and which are useful in the treatment of various diseases that originate from the EP4 receptor-mediated actions of PGE2, or salts of such compounds. Another object of the present invention is to provide pharmaceuticals that comprise these novel compounds or salts thereof as an active ingredient.

Solution to Problem

The present inventors conducted intensive studies with a view to solving the aforementioned problems and found, as a result, that compounds represented by the following general formula (I) which have an alkynyl at the 4-position of imidazole have a superior EP4 receptor antagonistic action; the present invention has been accomplished on the basis of this finding.

The present invention is described below in detail. In the following description, the 4-alkynylimidazole derivatives represented by the general formula (I) or pharmacologically acceptable salts thereof are collectively referred to as the "4-alkynylimidazole derivatives of the present invention."

Embodiments of the present invention are shown below.

(1) A 4-alkynylimidazole derivative represented by the general formula (I) or a pharmaceutically acceptable salt thereof:

[Formula 11]

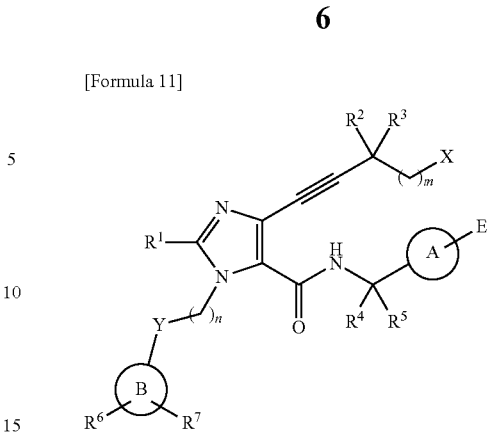

[wherein ring A is an optionally substituted cycloalkyl, an optionally substituted aryl or an optionally substituted heteroaryl;
ring B is cycloalkyl, aryl or heteroaryl;
m is an integer of any one of 0~2;
n is an integer of any one of 1~3;
$R^1$ is a hydrogen atom, a $C_1$~$C_4$ alkyl group, a $C_1$~$C_4$ alkoxy group, a halogen atom, or a $C_1$~$C_4$ haloalkyl group;
$R^2$ and $R^3$ are each independently a hydrogen atom, a halogen atom or a $C_1$~$C_4$ alkyl group or may, taken together with the carbon atom to which $R^2$ and $R^3$ are adjacent, form a $C_3$~$C_6$ carbon ring;
$R^4$ and $R^5$ are each independently a hydrogen atom or a $C_1$~$C_4$ alkyl group or may, taken together with the carbon atom to which $R^4$ and $R^5$ are adjacent, form a $C_3$~$C_6$ carbon ring,
and $R^6$ and $R^7$ are each independently a hydrogen atom, a $C_1$~$C_4$ alkyl group, a $C_1$~$C_4$ alkoxy group, a $C_1$~$C_4$ hydroxyalkyl group, a carboxyl group, a cyano group, a halogen atom, a $C_1$~$C_4$ haloalkyl group, or a $C_1$~$C_4$ haloalkoxy group;
X is —$OR^8$, —$NR^9R^{10}$ or a halogen atom;
$R^8$ is a hydrogen atom, a $C_1$~$C_4$ alkyl group or a $C_1$~$C_4$ haloalkyl group;
$R^9$ and $R^{10}$ are each independently a hydrogen atom or a $C_1$~$C_4$ alkyl group or may, taken together with the nitrogen atom to which $R^9$ and $R^{10}$ are adjacent, form a nitrogen-containing heterocycle, Y is a single bond, an oxygen atom or a sulfur atom; and
E is —$CO_2H$, —$CO_2P$ or a bioisostere of a carboxyl group; —$CO_2P$ is pharmaceutically acceptable ester prodrug].

(2) The 4-alkynylimidazole derivative recited in (1) or a pharmaceutically acceptable salt thereof, wherein in the foregoing general formula (I), X is —$OR^8$ ($R^8$ is as defined in (1)) and m is 0.

(3) The 4-alkynylimidazole derivative recited in (1) or (2) or a pharmaceutically acceptable salt thereof, wherein in the foregoing general formula (I), $R^2$ and $R^3$ are both a methyl group.

(4) The 4-alkynylimidazole derivative recited in any one of (1)~(3) or a pharmaceutically acceptable salt thereof, wherein in the foregoing general formula (I), $R^1$ is a methyl group, an ethyl group, a cyclopropyl group, a chlorine atom, a difluoromethyl group, or a trifluoromethyl group.

(5) The 4-alkynylimidazole derivative recited in (4) or a pharmaceutically acceptable salt thereof, wherein in the foregoing general formula (I), $R^1$ is a chlorine atom.

(6) The 4-alkynylimidazole derivative recited in any one of (1)~(5) or a pharmaceutically acceptable salt thereof, wherein in the foregoing formula (I), ring A is a cyclohexyl substituted by E at the 4-position or phenyl substituted by E at the 4-position (where E is as defined in (1)).

(7) The 4-alkynylimidazole derivative recited in any one of (1)~(6) or a pharmaceutically acceptable salt thereof, wherein in the foregoing formula (I), E is —CO$_2$H or tetrazolyl.

(8) The 4-alkynylimidazole derivative recited in any one of (1)~(7) or a pharmaceutically acceptable salt thereof, wherein in the foregoing formula (I), ring B is phenyl, n is 1, and Y is a single bond.

(9) The 4-alkynylimidazole derivative recited in (8) or a pharmaceutically acceptable salt thereof, wherein in the foregoing formula (I), ring B is phenyl substituted by R$^6$ at the 4-position, R$^7$ is a hydrogen atom, and R$^6$ is any one of a C$_1$~C$_f$ alkyl group, a C$_1$~C$_4$ alkoxy group, a cyano group, a halogen atom, a C$_1$~C$_4$ haloalkyl group, and a C$_1$~C$_4$ haloalkoxy group.

(10) The 4-alkynylimidazole derivative recited in (1) or a pharmaceutically acceptable salt thereof, wherein the compound represented by the foregoing formula (I) is any one of:

[Formula 12]

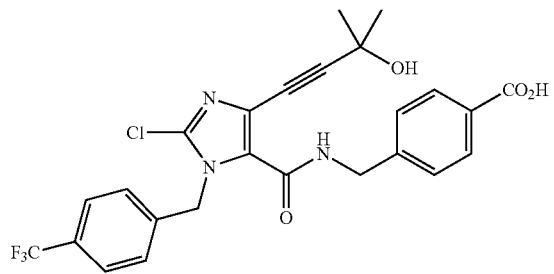 [SMILES: CC(C)(O)C#Cc1nc(Cl)n(Cc2ccc(C(F)(F)F)cc2)c1C(=O)NCc1ccc(C(=O)O)cc1]

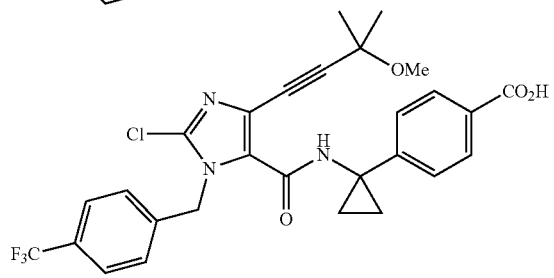

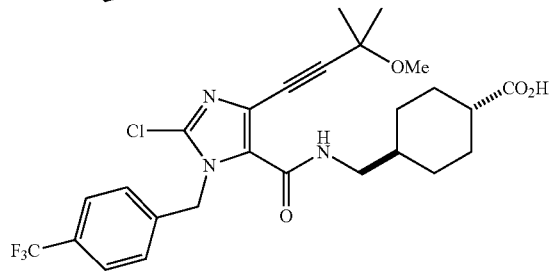

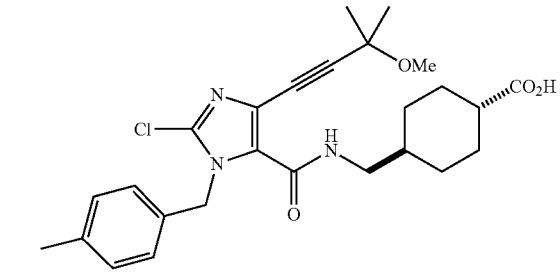

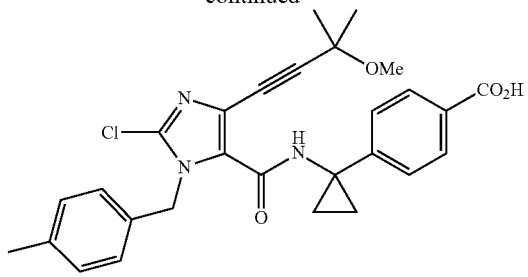

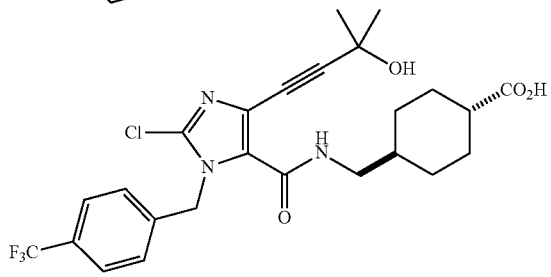

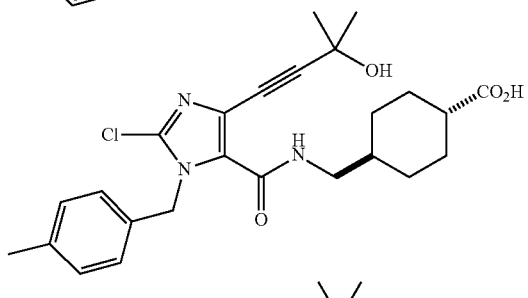

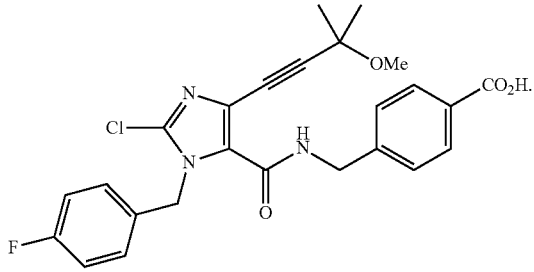 [SMILES: COC(C)(C)C#Cc1nc(Cl)n(Cc2ccc(C)cc2)c1C(=O)NC1(c2ccc(C(=O)O)cc2)CC1]

(11) The 4-alkynylimidazole derivative recited in (1) or a pharmaceutically acceptable salt thereof, wherein the compound represented by the foregoing formula (I) is:

[Formula 13]

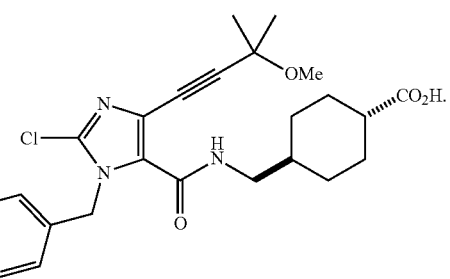

(12) A pharmaceutical comprising the 4-alkynylimidazole derivative recited in any one of (1)~(11) or a pharmaceutically acceptable salt thereof as an active ingredient.

(13) An EP4 receptor antagonist comprising the 4-alkynylimidazole derivative recited in any one of (1)~(11) or a pharmaceutically acceptable salt thereof.

(14) The pharmaceutical recited in (12) which is used in the treatment of a disease associated with an EP4 receptor-mediated action of PGE2.
(15) The pharmaceutical recited in (14), wherein the disease is an inflammatory disease or an inflammatory pain.
(16) The pharmaceutical recited in (14) or (15), wherein the disease is at least one disease selected from the group consisting of arthritic pain, articular rheumatism, osteoarthritis, lumbago, scapulohumeral periarthritis, cervico-omobrachial syndrome, tendonitis, and thecitis.
(17) The pharmaceutical recited in any one of (14)~(16), wherein the treatment is anti-inflammation and/or pain relieving.
(18) The pharmaceutical recited in (14), wherein the disease is an immune disease in which Th1 cells and/or Th17 cells are implicated.
(19) The pharmaceutical recited in (14) or (18), wherein the disease is at least one disease selected from the group consisting of multiple sclerosis, ulcerative colitis, Crohn's disease, atopic dermatitis, psoriasis, and contact dermatitis.
(20) The pharmaceutical recited in (19), wherein the disease is multiple sclerosis.

Advantageous Effects of Invention

The 4-alkynylimidazole derivatives of the present invention have a superior EP4 receptor antagonistic action as described specifically in the Test Examples to be given later. Hence, the 4-alkynylimidazole derivatives of the present invention are useful as drugs for the treatment of diseases mediated by the EP4 receptor, for example, as anti-inflammatory and/or analgesic drugs for inflammatory diseases or diseases that involve various kinds of pains.

DESCRIPTION OF EMBODIMENTS

Hereinafter, the 4-alkynylimidazole derivatives of the present invention are described in detail. The following description of terminology is occasionally based on representative embodiments and specific examples of the present invention which, however, is by no means limited to those embodiments and specific examples. It should also be noted that the numerical ranges delineated herein using the symbol "~" mean that the values put before and after "~" are included as the lower and upper limits, respectively.

4-Alkynylimidazole Derivatives of the Present Invention

To begin with, the individual substituents in the foregoing general formula (I) are explained. The symbol "$C_1$~$C_4$" used in the explanation of each substituent means that the number of carbon atoms is within the range of 1~4.

The "$C_1$~$C_4$ alkyl group" means a linear, branched or cyclic $C_1$~$C_4$ alkyl group and specific examples include a methyl group, an ethyl group, a n-propyl group, an isopropyl group, a cyclopropyl group, a n-butyl group, an isobutyl group, a tert-butyl group, a sec-butyl group, a cyclobutyl group, a cyclopropylmethyl group, etc.

The "$C_1$~$C_4$ hydroxyalkyl group" is such an alkyl group that one or more of the hydrogen atoms in the foregoing "$C_1$~$C_4$ alkyl group" are replaced by a hydroxyl group and specific examples include a hydroxymethyl group, a hydroxyethyl group, etc.

The "$C_1$~$C_4$ haloalkyl group" is such an alkyl group that one or more of the hydrogen atoms in the foregoing "$C_1$~$C_4$ alkyl group" are replaced by a halogen atom or halogen atoms and specific examples include a monofluoromethyl group, a difluoromethyl group, a trifluoromethyl group, etc.

The "halogen atom" means a fluorine atom, a chlorine atom, a bromine atom, or an iodine atom.

The "$C_1$~$C_4$ alkoxy group" means an alkoxy group the alkyl moiety of which has the same meaning as defined for the foregoing "$C_1$~$C_4$ alkyl group" and may be exemplified by a methoxy group, an ethoxy group, a n-propoxy group, an isopropoxy group, a n-butoxy group, an isobutoxy group, a tert-butoxy group, a sec-butoxy group, a cyclopropylmethyloxy group, etc.

The "$C_1$~$C_4$ haloalkoxy group" means a haloalkoxy group the haloalkyl moiety of which has the same meaning as defined for the foregoing "$C_1$~$C_4$ haloalkyl group" and may be exemplified by a difluoromethoxy group, a trifluoromethoxy group, etc.

The "cycloalkyl" of the "optionally substituted cycloalkyl" as ring A and the "cycloalkyl" as ring B refer to a cyclic saturated hydrocarbon ring, preferably a $C_4$~$C_8$ cyclic saturated hydrocarbon ring, and may be exemplified by cyclopentyl, cyclohexyl, etc. The cycloalkyl of the "optionally substituted cycloalkyl" as ring A is preferably cyclohexyl, in which case the substituent E preferably substitutes at the 4-position and its configuration may be trans or cis, with trans configuration being particularly preferred.

The term "optionally substituted" in the foregoing "optionally substituted cycloalkyl" means that aside from the substituent E, the cycloalkyl may be substituted by substituents including a hydroxyl group, a halogen atom, a cyano group, a trifluoromethyl group, a $C_1$~$C_4$ alkyl group, a $C_1$~$C_4$ alkoxy group, a carboxyl group, etc. At least one of these substituents can substitute at all possible positions. If a plurality of substituents substitute, they may be the same or different. Here, the terms "a halogen atom", "a $C_1$~$C_4$ alkyl group" and "a $C_1$~$C_4$ alkoxy group" have the same meanings as defined above.

The "aryl" of the "optionally substituted aryl" as ring A and the "aryl" as ring B refer to an aromatic hydrocarbon ring, preferably a $C_6$~$C_{10}$ aromatic hydrocarbon ring, and may be exemplified by phenyl, naphthyl, etc. Phenyl is more preferred.

The term "optionally substituted" in the foregoing "optionally substituted aryl" means that aside from the substituent E, the aryl may be substituted by substituents including a hydroxyl group, a halogen atom, a cyano group, a trifluoromethyl group, a $C_1$~$C_4$ alkyl group, a $C_1$~$C_4$ alkoxy group, a carboxyl group, etc. At least one of these substituents can substitute at all possible positions. If a plurality of substituents substitute, they may be the same or different. Here, the terms "a halogen atom", "a $C_1$~$C_4$ alkyl group" and "a $C_1$~$C_4$ alkoxy group" have the same meanings as defined above.

The "heteroaryl" of the "optionally substituted heteroaryl" as ring A and the "heteroaryl" as ring B represent a 5~8-membered monocyclic unsaturated hetero ring containing 1~4 hetero atoms, as ring constituting atoms, that are selected from among an oxygen atom, a sulfur atom, and a nitrogen atom, or a bicyclic unsaturated hetero ring which is formed from the foregoing monocyclic unsaturated hetero ring fused to a benzene ring, for example. Here, the unsaturated hetero ring refers to a hetero ring having at least one unsaturated bond in the ring. Specific examples of such heteroaryl include pyrrolyl, pyrazolyl, imidazolyl, pyridyl, dihydropyridyl, pyridazinyl, pyrimidinyl, pyrazinyl, thiazolyl, isothiazolyl, thidiazolyl, oxazolyl, isoxazolyl, oxadiazolyl, thienyl, indolyl, isoindolyl, benzimidazolyl, quinolinyl, tetrahydroquinolinyl, isoquinolinyl, imidazopyridyl, quinoxalinyl, benzopyrimidinyl, quinazolinyl, benzothiazolyl, benzoxazolyl, etc; preferred among these are pyridyl, thienyl, and indolyl.

The term "optionally substituted" in the foregoing "optionally substituted heteroaryl" means that aside from the substituent E, the heteroaryl may be substituted by substituents including a hydroxyl group, a halogen atom, a cyano group, a trifluoromethyl group, a $C_1$~$C_4$ alkyl group, a $C_1$~$C_4$ alkoxy group, a carboxyl group, etc. At least one of these substituents can substitute at all possible positions. If a plurality of substituents substitute, they may be the same or different. Here, the terms "a halogen atom", "a $C_1$~$C_4$ alkyl group" and "a $C_1$~$C_4$ alkoxy group" have the same meanings as defined above.

The "$C_3$~$C_6$ carbon ring" formed by $R^4$ and $R^5$ taken together with the carbon atom to which they are adjacent means a $C_3$~$C_6$ cyclic saturated hydrocarbon ring and specific examples include a cyclopropane ring, a cyclobutane ring, a cyclopentane ring, and a cyclohexane ring.

The "nitrogen-containing hetero ring" formed by $R^9$ and $R^{10}$ taken together with the nitrogen atom to which they are adjacent means a 3~8-membered monocyclic saturated hetero ring containing at least one nitrogen atom as a ring constituting atom and specific examples include an azetidine ring, a pyrrolidine ring, a piperidine ring, etc.

The term "a bioisostere of a carboxyl group" means an atom or an atomic group having equivalent biological properties to the carboxyl group, which has an electronic or steric configuration comparable to —$CO_2H$ and which is capable of releasing acidic protons in the same way. Examples include hydroxamic acid (—CO—NH—OH), sulfonamide (—NH—$SO_2$—$C_1$~$C_6$ alkyl), acylcyanamide (—CO—NH—CN), acylsulfonamide (—CO—NH—$SO_2$—$C_1$~$C_6$ alkyl, —$SO_2$—NH—CO—$C_1$~$C_6$ alkyl), or tetrazolyl, oxadiazolonyl, oxadiazolthionyl, oxathiadiazolyl, thiadiazolonyl, triazolthionyl, hydroxyisoxazolyl, etc., and preferred is tetrazolyl or oxadiazolonyl.

In the case where asymmetric carbon is present in the compounds represented by the general formula (I), racemates thereof, diastereoisomers thereof, and individual optically active forms thereof are all encompassed by the present invention.

In the case where the compounds represented by the general formula (I) form hydrates or solvates, these are also encompassed by the present invention.

Pharmaceutically acceptable salts of the 4-alkynylimidazole derivatives represented by the general formula (I) are not particularly limited as long as they are pharmaceutically acceptable and they include, for example, salts with inorganic bases, salts with organic bases, salts with organic acids, salts with inorganic acids, and salts with amino acids. Exemplary salts with inorganic bases include alkali metal salts and alkaline earth metal salts, etc. such as lithium salt, sodium salt, potassium salt, calcium salt, magnesium salt, etc. Exemplary salts with organic bases include triethylamine salt, pyridine salt, ethanolamine salt, cyclohexylamine salt, dicyclohexylamine salt, dibenzylethanolamine salt, etc. Exemplary salts with organic acids include formate, acetate, tartrate, maleate, succinate, lactate, malate, ascorbate, oxalate, glycolate, phenylacetate, methanesulfonate, benzenesulfonate, etc. Exemplary salts with inorganic acids include hydrochloride, hydrobromide, phosphate, sulfamate, nitrate, etc. And exemplary salts with amino acids include glycine salt, alanine salt, arginine salt, glutamate, aspartate, etc.

Among the 4-alkynylimidazole derivatives of the present invention, those in which substituent E in the foregoing general formula (I) is —$CO_2P$ serve as pharmacologically acceptable, esterified carboxylic acid prodrugs (which are hereinafter referred to as "ester prodrugs"). Here the pharmacologically acceptable ester prodrugs refer to those which, when hydrolyzed in vivo, release an alcohol in free form that is permissible with the dose of their administration. Examples of the pharmacologically acceptable ester prodrugs for the 4-alkynylimidazole derivatives of the present invention include, but are not limited to, ester prodrugs based on alkyl esters such as ethyl ester, and double esters such as proxetil ester, medoxomil ester, etc.

Preferred embodiments of the 4-alkynylimidazole derivatives of the present invention are described below in the general formula (I).

A preferred example of ring A is an optionally substituted cycloalkyl or an optionally substituted phenyl, with cyclohexyl or phenyl being more preferred.

A preferred example of the moiety depicted below:

[Formula 14]

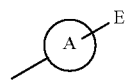

is cyclohexyl substituted by E at the 4-position or phenyl substituted by E at the 4-position. Here E is as defined above and, more preferably, —$CO_2H$ or tetrazolyl.

A preferred example of $R^1$ is a methyl group, an ethyl group, a cyclopropyl group, a chlorine atom, a difluoromethyl group or a trifluoromethyl group, with a chlorine atom being more preferred.

A preferred example of ring B is phenyl.

A preferred example of the moiety depicted below:

[Formula 15]

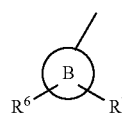

is phenyl substituted by $R^6$ at the 4-position, with $R^7$ being a hydrogen atom, in which case $R^6$ is any one of a $C_1$~$C_4$ alkyl group, a $C_1$~$C_4$ alkoxy group, a cyano group, a halogen atom, a $C_1$~$C_4$ haloalkyl group and a $C_1$~$C_4$ haloalkoxy group.

And n is preferably 1, with Y being preferably a single bond.

A preferred embodiment of the following moiety is as defined below:

[Formula 16]

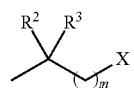

X is preferably —$OR^8$ ($R^8$ is as defined above). $R^8$ is preferably a hydrogen atom or a methyl group, more preferably, a methyl group.

A preferred case for $R^2$ and $R^3$ is where they are both a $C_1$~$C_4$ alkyl group or where $R^2$ and $R^3$, when taken together with the carbon atom to which they are adjacent, form a $C_3$~$C_6$ carbon ring, and more preferably, they are both a methyl group.

And m is preferably zero.

Methods for Producing the 4-Alkynylimidazole Derivatives of the Present Invention While the compounds represented by the foregoing general formula (I) can be produced by various methods, exemplary production methods are described below.

Specific examples of the "protective group" to be used in the following production methods include a tert-butyl group, a benzyl group, an o-methylbenzyl group, a p-nitrobenzyl group, a p-methoxybenzyl group, an o-chlorobenzyl group, a 2,4-dichlorobenzyl group, a p-bromobenzyl group, an allyl group, a tert-butoxycarbonyl group, a benzyloxycarbonyl group, an o-methylbenzyloxycarbonyl group, a p-nitrobenzyloxycarbonyl group, a p-methoxybenzyloxycarbonyl group, an o-chlorobenzyloxycarbonyl group, a 2,4-dichlorobenzyloxycarbonyl group, a p-bromobenzyloxycarbonyl group, an allyloxycarbonyl group, a tert-butyldimethylsilyl group, a tert-butyldiphenylsilyl group, a triethylsilyl group, a trimethylsilyl group, a triisopropylsilyl group, a methoxymethyl group, a tetrahydropyranyl group, protecting groups for the carbonyl group (e.g. protective groups based on ethanediol, propanediol, mercaptoethanol, mercaptopropanol, ethanedithiol, propanedithiol, etc.) and so forth.

Among the compounds represented by the general formula (I), compounds (I-1) in which substituent E is —$CO_2H$ may be produced by the method represented by the following Reaction Scheme 1 (step 1 to step 7).

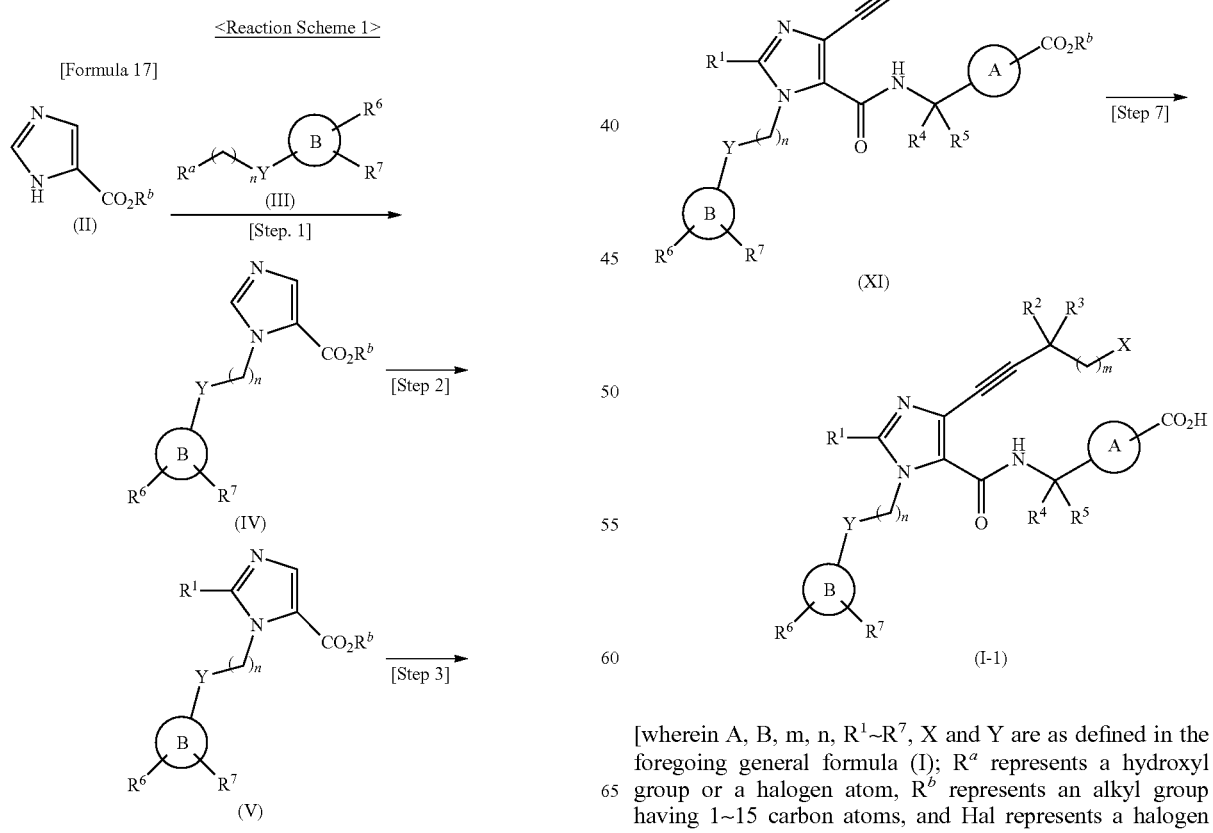

[wherein A, B, m, n, $R^1$~$R^7$, X and Y are as defined in the foregoing general formula (I); $R^a$ represents a hydroxyl group or a halogen atom, $R^b$ represents an alkyl group having 1~15 carbon atoms, and Hal represents a halogen atom.]

(Step 1)

A 1H-imidazole-5-carboxylic acid ester derivative represented by the general formula (II) and an alcohol represented by the general formula (III) ($R^a$ is a hydroxyl group) were acted upon by an azodicarboxylic acid ester derivative such as ethyl azodicarboxylate or diisopropyl azodicarboxylate and a phosphine derivative such as triphenylphosphine or tri-n-butylphosphine in a suitable neutral solvent (e.g. tetrahydrofuran, toluene or a solvent mixture thereof), whereby a corresponding compound represented by the general formula (IV) can be produced. In the case of using a halide represented by the general formula (III) ($R^a$ is a halogen atom), the compound represented by the general formula (II) and a base are acted upon the foregoing halide, whereby a corresponding compound represented by the general formula (IV) can be produced. Examples of the foregoing base include but are not limited to: alkali metal hydroxides such as lithium hydroxide, sodium hydroxide, potassium hydroxide, etc.; alkaline earth metal hydroxides such as magnesium hydroxide, calcium hydroxide, etc.; alkali metal carbonates such as sodium carbonate, potassium carbonate, sodium hydrogencarbonate, potassium hydrogencarbonate, etc.; metal hydrides such as sodium hydride, potassium hydride, etc.; and organic bases such as triethylamine, diisopropylethylamine, etc. The solvents that can be used are not particularly limited if they are inert solvents and they include, for example: aromatic hydrocarbons such as benzene, toluene, xylene, etc.; halogenated hydrocarbons such as dichloromethane, chloroform, 1,2-dichloroethane, etc.; nitriles such as acetonitrile, propionitrile, etc.; ketones such as acetone, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc. The reaction temperature is not particularly limited and may preferably be in the range of 0° C.~60° C. The reaction time is preferably in the range of 1 hr~24 hr.

(Step 2)

Onto the 2-position of the imidazole ring in the compound represented by the general formula (IV), a chlorine atom, a bromine atom or an iodine atom can be introduced by a method well known to a person having ordinary skill in the art, whereupon a corresponding compound represented by the general formula (V) can be produced. For example, the compound represented by the general formula (IV) can be converted to a chloride represented by the general formula (V) by acting on N-chlorosuccinimide in N,N-dimethylformamide. The solvents that can be used are not particularly limited if they are inert solvents and they include, for example: aromatic hydrocarbons such as benzene, toluene, xylene, etc.; halogenated hydrocarbons such as dichloromethane, chloroform, 1,2-dichloroethane, etc.; nitriles such as acetonitrile, propionitrile, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc. The reaction temperature is not particularly limited and may preferably be in the range of room temperature (RT)~80° C. The reaction time is preferably in the range of 1 hr~24 hr.

The compound represented by the general formula (V) as obtained in this step 2 may be reacted with various organic typical metal compounds which are well-known to a person having ordinary skill in the art (e.g. alkylboronic acid derivatives) or compounds having a substitutable hydrogen atom (e.g. methanol) in the presence of a base either alone or in combination with a palladium catalyst, whereupon the halogen substituent that has been introduced into $R^1$ can be converted to a $C_1$~$C_4$ alkyl group, a $C_1$~$C_4$ alkoxy group, a monofluoromethyl group, a difluoromethyl group or a trifluoromethyl group. This reaction may be performed after the end of step 2 or it may be performed as appropriate after a subsequent step as long as it does not affect the subsequent step. For example, the compound represented by the general formula (V) may be reacted with an alkylboronic acid derivative such as cyclopropylboronic acid pinacol ester in a solvent mixture of 1,4-dioxane and water in the presence of a palladium catalyst such as tetrakis(triphenylphosphine) palladium and a base such as cesium carbonate, whereupon the halogen substituent that has been introduced into $R^1$ can be converted to a cyclopropyl group. Examples of the solvent that can be used here include but are not limited to: aromatic hydrocarbons such as benzene, toluene, xylene, etc.; halogenated hydrocarbons such as dichloromethane, chloroform, 1,2-dichloroethane, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc.; and solvent mixtures thereof. Exemplary bases include inorganic bases such as sodium carbonate, potassium carbonate, sodium hydroxide, cesium carbonate, etc. Exemplary palladium catalysts include tetrakis(triphenylphosphine)palladium, dichlorobis(triphenylphosphine)palladium, palladium acetate, palladium chloride-1,1'-bis(diphenylphosphino)ferrocene, etc. The reaction temperature is not particularly limited and may preferably be in the range of RT~110° C. The reaction time is preferably in the range of 1 hr~24 hr. Alternatively, the compound of the general formula (V) may be reacted with a base such as sodium methoxide in a compound having a substitutable hydrogen atom, such as methanol, whereupon the halogen substituent that has been introduced into $R^1$ can be converted to a methoxy group. Examples of the solvent that can be used here include but are not limited to protic polar solvent such as methanol, ethanol, etc. Exemplary bases include sodium methoxide, sodium ethoxide, etc. The reaction temperature is not particularly limited and may preferably be in the range of RT—80° C. The reaction time is preferably in the range of 1 hr~24 hr.

It should be noted that if $R^1$ in the general formula (I) is a hydrogen atom, this step 2 is skipped and the following step 3 is performed.

(Step 3)

The ester derivative represented by the general formula (V) is hydrolyzed using an aqueous solution of an alkali metal hydroxide such as lithium hydroxide, sodium hydroxide or potassium hydroxide, whereby a carboxylic acid derivative represented by the general formula (VI) can be produced. Reaction solvents that can be used are not particularly limited as long as they are water-miscible organic solvents and may include: protic polar solvents such as methanol, ethanol, etc.; ethers such as tetrahydrofuran, 1,4-dioxane, etc.; and nitriles such as acetonitrile, propionitrile, etc. The reaction temperature is not particularly limited and may preferably be in the range of RT~90° C. The reaction time is preferably in the range of 1 hr~24 hr.

(Step 4)

The carboxylic acid derivative represented by the general formula (VI) and an amine derivative represented by the general formula (VII) or a salt thereof are subjected to a condensation reaction, whereupon a compound represented by the general formula (VIII) can be produced. The condensation reaction may be exemplified by a reaction using a condensation agent in an inert solvent in the presence or absence of a base. Exemplary condensation agents that may be used in this case include carbodiimides such as N,N'-dicyclohexylcarbodiimide, O-(7-azabenzotriazol-1-yl)-N,N, N',N'-tetramethyluronium hexafluorophosphate (HATU), etc. Alternatively, the carboxylic acid derivative represented by the general formula (VI) may first be derived to a reactive intermediate using an activator for a carboxyl group and then reacted with the amine derivative represented by the general formula (VII) or a salt thereof, whereupon the compound represented by the general formula (VIII) can also be produced. Exemplary activation agents for a carboxyl group that may be used in this case include thionyl chloride, phosphorus oxychloride, oxalyl chloride, phosgene, triphosgene, 1,1'-carbonyldiimidazole, ethyl chlorocarbonate, etc. The reaction temperature is not particularly limited and may preferably be in the range of 0° C.~80° C. The reaction time is preferably in the range of 1 hr~24 hr.

(Step 5)

Onto the 4-position of the imidazole ring in the compound represented by the general formula (VIII), a chlorine atom, a bromine atom or an iodine atom can be introduced by a method well known to a person having ordinary skill in the art. For example, the compound represented by the general formula (VIII) can be converted to a bromide represented by the general formula (IX) by acting on N-bromosuccinimide in N,N-dimethylformamide. The solvents that can be used are not particularly limited if they are inert solvents and they include, for example: aromatic hydrocarbons such as benzene, toluene, xylene, etc.; halogenated hydrocarbons such as dichloromethane, chloroform, 1,2-dichloroethane, etc.; nitriles such as acetonitrile, propionitrile, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc. The reaction temperature is not particularly limited and may preferably be in the range of RT~90° C. The reaction time is preferably in the range of 1 hr~24 hr.

(Step 6)

A mixture of the compound represented by the general formula (IX) and an alkyne derivative represented by the general formula (X) is acted upon by a palladium catalyst and a copper catalyst in the presence of a base, whereupon a compound represented by the general formula (XI) can be produced. This reaction is preferably performed in an inert gas (e.g. argon) atmosphere. The solvents that can be used in the reaction are not particularly limited if they are inert solvents and they include, for example: aromatic hydrocarbons such as benzene, toluene, xylene, etc.; halogenated hydrocarbons such as dichloromethane, chloroform, 1,2-dichloroethane, etc.; nitriles such as acetonitrile, propionitrile, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc. Exemplary bases include organic bases such as triethylamine, diisopropylethylamine, etc. Note that in this step, in place of the foregoing inert solvents, the foregoing bases may be used as solvents. Exemplary palladium catalysts include tetrakis(triphenylphosphine)palladium, dichlorobis(triphenylphosphine)palladium, palladium acetate, palladium chloride-1,1'-bis(diphenylphosphino)ferrocene, etc. The palladium catalyst generally suffices to be added in an amount of 1~50 mol %, preferably about 5~20 mol %, of the compound represented by the general formula (IX). Exemplary copper catalysts include copper iodide, etc. The copper catalyst generally suffices to be added in an amount of 1~50 mol %, preferably about 5~20 mol %, of the compound represented by the general formula (IX). The reaction temperature is not particularly limited and may preferably be in the range of RT~90° C. The reaction time is preferably in the range of 1 hr~24 hr.

Here in the production of the compound represented by the general formula (XI), the compound represented by the general formula (X) may be preliminarily prepared to give a desired compound by methods either known or well known to a person having ordinary skill in the art or modifications thereof; alternatively, step 6 may first be performed with a convertible substituent being present and then conversion of the substituent is performed as appropriate to give a desired compound by methods either known or well known to a person having ordinary skill in the art or modifications thereof. Examples of the latter approach include a method that comprises performing step 6 using a compound represented by the general formula (X) in which the substituent X is a hydroxyl group and then converting the hydroxyl group to a fluorine atom or an alkoxy group. If necessary, step 6 may be performed with the foregoing hydroxyl group being protected with a protective group followed by removal of the hydroxyl protecting group.

If desired, the ester derivative represented by the general formula (XI) as obtained in this step may be designed as a pharmaceutically acceptable ester prodrug for the 4-alkynylimidazole derivative of the present invention.

(Step 7)

The ester derivative represented by the general formula (XI) is hydrolyzed using an aqueous solution of an alkali metal hydroxide such as lithium hydroxide, sodium hydroxide, potassium hydroxide, etc., whereupon the compound represented by the general formula (I-1) can be produced. Reaction solvents that can be used are not particularly limited as long as they are water-miscible organic solvents and may include: protic polar solvents such as methanol, ethanol, isopropanol, etc.; ethers such as tetrahydrofuran, 1,4-dioxane, etc.; nitriles such as acetonitrile, propionitrile, etc; or solvent mixtures thereof. The reaction temperature is not particularly limited and may preferably be in the range of RT~90° C. The reaction time is preferably in the range of 1 hr~24 hr.

The compound represented by the general formula (V) in the foregoing Reaction Scheme 1 can also be produced by the following Reaction Scheme 2 (step 8 and step 9).

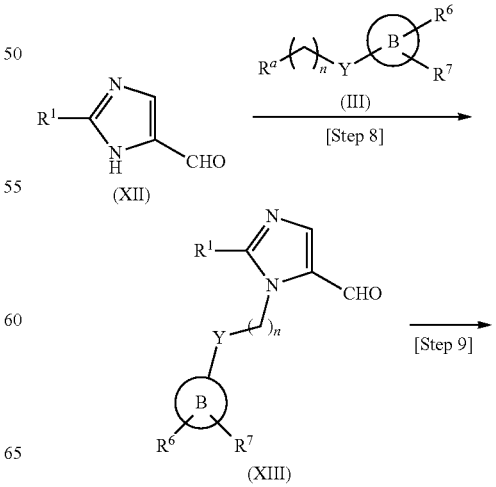

-continued

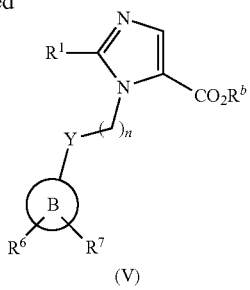

(V)

[wherein B, n, $R^1$, $R^6$, $R^7$ and Y are as defined in the foregoing general formula (I); $R^a$ represents a hydroxyl group or a halogen atom, and $R^b$ represents an alkyl group having 1~15 carbon atoms.]

(Step 8)

A 1H-imidazole-5-carboxylic acid ester derivative represented by the general formula (XII) and an alcohol represented by the general formula (III) ($R^a$ is a hydroxyl group) were acted upon by an azodicarboxylic acid ester derivative such as ethyl azodicarboxylate or diisopropyl azodicarboxylate and a phosphine derivative such as triphenylphosphine or tri-n-butylphosphine in a suitable neutral solvent (e.g. tetrahydrofuran, toluene or a solvent mixture thereof), whereby a corresponding compound represented by the general formula (XIII) can be produced. In the case of using a halide represented by the general formula (III) ($R^a$ is a halogen atom), a compound represented by the general formula (XII) and a base are acted upon the foregoing halide, whereby a corresponding compound represented by the general formula (XIII) can be produced. Examples of the foregoing base include but are not limited to: alkali metal hydroxides such as lithium hydroxide, sodium hydroxide, potassium hydroxide, etc.; alkaline earth metal hydroxides such as magnesium hydroxide, calcium hydroxide, etc.; alkali metal carbonates such as sodium carbonate, potassium carbonate, sodium hydrogencarbonate, potassium hydrogencarbonate, etc.; metal hydrides such as sodium hydride, potassium hydride, etc.; and organic bases such as triethylamine, diisopropylethylamine, etc. The solvents that can be used are not particularly limited if they are inert solvents and they include, for example: aromatic hydrocarbons such as benzene, toluene, xylene, etc.; halogenated hydrocarbons such as dichloromethane, chloroform, 1,2-dichloroethane, etc.; nitriles such as acetonitrile, propionitrile, etc.; ketones such as acetone, etc.; ethers such as diethyl ether, tetrahydrofuran, 1,4-dioxane, etc.; aprotic polar solvents such as N,N-dimethylformamide, N,N-dimethylacetamide, dimethyl sulfoxide, etc. The reaction temperature is not particularly limited and may preferably be in the range of –20° C.~RT. The reaction time is preferably in the range of 1 hr~24 hr.

(Step 9)

The formyl derivative represented by the general formula (XIII) is reacted upon by an alkali metal hydroxide (e.g. potassium hydroxide) and iodine in an alcohol solvent such as methanol or ethanol, whereupon a compound represented by the general formula (V) can be produced. The reaction temperature is not particularly limited and may preferably be in the range of 0° C.~RT. The reaction time is preferably in the range of 1 hr~24 hr. Among the compounds represented by the general formula (I), a compound represented by the general formula (I-2) in which the substituent E is $-CO_2P$ can be produced from the compound represented by the general formula (I-1) in the foregoing Reaction Scheme 1 by means of the following Reaction Scheme 3 (step 10), for example.

<Reaction Scheme 3>

[Formula 19]

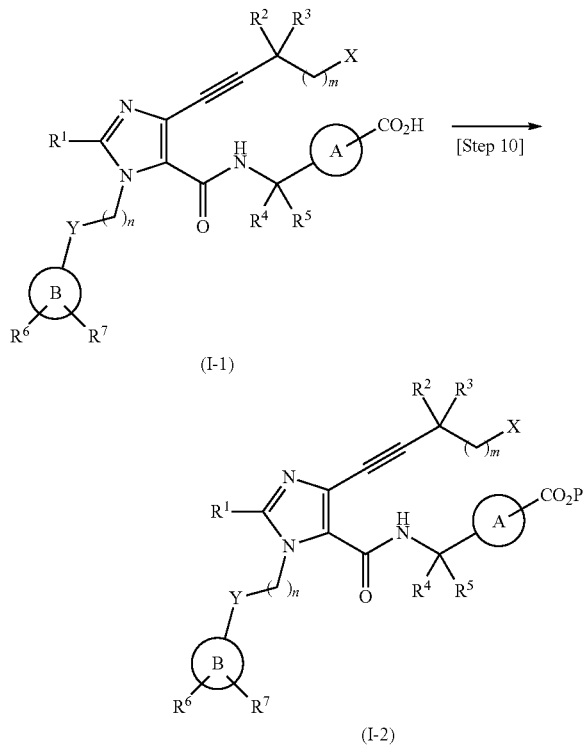

[wherein A, B, m, n, $R^1$~$R^7$, X, Y and $CO_2P$ are as defined in the foregoing general formula (Step 10)

The compound represented by the general formula (I-1) is esterified under customary conditions well known to a person having ordinary skill in the art, whereby it can be easily converted to an ester derivative represented by the general formula (I-2). For example, the carboxylic acid (I-1) is reacted with an alkyl halide such as ethyl bromide or a sulfonic acid ester such as ethyl methanesulfonate in a suitable organic solvent such as N,N-dimethylformamide, tetrahydrofuran, acetone or acetonitrile using a suitable base such as potassium carbonate, sodium carbonate or sodium hydride, whereupon the compound represented by the general formula (I-2) can be produced. The reaction temperature is not particularly limited and may preferably be in the range of 0° C.~100° C. The reaction time is preferably in the range of 1 hr~24 hr.

The compound represented by the general formula (XI) in the foregoing Reaction Scheme 1 can also be produced by the method depicted in the following Reaction Scheme 4 (step 11 to step 14), for example.

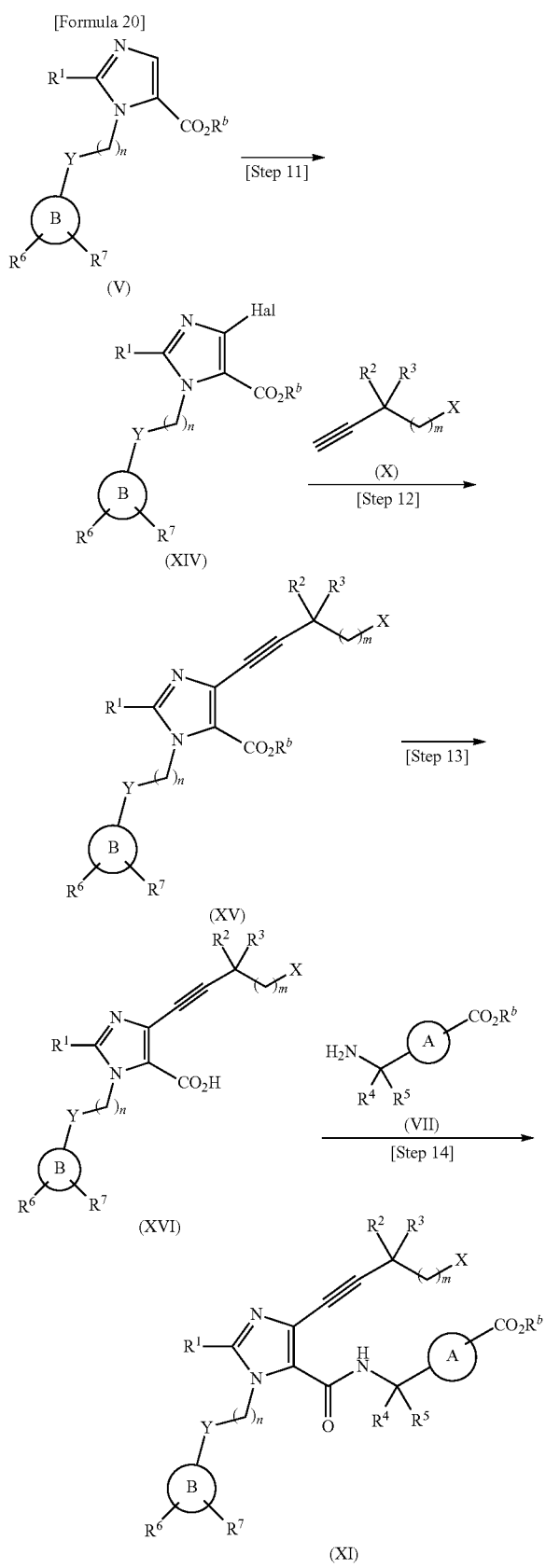

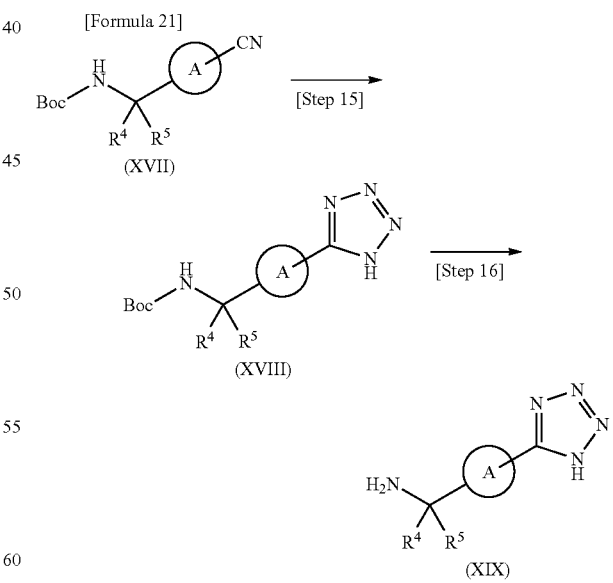

[wherein A, B, m, n, $R^1$~$R^7$, X and Y are as defined in the foregoing general formula (I); $R^b$ represents an alkyl group having 1~15 carbon atoms, and Hal represents a halogen atom.]

(Step 11)

The compound represented by the general formula (V) is processed by the same method as in step 5, whereupon it can be converted to a halide represented by the general formula (XIV).

(Step 12)

The halide represented by the general formula (XIV) is processed by the same method as in step 6, whereupon it can be converted to a compound represented by the general formula (XV).

(Step 13)

The compound represented by the general formula (XV) is processed by the same method as in step 3, whereupon it can be converted to a compound represented by the general formula (XVI).

(Step 14)

The compound represented by the general formula (XVI) is processed by the same method as in step 4, whereupon it can be converted to a compound represented by the general formula (XI).

Among the compounds represented by the general formula (I), a compound in which the substituent E is tetrazolyl can be produced, for example, by the same method, except that an intermediate amine represented by the general formula (XIX) is produced by the process depicted in the following Reaction Scheme 5 and that this intermediate amine represented by the general formula (XIX) is used in place of the compound represented by the general formula (VII) in (step 4) of the foregoing Reaction Scheme 1 or in place of the compound represented by the general formula (VII) in step 14 of the foregoing Reaction Scheme 4.

[wherein A, $R^4$ and $R^5$ are as defined in the foregoing general formula (I).]

(Step 15)

The compound represented by the general formula (XVII) has its cyano group converted to a tetrazolyl group by a method well known to a person having ordinary skill in the art, whereupon it can be converted to a compound represented by the general formula (XVIII). For example, the compound represented by the general formula (XVII) is acted upon by a suitable reagent for constructing a tetrazole ring (e.g. sodium azide, lithium azide, trimethyltin azide, tributyltin azide, etc.) in a solvent inert to the reaction, optionally in the presence of an acid or base, whereupon the compound represented by the general formula (XVIII) can be produced. Examples of the inert solvent that can be used here include N,N-dimethylformamide, dimethyl sulfoxide, tetrahydrofuran, etc. Exemplary acids that can be used include ammonium chloride, hydrochloric acid, zinc bromide, etc. Exemplary bases that can be used include triethylamine, N,N-diisopropylethylamine, etc. The reaction temperature is not particularly limited and may preferably be in the range of RT~150° C. The reaction time is preferably in the range of 1 hr~24 hr.

(Step 16)

The compound represented by the general formula (XVIII) can be converted to a compound represented by the general formula (XIX) by removing the protective tert-butoxycarbonyl group by a deprotecting method that is well known among a person having ordinary skill in the art. Deprotecting methods include those which are described in Greene and Wuts, *Protective Groups in Organic Synthesis*, $3^{rd}$ ed., 1999, for example.

Thus, among the compounds represented by the general formula (I), a compound in which the substituent E is a bioisostere of a carboxyl group may be produced by such a process that an intermediate amine is prepared to give a desired compound using a known method or a modification thereof, followed by the same method as Reaction Scheme 1 or Reaction Scheme 4. Compounds in which the foregoing bioisostere of a carboxyl group can be easily converted from a carboxylic acid may also be produced from the compound (I-1) by a known method or a modification thereof.

The compounds of the present invention that are represented by the general formula (I) as produced by the foregoing methods are isolated and purified as free compounds, salts thereof, hydrates or various solvates (e.g. ethanol solvate) thereof or crystal polymorphisms thereof. Pharmaceutically acceptable salts of the compounds of the present invention can be produced by conventional salt forming reactions. Isolation and purification are performed by applying chemical operations including extractive separation, crystallization, and a variety of fractional chromatographic techniques.

The 4-alkynylimidazole derivatives of the present invention have a superior EP4 receptor antagonistic action, as shown later in Test Example 1. The "EP4 receptor antagonistic action" refers to blocking the EP4 receptor-mediated action of prostaglandin E2 (PGE2). As mediated by the EP4 receptor, PGE2 participates in inflammatory responses (including an immune inflammatory response), relaxation of smooth muscle, pain triggering, differentiation of lymphocytes, enlargement or proliferation of mesangial cells, secretion of gastrointestinal mucus, etc. Hence, the 4-alkynylimidazole derivatives of the present invention which have the EP4 receptor antagonistic action are useful as pharmaceuticals specifically intended for the treatment, namely, therapy or prevention, of diseases associated with the EP4 receptor-mediated action of PGE2 and, in particular, since PGE2 is strongly implicated in inflammatory responses (including an immune inflammatory response) and pain triggering, the 4-alkynylimidazole derivatives of the present invention are more useful as pharmaceuticals specifically intended for the anti-inflammation and/or pain relieving of diseases associated with the EP4 receptor-mediated action of PGE2, for example, the anti-inflammation and/or pain relieving of inflammatory diseases (including immune diseases) and diseases that involve various kinds of pains. Further, the 4-alkynylimidazole derivatives of the present invention are also particularly useful as pharmaceuticals intended for the treatment, namely, therapy or prevention, of immune diseases that result from inflammations as evoked by tissue destruction due to the activation of Th1 cells and/or Th17 cells. Compounds having the EP4 receptor antagonistic action exert therapeutic effects on the foregoing immune diseases since a plurality of compounds with different skeletons that have the EP4 receptor antagonistic action have been verified to be efficacious in EAE (experimental autoimmune encephalomyelitis) models which are animal models for the foregoing immune diseases. Therefore, it can be fully recognized by inference that the 4-alkynylimidazole derivatives of the present invention which have the superior EP4 receptor antagonistic action will also exert therapeutic effects on the foregoing immune diseases. In addition, unlike NSAIDs/COX inhibitors, the 4-alkynylimidazole derivatives of the present invention with their unique mechanism of action will not inhibit the arachidonic acid cascade but block only the site of action of PGE2 and, hence, are expected to display none of the side effects that are characteristic of the NSAIDs/COX inhibitors.

A large number of reports have so far been published concerning the relationship between the EP4 receptor-mediated action of PGE2 and a variety of diseases. Among the diseases associated with the EP4 receptor-mediated action of PGE2, typical ones are diseases that involve inflammations (inflammatory diseases) or diseases that involve pains triggered by inflammation (inflammatory pains) and specific examples include: arthritic pain (Reference Documents 1, 2, 3), articular rheumatism (Reference Documents 2, 3), osteoarthritis (Reference Document 3), lumbago (Reference Document 1), scapulohumeral periarthritis (Reference Document 1), cervico-omo-brachial syndrome (Reference Document 1), tendonitis (Reference Document 4), thecitis (Reference Document 4), multiple sclerosis (Reference Documents 2, 6), systemic lupus erythematosus (Reference Document 1), gout (Reference Document 1), multiple myositis/dermatomyositis (Reference Document 1), angitis syndrome (Reference Document 1), ankylosing spondylitis (Reference Document 1), acute nephritis (Reference Document 14), chronic nephritis (Reference Document 14), ulcerative colitis (Reference Document 2), Crohn's disease (Reference Document 2), atopic dermatitis (Reference Document 6), psoriasis (Reference Document 6), contact dermatitis (Reference Document 6), bursitis (Reference Document 5), interstitial cystitis (Reference Document 12), headache pain (Reference Document 15), arteriosclerosis (Reference Document 1), etc.

Among the foregoing diseases, multiple sclerosis, ulcerative colitis, Crohn's disease, atopic dermatitis, psoriasis, and contact dermatitis are immune diseases that result from inflammations as evoked by tissue destruction due to the activation of Th1 cells and/or Th17 cells (i.e., immune diseases in which Th1 cells and/or Th17 cells are implicated) (Reference Documents 2, 6).

Among the diseases associated with the EP4 receptor-mediated action of PGE2, equally typical are diseases that involve pains triggered by stimulation of peripheral nerve nociceptors (i.e., nociceptive pain) and specific examples include: postoperative pain (Reference Document 1), post-extraction pain (Reference Document 1), swelling/pain after trauma (bruise, sprain, contusion, burn) (Reference Document 1), cancerous pain (Reference Document 1), gingivitis (Reference Document 1), etc. Further, diseases associated with the EP4 receptor-mediated action of PGE2 also include neuropathic pains which are diseases that involve a pain triggered by an impaired nerve due to a certain cause (Reference Document 7) and specific examples may include: allodynia, postherpetic pain, fibromyalgia, pain or numbness that accompany diabetic complications, sciatica, as well as pains due to stroke or spinal cord injury.

Yet other diseases associated with the EP4 receptor-mediated action of PGE2 include: Alzheimer's disease (Reference Document 8), malignant tumors (Reference Document 9) and their metastases (Reference Document 10), aortic aneurysm (Reference Document 11), overactive bladder (Reference Document 12), renal failure (Reference Document 14), patent ductus arteriosus (Reference Document 13), acute lung injury/acute respiratory distress syndrome (Reference Document 16), diabetic retinopathy (Reference Document 17), age-related macular degeneration (Reference Document 17), and postoperative adhesion (Reference Document 18). It should, however, be noted that the diseases associated with the EP4 receptor-mediated action of PGE2 are by no means limited to the examples listed above.

REFERENCE LITERATURE

Reference Document 1: Handbook on How to Select and Use NSAIDs, ed. by S. Sano, Yodosha
Reference Document 2: Sakata D, et al, J Pharmacol Sci, 112, 1-5, 2010
Reference Document 3: Clark P, et al, J Pharmacol Exp Ther, 325, 425-434, 2008
Reference Document 4: Thampatty B P, et al, Gene, 386, 154-161, 2007
Reference Document 5: Petri M, et al. J Rheumatol 31, 1614-1620, 2004
Reference Document 6: Yao C, et al, Nature Medicine, 15, 633-640, 2009
Reference Document 7: St-Jacques B, et al, J Neurochem, 118, 841-854, 2011
Reference Document 8: Hoshino T, et al, J Neurochem, 120, 795-805, 2012
Reference Document 9: Katoh H, et al, Inflammation and Regeneration, 31, 316-324, 2011
Reference Document 10: Ma X, et al, Oncoimmunology, 2, e22647, 2013
Reference Document 11: Yokoyama U, et al, PloS One, 7, e36724, 2012
Reference Document 12: Chuang Y C, et al, BJU Int, 106, 1782-1787, 2010
Reference Document 13: Wright D H, et al, Am J Physiol Regul Integr Comp Physiol, 281, R1345-1360, 2001
Reference Document 14: WO2003/099857
Reference Document 15: Antonova M, et al. J Headache Pain 12, 551-559, 2011
Reference Document 16: Aso H, et al. Am J Physiol Lung Cell Mol Physiol 302, L266-73, 2011
Reference Document 17: Yanni S E, et al. Invest Ophthalmol Vis Sci 50, 5479-5486, 2009
Reference Document 18: Zhang Y, et al. Blood 118, 5355-5364, 2011

As demonstrated in the Test Examples to be described later, the 4-alkynylimidazole derivatives of the present invention showed a superior analgesic effect by significantly increasing pain thresholds in carrageenin-induced pain models and adjuvant-induced chronic arthritis models and they also suppressed joint pain in monoiodoacetic acid-induced joint pain models.

In addition, as demonstrated in the Test Examples to be described later, the 4-alkynylimidazole derivatives of the present invention showed a superior anti-inflammatory effect in carrageenin-induced inflammation models and they also showed a superior anti-inflammatory effect in adjuvant-induced chronic arthritis models.

From these facts, it can be seen that the 4-alkynylimidazole derivatives of the present invention have a superior anti-inflammatory and/or analgesic effect in acute and/or chronic inflammatory pain models.

Hence, against the diseases associated with the EP4 receptor-mediated action of PGE2, the compounds of the present invention are more preferred as pharmaceuticals specifically intended for the anti-inflammation and/or pain relieving of diseases that involve inflammations (inflammatory diseases) or diseases that involve pains triggered by inflammation (inflammatory pains); they are even more preferred as pharmaceuticals specifically intended for the anti-inflammation and/or pain relieving of at least one disease selected from the group consisting of arthritic pain, articular rheumatism, osteoarthritis, lumbago, scapulohumeral periarthritis, cervico-omo-brachial syndrome, tendonitis, and thecitis.

In addition, the 4-alkynylimidazole derivatives of the present invention which have a superior EP4 receptor antagonistic action are useful as EP4 receptor antagonists and are also useful as pharmaceuticals specifically intended for the treatment of immune diseases that result from inflammations as evoked by tissue destruction due to the activation of Th1 cells and/or Th17 cells (i.e., immune diseases in which Th1 cells and/or Th17 cells are implicated). In particular, they are more preferred as pharmaceuticals to be used for the treatment of at least one disease selected from the group consisting of multiple sclerosis, ulcerative colitis, Crohn's disease, atopic dermatitis, psoriasis, and contact dermatitis, and they are even more preferred as pharmaceuticals specifically intended for the treatment of multiple sclerosis.

Pharmaceuticals comprising the 4-alkynylimidazole derivatives of the present invention are administered either systemically or topically by an oral or parenteral route, for example, transdermal, transnasal, transtracheal, transpulmonary, ophthalmic, intravenous injection, hypodermic injection, intrarectal, etc. Dosage forms can be selected as appropriate for the route of administration and include, for example, tablets, troches, sublingual tablets, sugar-coated tablets, capsules, pills, powders, granules, liquids, emulsions, creams, ointments, lotions, jellies, suspensions, syrups, eye drops, nasal drops, inhalants, suppositories, injections, etc. In addition, the pharmaceuticals comprising the 4-alkynylimidazole derivatives of the present invention may contain pharmacologically acceptable carriers, namely, excipients, and depending on the need, may further contain a variety of commonly used additives including binders, disintegrants, coating agents, lubricants, antiseptics, wetting agents, emulsifiers, stabilizers, preservatives, coloring agents, sweeteners, solubilizers, etc.; such pharmaceuticals can be prepared in accordance with conventional methods in the art.

The dosage of the pharmaceuticals comprising the 4-alkynylimidazole derivatives of the present invention may be determined as appropriate for various conditions including the subject to which they are administered, the route of administration, and the symptoms to be controlled; for example, in the case of oral administration to an adult patient, a single dose of the present compound as an active ingredient usually suffices to be in the range of about 0.01~1000 mg, preferably in the range of 0.1~400 mg, and once to three times daily dosing is preferred.

EXAMPLES

Examples and Test Examples are given below to describe the features of the present invention in a more specific way. The materials, the amounts in which they were used, their proportions, the specifics and procedures of the processing, etc. can be varied as appropriate without departing from the spirit of the present invention. Hence, the scope of the present invention should not be interpreted in a way that is limited by the specific examples set out below.

Note that the $^1$H-NMR spectra shown below were measured with JNM-ECA400 Model spectrometer (400 MHz, JEOL Ltd.) using deuterochloroform (CDCl$_3$), deuteromethanol (CD$_3$OD) or deuterated dimethyl sulfoxide (DMSO-d$_6$) as a solvent, and tetramethylsilane (TMS) as an internal standard. Measured chemical shifts are indicated by δ values in ppm and J values (coupling constant) in Hz. Abbreviations s, d, t, q, m and br represent singlet, doublet, triplet, quartet, multiplet and broad, respectively. For measurement of mass spectra (electrospray ionization: ESI-MS), Exactive manufactured by Thermo Fisher Scientific K. K. was used.

Example 1 trans-4-({2-Chloro-4-(3-hydroxy-3-methyl-1-butyn-1-yl)-1-[4-(trifluoromethyl)benzyl]-1H-imidazole-5-carboxamido}methyl)cyclohexanecarboxylic acid (Compound 1)

Compound 1 was produced according to the reaction scheme depicted below:

[Formula 22]

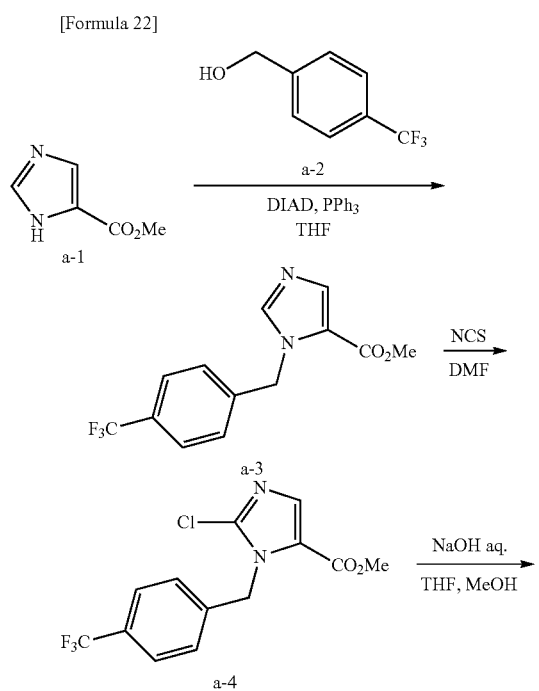

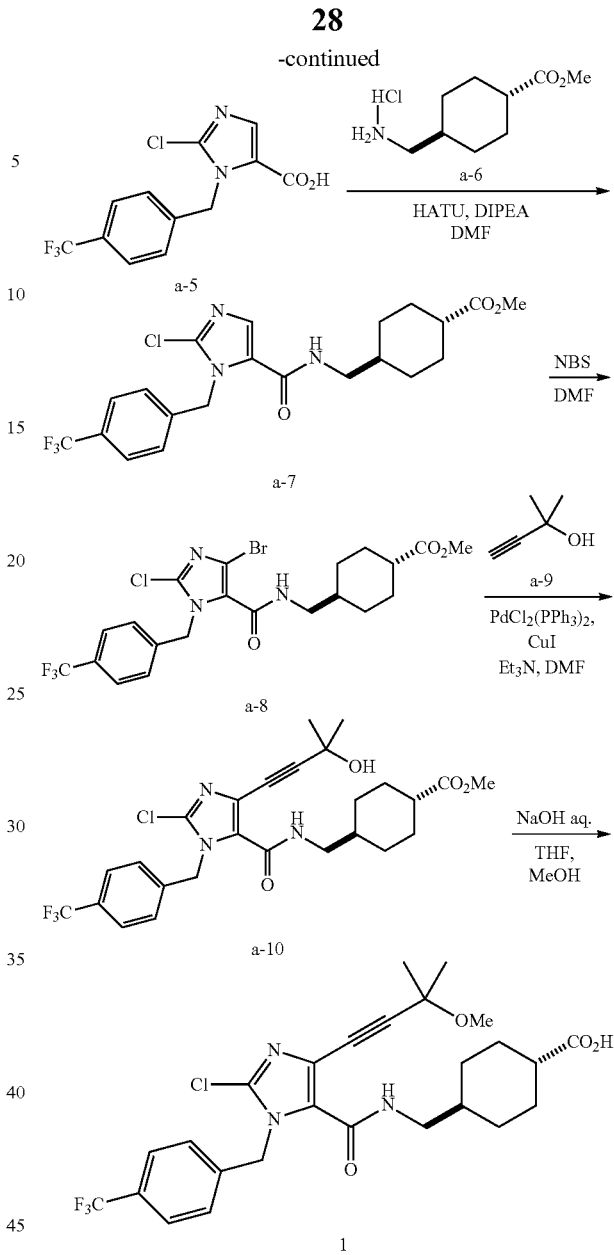

(1) To a solution of methyl 4-imidazole carboxylate (a-1) (5.0 g, 39 mmol) in tetrahydrofuran (THF) (100 mL), p-trifluoromethyl benzyl alcohol (a-2) (6.5 mL, 48 mmol) and triphenylphosphine (PPh$_3$) (12 g, 47 mmol) were added and after adding a toluene solution (25 mL, 48 mmol) of 1.9 mol/L diisopropyl azodicarboxylate (DIAD) dropwise, the resulting mixture was stirred at room temperature for 3 hours. After distilling off the solvents under reduced pressure, the residue was purified by silica gel column chromatography (n-hexane:ethyl acetate=50:50~0:100) and purified again by silica gel (NH) column chromatography (n-hexane: ethyl acetate=90:10~50:50) to give methyl 1-[4-(trifluoromethyl)benzyl]-1H-imidazole-5-carboxylate (a-3) (amount, 7.7 g; yield, 69%).

(2) To a solution of the foregoing compound (a-3) (7.7 g, 27 mmol) in N,N-dimethylformamide (DMF) (54 mL), N-chlorosuccinimide (NCS) (3.6 g, 27 mmol) was added and the resulting mixture was stirred overnight at room temperature. To the reaction mixture, a saturated aqueous solution of sodium hydrogencarbonate was added and after extraction with ethyl acetate, the organic layer was washed successively with water and saturated brine. After drying the organic layer over anhydrous sodium sulfate, the solvents were distilled off under reduced pressure. The residue was purified by silica gel column chromatography (n-hexane:ethyl acetate=90:10~50:50) to give methyl 2-chloro-1-[4-(trifluoromethyl)benzyl]-1H-imidazole-5-carboxylate (a-4) (amount, 3.7 g; yield, 43%).

(3) To a solution of the foregoing compound (a-4) (3.72 g, 11.7 mmol) in a solvent mixture of THF (80 mL) and methanol (80 mL), an aqueous solution (14.6 mL, 58.4 mmol) of 4 mol/L sodium hydroxide was added and the resulting mixture was stirred at room temperature for 3 hours. To the reaction mixture, 6 mol/L hydrochloric acid was added to adjust pH to 5 or below and extraction was conducted with ethyl acetate. The organic layer was dried over anhydrous sodium sulfate and the solvents were distilled off under reduced pressure to give 2-chloro-1-[4-(trifluoromethyebenzyl]-1H-imidazole-5-carboxylic acid (a-5) (amount, 3.50 g; yield, 98%).

(4) To a solution of the foregoing compound (a-5) (0.390 g, 1.28 mmol) in DMF (3.9 mL), methyl trans-4-aminomethyl cyclohexanecarboxylate hydrochloride (a-6) (0.293 g, 1.41 mmol), N,N-diisopropylethylamine (DIPEA) (0.543 mL, 3.20 mmol) and O-(7-azabenzotriazol-1-yl)-N,N,N',N'-tetramethyluronium hexafluorophosphate (HATU) (0.535 g, 1.41 mmol) were added and the resulting mixture was stirred overnight at room temperature. Water was added to the reaction mixture and extraction was conducted with ethyl acetate. The organic layer was successively washed with water and saturated brine and the organic layer was dried over anhydrous sodium sulfate. The solvents were distilled off under reduced pressure and the residue was purified by silica gel column chromatography (n-hexane:ethyl acetate=50:50~0:100) to give methyl trans-4-({2-chloro-1-[4-(trifluoromethyl)benzyl]-1H-imidazole-5-carboxamido}methyl)cyclohexanecarboxylate (a-7) (amount, 0.516 g; yield, 88%).

(5) To a solution of the foregoing compound (a-7) (0.516 g, 1.23 mmol) in DMF (4 mL), N-bromosuccinimide (NBS) (0.261 g, 1.47 mmol) was added and the resulting mixture was stirred at 60° C. for 6 hours. Water was added to the reaction mixture and extraction was conducted with ethyl acetate. The organic layer was successively washed with water and saturated brine and the organic layer was dried over anhydrous sodium sulfate. The solvents were distilled off under reduced pressure and the residue was purified by silica gel column chromatography (n-hexane:ethyl acetate=70:30~30:70) to give methyl trans-4-({4-bromo-2-chloro-1-[4-(trifluoromethyl)benzyl]-1H-imidazole-5-carboxamido}methyl)cyclohexanecarboxylate (a-8) (amount, 0.536 g; yield, 82%).

(6) To a solution of the foregoing compound (a-8) (0.476 g, 0.888 mmol) in DMF (7.5 mL), 2-methyl-3-butyn-2-ol (a-9) (0.260 mL, 2.66 mmol) and triethylamine (2.5 mL) were added. The resulting mixture in solution was degassed and after adding dichlorobis(triphenylphosphine)palladium (0.0311 g, 0.0444 mmol) and copper iodide (0.0169 g, 0.0887 mmol), the mixture was stirred overnight at 60° C. The reaction mixture was cooled to room temperature and after adding a saturated aqueous solution of ammonium chloride, extraction was conducted with ethyl acetate. The organic layer was dried over anhydrous sodium sulfate and the solvents were distilled off under reduced pressure. The residue was purified by silica gel column chromatography (n-hexane:ethyl acetate=50:50~0:100) to give methyl trans-4-({2-chloro-4-(3-hydroxy-3-methyl-1-butyn-1-yl)-1-[4-(trifluoromethyl)benzyl]-1H-imidazole-5-carboxamido}methyl)cyclohexanecarboxylate (a-10) (amount, 0.442 g; yield, 92%).

(7) To a solution of the foregoing compound (a-10) (68 mg, 0.13 mmol) in a solvent mixture of THF (0.70 mL) and methanol (0.70 mL), an aqueous solution (0.70 mL, 1.4 mmol) of 2 mol/L sodium hydroxide was added and the resulting mixture was stirred overnight at room temperature. The reaction mixture was neutralized with 2 mol/L hydrochloric acid and after extraction with chloroform, the organic layer was dried over anhydrous sodium sulfate. The solvents were distilled off under reduced pressure and the residue was purified by silica gel column chromatography (chloroform:methanol=98:2~90:10) to give trans-4-({2-chloro-4-(3-hydroxy-3-methyl-1-butyn-1-yl)-1-[4-(trifluoromethyl)benzyl]-1H-imidazole-5-carboxamido}methyl)cyclohexanecarboxylic acid (Compound 1) (amount, 59 mg; yield, 90%). The structural formula of Compound 1 and the data on its properties will be shown later in Table 1.

(8) In the same way, Compounds 15~17, 23, 24, 26, 27, 29~34, 36, 38 and 39 also listed later in Table 1 were produced from the respectively corresponding starting materials. The structural formulas of these compounds and the data on their properties will be shown later in Table 1.

Example 2

4-({2-Chloro-4-(3-hydroxy-3-methyl-1-butyn-1-yl)-1-[4-(trifluoromethyl)benzyl]-1H-imidazole-5-carboxamido}methyl)benzoic acid (Compound 2)

Compound 2 was produced according to the reaction scheme depicted below:

[Formula 23]

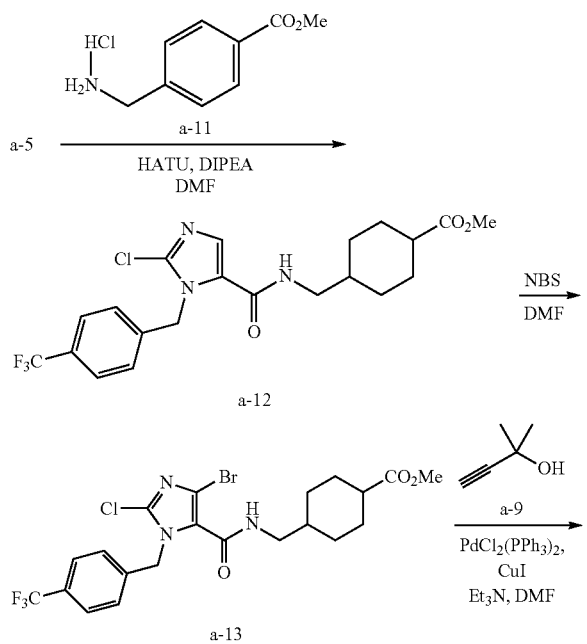

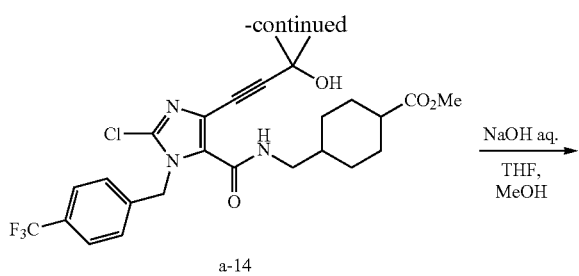

a-14

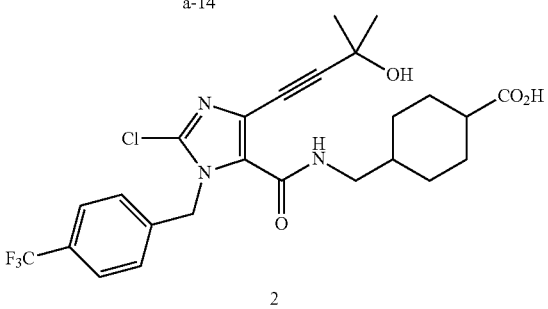

2

(1) To a solution in DMF (87 mL) of compound (a-5) (8.7 g, 29 mmol) as obtained in Example 1, methyl p-(aminomethyl)benzoate hydrochloride (a-11) (6.9 g, 34 mmol), DIPEA (12 mL, 71 mmol) and HATU (12 g, 31 mmol) were added and the resulting mixture was stirred overnight at room temperature. Water was added to the reaction mixture and after extraction with ethyl acetate, the organic layer was successively washed with water and saturated brine. After drying the organic layer over anhydrous sodium sulfate, the solvents were distilled off under reduced pressure. The residue was purified by silica gel column chromatography (n-hexane:ethyl acetate=50:50~0:100) to give methyl 4-({2-chloro-1-[4-(trifluoromethyl)benzyl]-1H-imidazole-5-carboxamido}methyl)benzoate (a-12) (amount, 11 g; yield, 85%).

(2) To a solution of the foregoing compound (a-12) (56 mg, 0.12 mmol) in DMF (0.6 mL), NBS (24 mg, 0.14 mmol) was added and the resulting mixture was stirred at room temperature for an hour, then stirred at 60° C. for 3 hours. To the reaction mixture, water was added and after extraction with ethyl acetate, the organic layer was washed with water and saturated brine. After drying the organic layer over anhydrous sodium sulfate, the solvents were distilled off under reduced pressure. The residue was purified by silica gel column chromatography (n-hexane:ethyl acetate=90:10~50:50) to give methyl 4-({4-bromo-2-chloro-1-[4-(trifluoromethyl)benzyl]-1H-imidazole-5-carboxamido}methyl)benzoate (a-13) (amount, 44 mg; yield, 66%).

(3) To a solution of the foregoing compound (a-13) (6.9 g, 13 mmol) in DMF (100 mL), 2-methyl-3-butyn-2-ol (a-9) (3.8 mL, 39 mmol) and triethylamine (34 mL) were added. The resulting mixture in solution was degassed and after adding dichlorobis(triphenylphosphine)palladium (0.45 g, 0.65 mmol) and copper iodide (0.25 g, 1.3 mmol), the resulting mixture was stirred at 60° C. for 3 hours. The reaction mixture was cooled to room temperature and after adding a saturated aqueous solution of ammonium chloride, extraction was conducted with ethyl acetate. The organic layer was dried over anhydrous sodium sulfate and the solvents were distilled off under reduced pressure. The residue was purified by silica gel column chromatography (n-hexane:ethyl acetate=70:30~0:100) to give methyl 4-({2-chloro-4-(3-hydroxy-3-methyl-1-butyn-1-yl)-1-[4-(trifluoromethyl)benzyl]-1H-imidazole-5-carboxamido}methyl)benzoate (a-14) (amount, 4.5 g; yield, 65%).

(4) To a solution of the foregoing compound (a-14) (31 mg, 0.058 mmol) in a solvent mixture of THF (0.3 mL) and methanol (0.3 mL), an aqueous solution (87 μL, 0.17 mmol) of 2 mol/L sodium hydroxide was added and the resulting mixture was stirred overnight at room temperature. The reaction mixture was neutralized with 2 mol/L hydrochloric acid and after extraction with chloroform, the organic layer was dried over anhydrous sodium sulfate. The solvents were distilled off under reduced pressure and the residue was purified by silica gel column chromatography (chloroform:methanol=98:2~80:20) to give 4-({2-chloro-4-(3-hydroxy-3-methyl-1-butyn-1-yl)-1-[4-(trifluoromethyl)benzyl]-1H-imidazole-5-carboxamido}methyl)benzoic acid (Compound 2) (amount, 19 mg; yield, 70%). The structural formula of Compound 2 and the data on its properties will be shown later in Table 1.

(5) In the same way, Compounds 3~5 and 44 also listed later in Table 1 were produced from the respectively corresponding starting materials. The structural formulas of these compounds and the data on their properties will be shown later in Table 1.

Example 3 trans-4-{[2-Chloro-4-(3-hydroxy-3-methyl-1-butyn-1-yl)-1-(4-methylbenzyl)-1H-imidazole-5-carboxamido]methyl}cyclohexanecarboxylic acid (Compound 21)

Compound 21 was produced according to the reaction scheme depicted below:

[Formula 24]

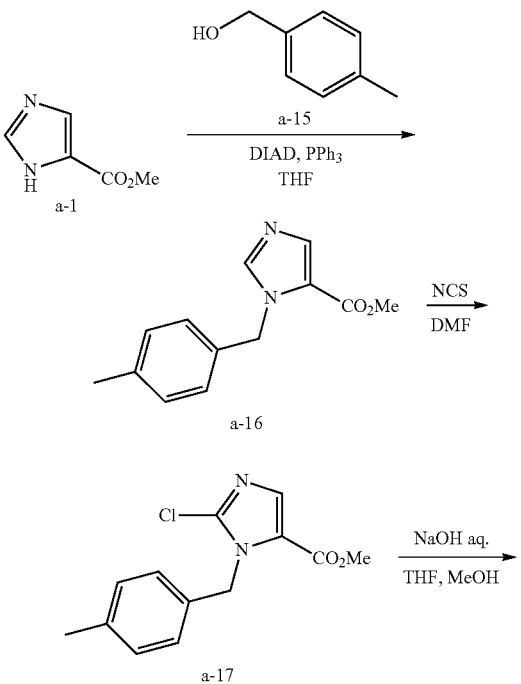

-continued

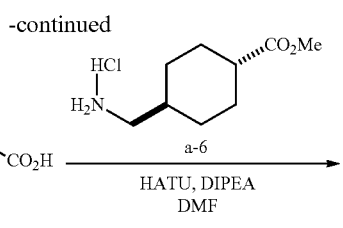

a-18

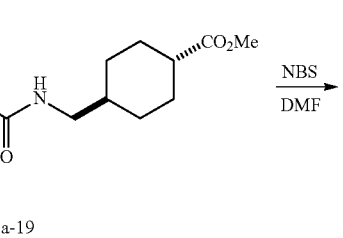

a-19

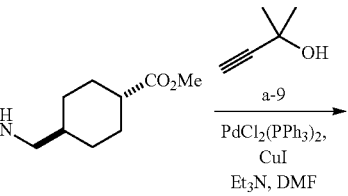

a-20

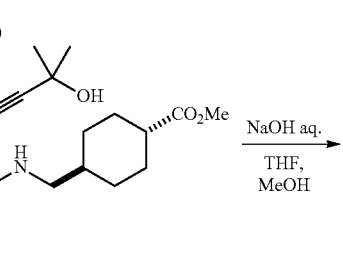

a-21

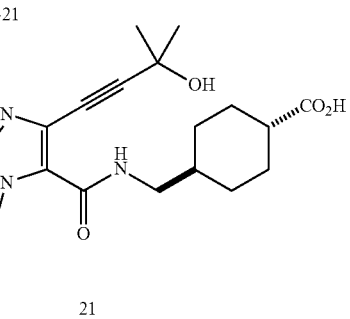

21

(1) To a solution of methyl 4-imidazole carboxylate (a-1) (3.0 g, 24 mmol) in THF (60 mL), p-methylbenzyl alcohol (a-15) (2.9 g, 24 mmol) and PPh₃ (16 g, 60 mmol) were added and after adding a toluene solution (32 mL, 60 mmol) of 1.9 mol/L DIAD dropwise, the resulting mixture was stirred at room temperature for 15 hours. After distilling off the solvents under reduced pressure, purification was performed by silica gel column chromatography (n-hexane: ethyl acetate=1:1) to give methyl 1-(4-methylbenzyl)-1H-imidazole-5-carboxylate (a-16) (amount, 4.3 g; yield, 78%).

(2) To a solution of the foregoing compound (a-16) (4.3 g, 19 mmol) in DMF (90 mL), NCS (2.7 g, 21 mmol) was added and the resulting mixture was stirred overnight at room temperature. To the reaction mixture, a saturated aqueous solution of sodium hydrogencarbonate was added and after extraction with ethyl acetate, the organic layer was successively washed with water and saturated brine. After drying the organic layer over anhydrous sodium sulfate, the solvents were distilled off under reduced pressure. The residue was purified by silica gel column chromatography (n-hexane:ethyl acetate=1:1) to give methyl 2-chloro-1-(4-methylbenzyl)-1H-imidazole-5-carboxylate (a-17) (amount, 2.3 g; yield, 46%).

(3) To a solution of the foregoing compound (a-17) (0.54 g, 2.0 mmol) in a solvent mixture of THF (5 mL) and methanol (5 mL), an aqueous solution (3.1 mL, 6.1 mmol) of 2 mol/L sodium hydroxide was added and the resulting mixture was stirred at room temperature for 12 hours. To the reaction mixture, 1 mol/L hydrochloric acid was added to adjust pH to 5 or less and the precipitating solids were recovered by filtration to give 2-chloro-1-(4-methylbenzyl)-1H-imidazole-5-carboxylic acid (a-18) (amount, 0.42 g; yield, 81%).

(4) To a solution of the foregoing compound (a-18) (0.42 g, 1.7 mmol) in DMF (15 mL), methyl trans-4-aminomethyl cyclohexanecarboxylate hydrochloride (a-6) (0.45 g, 2.2 mmol), DIPEA (0.89 mL, 5.0 mmol) and HATU (0.82 g, 2.2 mmol) were added and the resulting mixture was stirred overnight at room temperature. Water was added to the reaction mixture and extraction was conducted with ethyl acetate. The organic layer was successively washed with water and saturated brine and the organic layer was dried over anhydrous sodium sulfate. The solvents were distilled off under reduced pressure and the residue was purified by silica gel column chromatography (n-hexane:ethyl acetate=1:1) to give methyl trans-4-{[2-chloro-1-(4-methyl-benzyl)-1H-imidazole-5-carboxamido]methyl}cyclohexanecarboxylate (a-19) (amount, 0.56 g; yield, 83%).

(5) To a solution of the foregoing compound (a-19) (0.55 g, 1.4 mmol) in DMF (5 mL), NBS (0.32 g, 1.8 mmol) was added and the resulting mixture was stirred overnight at 60° C. To the reaction mixture, a saturated aqueous solution of sodium hydrogencarbonate was added and extraction was conducted with ethyl acetate. The organic layer was successively washed with water and saturated brine and the organic layer was dried over anhydrous sodium sulfate. The solvents were distilled off under reduced pressure and the residue was purified by silica gel column chromatography (n-hexane: ethyl acetate=3:1) to give methyl trans-4-{[4-bromo-2-chloro-1-(4-methylbenzyl)-1H-imidazole-5-carboxamido]methyl}cyclohexanecarboxylate (a-20) (amount, 0.44 g; yield, 66%).

(6) To a solution of the foregoing compound (a-20) (0.18 g, 0.38 mmol) in DMF (1 mL), 2-methyl-3-butyn-2-ol (a-9) (56 μL, 0.57 mmol) and triethylamine (0.27 mL) were added. The mixture in solution was degassed and after adding dichlorobis(triphenylphosphine)palladium (13 mg, 0.019 mmol) and copper iodide (3.6 mg, 0.019 mmol), the resulting mixture was stirred at 50° C. for 5 hours. The reaction mixture was cooled to room temperature and after adding a saturated aqueous solution of ammonium chloride, extraction was conducted with ethyl acetate. The organic layer was dried over anhydrous sodium sulfate and the solvents were distilled off under reduced pressure. The residue was purified by silica gel column chromatography (n-hexane:ethyl acetate=1:1) to give methyl trans-4-{[2-chloro-4-(3-hydroxy-3-methyl-1-butyn-1-yl)-1-(4-methyl-benzyl)-1H-imidazole-5-carboxamido]methyl}cyclohexanecarboxylate (a-21) (amount, 0.097 g; yield, 53%).

(7) To a solution of the foregoing compound (a-21) (97 mg, 0.20 mmol) in a solvent mixture of THF (1 mL) and methanol (1 mL), an aqueous solution (1 mL, 2.0 mmol) of 2 mol/L sodium hydroxide was added and the resulting mixture was stirred overnight at room temperature. The reaction mixture was neutralized with 1 mol/L hydrochloric acid and after extraction with chloroform, the organic layer was dried over anhydrous sodium sulfate. The solvents were distilled off under reduced pressure and the residue was purified by silica gel column chromatography (chloroform:methanol=10:1) to give trans-4-{[2-chloro-4-(3-hydroxy-3-methyl-1-butyn-1-yl)-1-(4-methylbenzyl)-1H-imidazole-5-carboxamido]methyl}cyclohexanecarboxylic acid (Compound 21) (amount, 81 mg; yield, 86%). The structural formula of Compound 21 and the data on its properties will be shown later in Table 1.

Example 4 trans-4-({2-Chloro-4-(3-methoxy-3-methyl-1-butyn-1-yl)-1-[4-(trifluormethyl)benzyl]-1H-imidazole-5-carboxamido}methyl)cyclohexanecarboxylic acid (Compound 10)

Compound 10 was produced according to the reaction scheme depicted below:

[Formula 25]

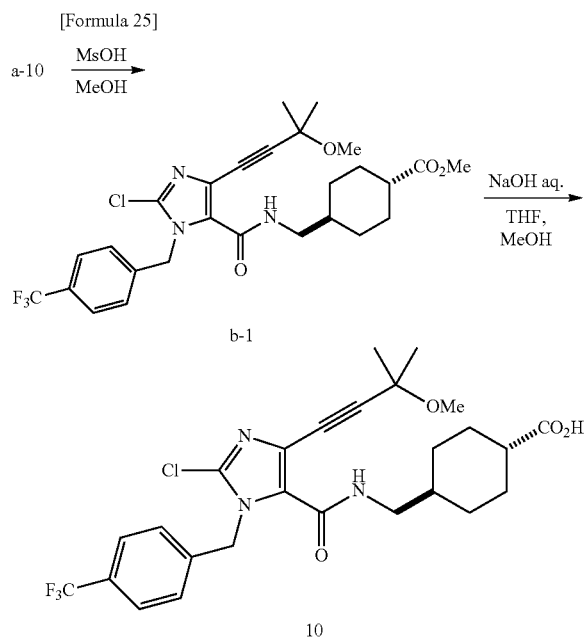

(1) To a solution in methanol (1.6 mL) of compound (a-10) (81 mg, 0.15 mmol) as obtained in Example 1, methanesulfonic acid (MsOH) (10 μL, 0.15 mmol) was added and the resulting mixture was stirred at 60° C. for 4 hours. The reaction mixture was cooled to room temperature and a saturated aqueous solution of sodium hydrogencarbonate was added. Extraction was conducted with ethyl acetate and after drying the organic layer over anhydrous sodium sulfate, the solvents were distilled off under reduced pressure. The residue was purified by silica gel column chromatography (n-hexane:ethyl acetate=90:10~30:70) to give methyl trans-4-({2-chloro-4-(3-methoxy-3-methyl-1-butyn-1-yl)-1-[4-(trifluoromethyl)benzyl]-1H-imidazole-5-carboxamido}methyl)cyclohexanecarboxylate (b-1) (amount, 70 mg; yield, 84%).

(2) To a solution of the foregoing compound (b-1) (70 mg, 0.13 mmol) in a solvent mixture of THF (1 mL) and methanol (1 mL), an aqueous solution (0.19 mL, 0.38 mmol) of 2 mol/L sodium hydroxide was added and the resulting mixture was stirred overnight at room temperature. The reaction mixture was neutralized with 2 mol/L hydrochloric acid and after extraction with chloroform, the organic layer was dried over anhydrous sodium sulfate. The solvents were distilled off under reduced pressure and the residue was purified by silica gel column chromatography (chloroform:methanol=98:2~90:10) to give trans-4-({2-chloro-4-(3-methoxy-3-methyl-1-butyn-1-yl)-1-[4-(trifluoromethyl)benzyl]-1H-imidazole-5-carboxamido}methyl)cyclohexanecarboxylic acid (Compound 10) (amount, 60 mg; yield, 88%). The structural formula of Compound 10 and the data on its properties will be shown later in Table 1.

(3) In the same way, Compounds 11~13, 25, 28, 35, 37, 40, 41, 43, 45, 66, and 69 also listed later in Table 1 were produced from the respectively corresponding starting materials. The structural formulas of these compounds and the data on their properties will be shown later in Table 1.

Example 5 trans-4-{[2-Chloro-4-(3-methoxy-3-methyl-1-butyn-1-yl)-1-(4-methylbenzyl)-1H-imidazole-5-carboxamido]methyl}cyclohexanecarboxylic acid (Compound 22)

Compound 22 was produced according to the reaction scheme depicted below:

[Formula 26]

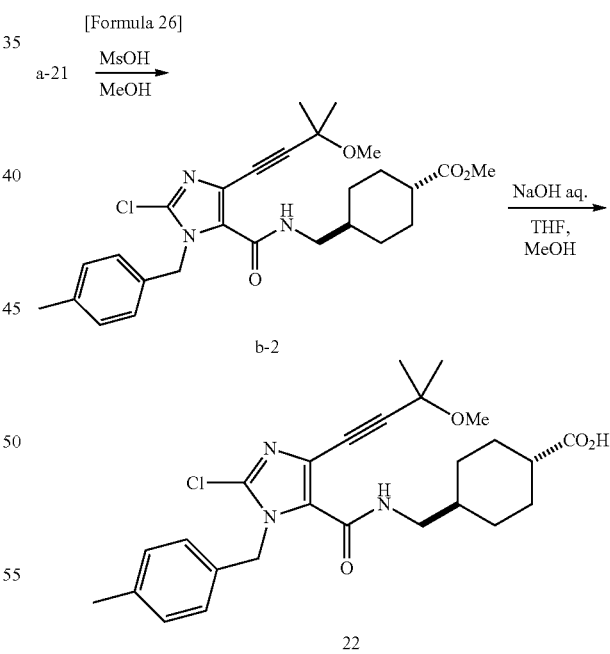

(1) To a solution in methanol (76 mL) of compound (a-21) (3.7 g, 7.61 mmol) as obtained in Example 3, MsOH (2.5 mL, 38 mmol) was added and the resulting mixture was stirred at 60° C. for 5 hours. The reaction mixture was cooled to room temperature and a saturated aqueous solution of sodium hydrogencarbonate was added. Extraction was conducted with ethyl acetate and after drying the organic layer over anhydrous sodium sulfate, the solvents were distilled off under reduced pressure. The residue was purified by silica gel column chromatography (n-hexane:ethyl acetate=1:1) to give methyl trans-4-{[2-chloro-4-(3-methoxy-3-methyl-1-butyn-1-yl)-1-(4-methylbenzyl)-1H-imidazole-5-carboxamido]methyl}cyclohexanecarboxylate (b-2) (amount, 2.8 mg; yield, 74%).

(2) To a solution of the foregoing compound (b-2) (23 mg, 0.047 mmol) in a solvent mixture of THF (0.2 mL) and methanol (0.2 mL), an aqueous solution (0.11 mL, 0.47 mmol) of 4 mol/L sodium hydroxide was added and the resulting mixture was stirred at room temperature for 3 hours. The reaction mixture was neutralized with 2 mol/L hydrochloric acid and after extraction with chloroform, the organic layer was dried over anhydrous sodium sulfate. The solvents were distilled off under reduced pressure and the residue was purified by silica gel column chromatography (chloroform:methanol=4:1) to give trans-4-{[2-chloro-4-(3-methoxy-3-methyl-1-butyn-1-yl)-1-(4-methylbenzyl)-1H-imidazole-5-carboxamido]methyl}cyclohexanecarboxylic acid (Compound 22) (amount, 18 mg; yield, 77%). The structural formula of Compound 22 and the data on its properties will be shown later in Table 1.

Example 6 trans-4-({2-Chloro-4-(3-fluoro-3-methyl-1-butyn-1-yl)-1-[4-(trifluoromethyl)benzyl]-1H-imidazole-5-carboxamido}methyl)cyclohexanecarboxylic acid (Compound 14)

Compound 14 was produced according to the reaction scheme depicted below:

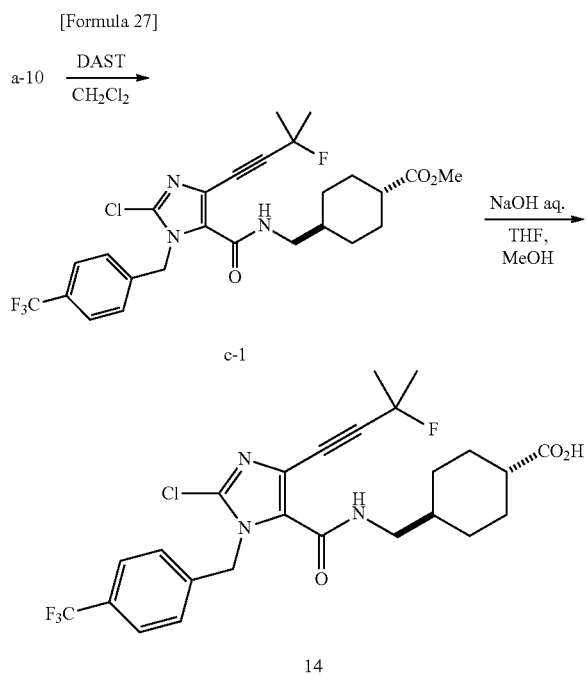

(1) A solution in dichloromethane (1.9 mL) of compound (a-10) (100 mg, 0.185 mmol) as obtained in Example 1 was cooled to 0° C. To the cooled solution, (diethylamino)sulfate trifluoride (DAST) (29 μL, 0.22 mmol) was added and the resulting mixture was stirred at 0° C. for 3 hours. Water was added to the reaction mixture and after extraction with chloroform, the organic layer was dried over anhydrous sodium sulfate. The solvents were distilled off under reduced pressure and the residue was purified by silica gel column chromatography (n-hexane:ethyl acetate=70:30~0:100) to give methyl trans-4-({2-chloro-4-(3-fluoro-3-methyl-1-butyn-1-yl)-1-[4-(trifluoromethyl)benzyl]-1H-imidazole-5-carboxamido}methyl)cyclohexanecarboxylate (c-1) (amount, 68 mg; yield, 68%).

(2) The foregoing compound (c-1) was hydrolyzed by the same method as in Example 1(7) to give trans-4-({2-chloro-4-(3-fluoro-3-methyl-1-butyn-1-yl)-1-[4-(trifluoromethyl)benzyl]-1H-imidazole-5-carboxamido}methyl)cyclohexanecarboxylic acid (Compound 14). The structural formula of Compound 14 and the data on its properties will be shown later in Table 1.

Example 7 trans-4-({2-Ethyl-4-(3-hydroxy-3-methyl-1-butyn-1-yl)-1-[4-(trifluoromethyl)benzyl]-1H-imidazole-5-carboxamido}methyl)cyclohexanecarboxylic acid (Compound 18)

Compound 18 was produced according to the reaction scheme depicted below:

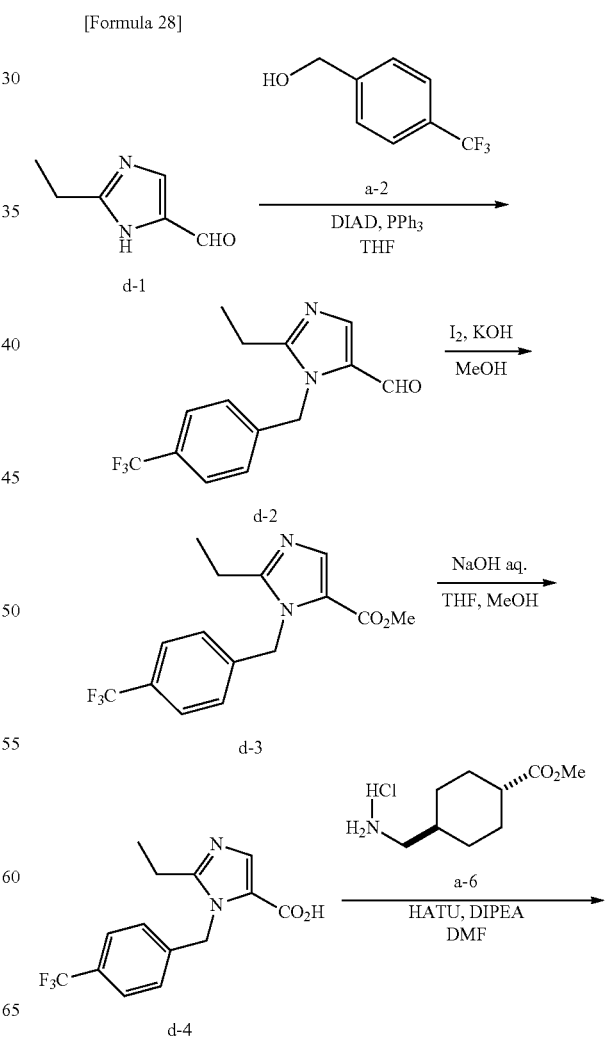

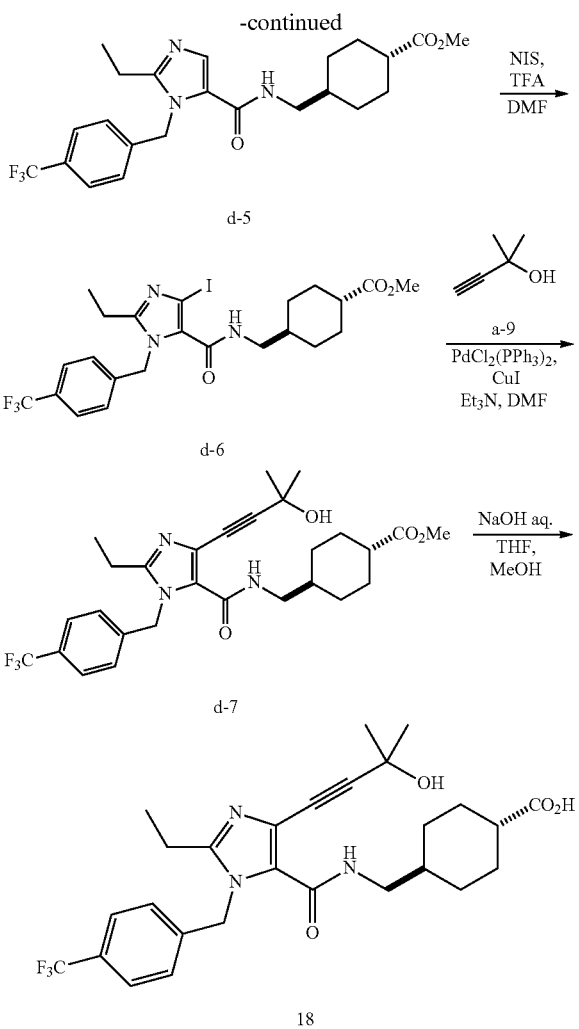

(1) To a solution of 2-ethyl-1H-imidazole-5-carbaldehyde (d-1) (1.0 g, 8.1 mmol) in THF (80 mL), 4-trifluoromethyl benzyl alcohol (a-2) (1.56 g, 8.87 mmol) and PPh₃ (2.5 g, 9.7 mmol) were added and the resulting mixture was stirred at 0° C. To the reaction mixture, a toluene solution (5.1 mL, 9.7 mmol) of 1.9 mol/L DIAD was added and the resulting mixture was stirred at room temperature for 17 hours. The solvents were distilled off under reduced pressure and the residue was purified by silica gel column chromatography (n-hexane:ethyl acetate=60:40~0:100) to give 2-ethyl-1-[4-(trifluoromethyl)benzyl]-1H-imidazole-5-carbaldehyde (d-2) as a crude product. To a solution of the foregoing compound (d-2) in methanol (5.6 mL), a solution of iodine (4.10 g, 16 mmol) in methanol (60 mL) and a solution of potassium hydroxide (1.80 g, 32 mmol) in methanol (41 mL) were added at 0° C. and the resulting mixture was stirred at room temperature for 3 hours. To the reaction mixture, 1 mol/L hydrochloric acid was added to adjust pH to about 5 and after adding a saturated aqueous solution of sodium thiosulfate, extraction was conducted with ethyl acetate. The organic layer was dried over anhydrous sodium sulfate and the solvents were distilled off under reduced pressure. The residue was purified by silica gel column chromatography (n-hexane:ethyl acetate=60:40~0:100) to give methyl 2-ethyl-1-[4-(trifluoromethyl)benzyl]-1H-imidazole-5-carboxylate (d-3) (amount, 780 mg; yield, 31% (in 2 steps)).

(2) To a solution of the foregoing compound (d-3) (250 mg, 0.801 mmol) in a solvent mixture of THF (4.0 mL) and methanol (4.0 mL), an aqueous solution (2.0 mL, 8.0 mmol) of 4 mol/L sodium hydroxide was added and the resulting mixture was stirred at room temperature for 4 hours. The reaction mixture was neutralized with 1 mol/L hydrochloric acid and the solvents were distilled off under reduced pressure. The residue was purified by silica gel column chromatography (chloroform:methanol=99:1~80:20) to give 2-ethyl-1-[4-(trifluoromethyl)benzyl-1H-imidazole-5-carboxylic acid (d-4) as a crude product. To a solution of the foregoing compound (d-4) in DMF (9.4 mL), methyl trans-4-aminomethyl cyclohexanecarboxylate hydrochloride (a-6) (270 mg, 1.30 mmol), HATU (390 mg, 0.103 mmol) and DIPEA (0.410 mL, 2.35 mmol) were added successively and the resulting mixture was stirred overnight at room temperature. To the reaction mixture, a saturated ammonium chloride solution was added and extraction was conducted with chloroform. The organic layer was dried over anhydrous sodium sulfate. The solvents were distilled off under reduced pressure and the residue was purified by silica gel column chromatography (chloroform:methanol=99:1~70:30) and purified again by silica gel (NH) column chromatography (n-hexane:ethyl acetate=60:40~0:100) to give methyl trans-4-({2-ethyl-1-[4-(trifluoromethyl)benzyl]-1H-imidazole-5-carboxamido}methyl)cyclohexanecarboxylate (d-5) (amount, 240 mg; yield, 57% (in 2 steps)).

(3) To a solution of the foregoing compound (d-5) (50 mg, 0.11 mmol) in DMF (0.60 mL), N-iodosuccinimide (NIS) (75 mg, 0.33 mmol) and trifluoroacetic acid (TFA) (0.055 mL) were added and the resulting mixture was stirred at 100° C. for 15 hours. The reaction mixture was cooled to room temperature, successively washed with a saturated aqueous solution of sodium hydrogencarbonate and a saturated aqueous solution of sodium thiosulfate, and subjected to extraction with ethyl acetate. The organic layer was dried over anhydrous sodium sulfate and the solvents were distilled off under reduced pressure and the residue was purified by silica gel column chromatography (chloroform:methanol=99:1~70:30) and purified again by silica gel (NH) column chromatography (n-hexane:ethyl acetate=60:40~0:100) to give methyl trans-4-({2-ethyl-4-iodo-1-[4-(trifluoromethyl)benzyl]-1H-imidazole-5-carboxamido}methyl)cyclohexanecarboxylate (d-6) (amount, 40 mg; yield, 63%).

(4) To a solution of the foregoing compound (d-6) (73 mg, 0.13 mmol) in DMF (1.3 mL), 2-methyl-3-butyn-2-ol (a-9) (0.037 mL, 0.38 mmol), triethylamine (0.43 mL), dichlorobis(triphenylphosphine)palladium (4.4 mg, 6.3 μmol and copper iodide (2.4 mg, 0.013 mmol) were added and the resulting mixture was stirred at 60° C. for 16 hours. The reaction mixture was cooled to room temperature and after adding a saturated ammonium chloride solution, extraction was conducted with ethyl acetate. The organic layer was dried over anhydrous sodium sulfate and after distilling off the solvents under reduced pressure, the residue was purified by silica gel (NH) column chromatography (n-hexane:ethyl acetate=80:20~0:100) to give methyl trans-4-({2-ethyl-4-(3-hydroxy-3-methyl-1-butyn-1-yl)-1-[4-(trifluoromethyl)benzyl]-1H-imidazole-5-carboxamido}methyl)cyclohexanecarboxylate (d-7) (amount, 69 mg; yield, 100%).

(5) To a solution of the foregoing compound (d-7) (22 mg, 0.040 mmol) in a solvent mixture of THF (0.20 mL) and methanol (0.20 mL), an aqueous solution (0.10 mL, 0.41 mmol) of 4 mol/L sodium hydroxide was added and the resulting mixture was stirred at room temperature for 3 hours. To the reaction mixture, 1 mol/L hydrochloric acid was added for neutralization and after extraction with chloroform, the organic layer was dried over anhydrous sodium sulfate. The solvents were distilled off under reduced pressure and the residue was purified by silica gel column chromatography (chloroform:methanol=99:1~70:30) to give trans-4-({2-ethyl-4-(3-hydroxy-3-methyl-1-butyn-1-yl)-1-[4-(trifluoromethyl)benzyl]-1H-imidazole-5-carboxamido}methyl)cyclohexanecarboxylic acid (Compound 18) (amount, 21 mg; yield, 98%).

Using Compound 18, the same method as described in Example 4 was applied to produce Compound 19.

The structural formulas of these Compounds 18 and 19 and the data on their properties will be shown later in Table 1.

Example 8

4-({2-Cyclopropyl-4-(3-hydroxy-3-methyl-1-butyn-1-yl)-1-[4-(trifluoromethyl)benzyl]-1H-imidazole-carboxamido}methyl)benzoic acid (Compound 20)

Compound 20 was produced according to the reaction scheme depicted below:

[Formula 29]

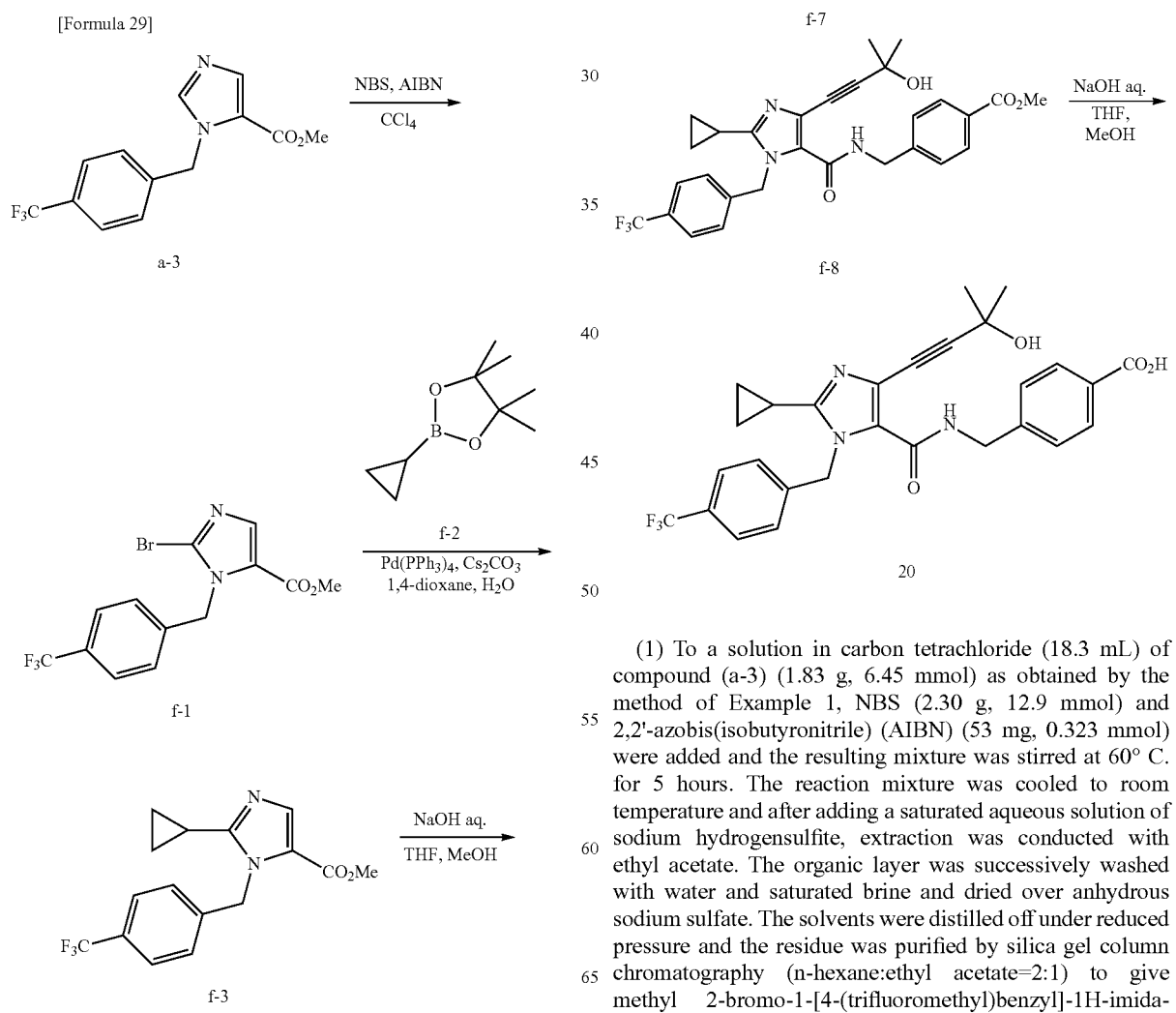

(1) To a solution in carbon tetrachloride (18.3 mL) of compound (a-3) (1.83 g, 6.45 mmol) as obtained by the method of Example 1, NBS (2.30 g, 12.9 mmol) and 2,2'-azobis(isobutyronitrile) (AIBN) (53 mg, 0.323 mmol) were added and the resulting mixture was stirred at 60° C. for 5 hours. The reaction mixture was cooled to room temperature and after adding a saturated aqueous solution of sodium hydrogensulfite, extraction was conducted with ethyl acetate. The organic layer was successively washed with water and saturated brine and dried over anhydrous sodium sulfate. The solvents were distilled off under reduced pressure and the residue was purified by silica gel column chromatography (n-hexane:ethyl acetate=2:1) to give methyl 2-bromo-1-[4-(trifluoromethyl)benzyl]-1H-imidazole-5-carboxylate (f-1) (amount, 1.48 g; yield, 63%).

(2) To a solution of the foregoing compound (f-1) (741 mg, 2.04 mmol) in a solvent mixture of 1,4-dioxane (1.0 mL) and water (0.10 mL), cyclopropyl boronic acid pinacol ester (f-2) (0.559 mL, 3.06 mmol) was added and the resulting mixture was degassed. To the reaction mixture, tetrakis(triphenylphosphine)palladium (236 mg, 0.204 mmol) and cesium carbonate (2.00 g, 6.12 mmol) were added and the resulting mixture was stirred overnight at 100° C. To the reaction mixture, water was added and extraction was conducted with ethyl acetate, followed by drying over anhydrous sodium sulfate. The solvents were distilled off under reduced pressure and the residue was purified by silica gel column chromatography (n-hexane:ethyl acetate=1:1) to give methyl 2-cyclopropyl-1-[4-(trifluoromethyl)benzyl]-1H-imidazole-5-carboxylate (f-3) (amount, 80.5 mg; yield, 12%).

(3) To a solution of the foregoing compound (f-3) (142 mg, 2.04 mmol) in a solvent mixture of THF (1 mL) and methanol (1 mL), an aqueous solution (1.10 mL, 4.38 mmol) of 4 mol/L sodium hydroxide was added and the resulting mixture was stirred at room temperature for 3 hours. To the reaction mixture, 1 mol/L hydrochloric acid was added for neutralization and extraction was conducted with ethyl acetate. The organic layer was successively washed with water and saturated brine and dried over anhydrous sodium sulfate. The solvents were distilled off under reduced pressure and the residue was purified by silica gel column chromatography (chloroform:methanol=10:1) to give 2-cyclopropyl-1-[4-(trifluoromethyl)benzyl]-1H-imidazole-5-carboxylic acid (f-4) (amount, 153 mg; yield, 100%).

(4) To a solution of the foregoing compound (f-4) (136 mg, 0.438 mmol) in DMF (4.4 mL), methyl 4-aminomethylbenzoate hydrochloride (f-5) (106 mg, 0.526 mmol), DIPEA (0.191 mL, 1.10 mmol) and HATU (183 mg, 0.482 mmol) were added and the resulting mixture was stirred overnight at room temperature. To the reaction mixture, water was added and after extraction with ethyl acetate, the organic layer was successively washed with water and saturated brine. The organic layer was dried over anhydrous sodium sulfate and the solvents were distilled off under reduced pressure. The residue was purified by silica gel column chromatography (chloroform:methanol=10:1) to give methyl 4-({2-cyclopropyl-1-[4-(trifluoromethyl)benzyl]-1H-imidazole-5-carboxamido}methyl)benzoate (f-6) (amount, 178 mg; yield, 89%).

(5) To a solution of the foregoing compound (f-6) (50 mg, 0.11 mmol) in DMF (1.1 mL), N-iodosuccinimide (74 mg, 0.33 mmol) and TFA (0.11 mL) were added and the resulting mixture was stirred overnight at 100° C. The reaction mixture was cooled to room temperature and after adding a saturated aqueous solution of sodium hydrogencarbonate, extraction was conducted with ethyl acetate. The organic layer was successively washed with water and saturated brine and the organic layer was dried over anhydrous sodium sulfate. The solvents were distilled off under reduced pressure. The residue was purified by silica gel column chromatography (chloroform:methanol=10:1) to give methyl 4-({2-cyclopropyl-4-iodo-1-[4-(trifluoromethyl)benzyl]-1H-imidazole-5-carboxamido}methyl)benzoate (f-7) (amount, 38 mg; yield, 59%).

(6) To a solution of the foregoing compound (f-7) (35 mg, 0.060 mmol) in DMF (1.0 mL), 2-methyl-3-butyn-2-ol (a-9) (0.018 mL, 0.18 mmol) and triethylamine (0.35 mL) were added. The reaction mixture was degassed and dichlorobis(triphenylphosphine)palladium (2.1 mg, 3.0 μmol) and copper iodide (1.1 mg, 6.0 μmol) were added, followed by stirring at 50° C. for an hour. The reaction mixture was cooled to room temperature and after adding a saturated aqueous solution of ammonium chloride, extraction was conducted with ethyl acetate. The organic layer was dried over anhydrous sodium sulfate and the solvents were distilled off under reduced pressure. The residue was purified by silica gel column chromatography (chloroform:methanol=10:1) to give methyl 4-({2-cyclopropyl-4-(3-hydroxy-3-methyl-1-butyn-1-yl)-1-[4-(trifluoromethyl)benzyl]-1H-imidazole-5-carboxamido}methyl)benzoate (f-8) (amount, 23 mg; yield, 70%).

(7) To a solution of the foregoing compound (f-8) (22 mg, 0.041 mmol) in a solvent mixture of THF (0.30 mL) and methanol (0.30 mL), an aqueous solution (0.10 mL, 0.41 mmol) of 4 mol/L sodium hydroxide was added and the resulting mixture was stirred at room temperature for 3 hours. The reaction mixture was neutralized with 2 mol/L hydrochloric acid and after extraction with chloroform, the organic layer was dried over anhydrous sodium sulfate. The solvents were distilled off under reduced pressure and the residue was purified by silica gel column chromatography (chloroform:methanol=10:1) to give 4-({2-cyclopropyl-4-(3-hydroxy-3-methyl-1-butyn-1-yl)-1-[4-(trifluoromethyl)benzyl]-1H-imidazole-5-carboxamido}methyl)benzoic acid (Compound 20) (amount, 22 mg; yield, 100%).

Using Compound 20, the same method as described in Example 4 was applied to produce Compound 46.

The structural formulas of these Compounds 20 and 46 and the data on their properties will be shown later in Table 1.

Example 9

4-({1-[2-(4-Chlorophenoxy)ethyl]-2-cyclopropyl-4-(3-methoxy-3-methyl-1-butyn-1-yl)-1H-imidazole-5-carboxamido}methyl)benzoic acid (Compound 47)

Compound 47 was produced according to the reaction scheme depicted below:

[Formula 30]

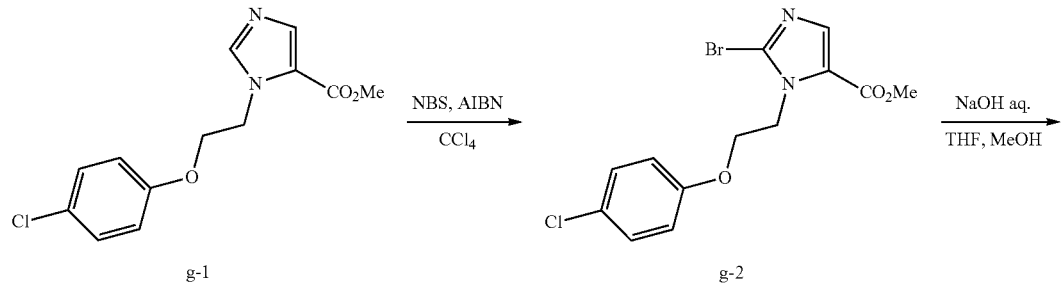

-continued
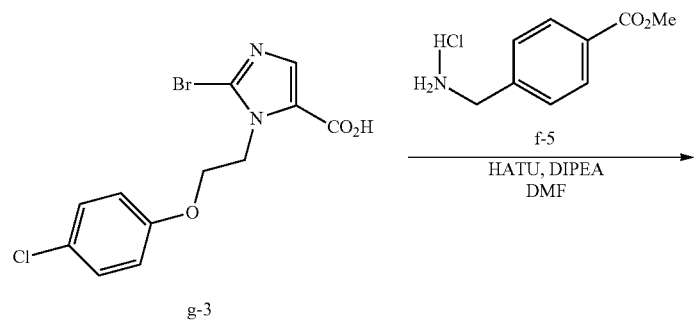
g-3
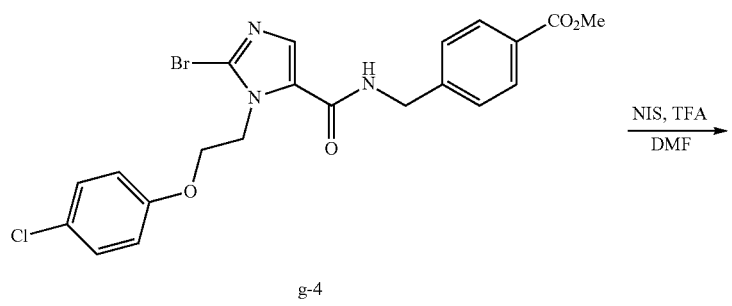
g-4
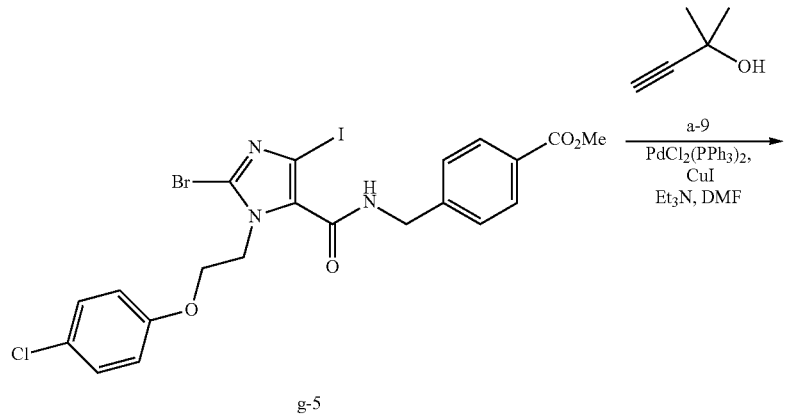
g-5
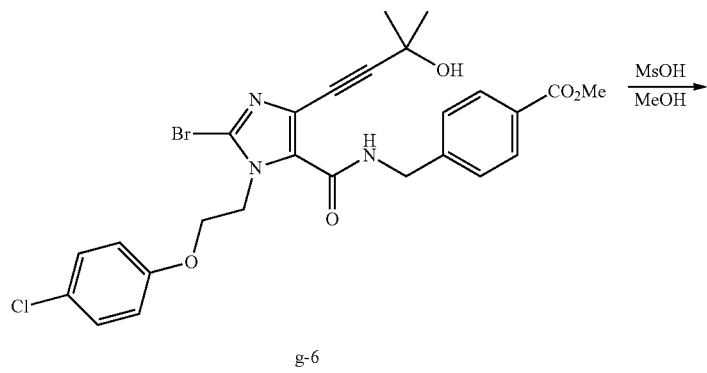
g-6

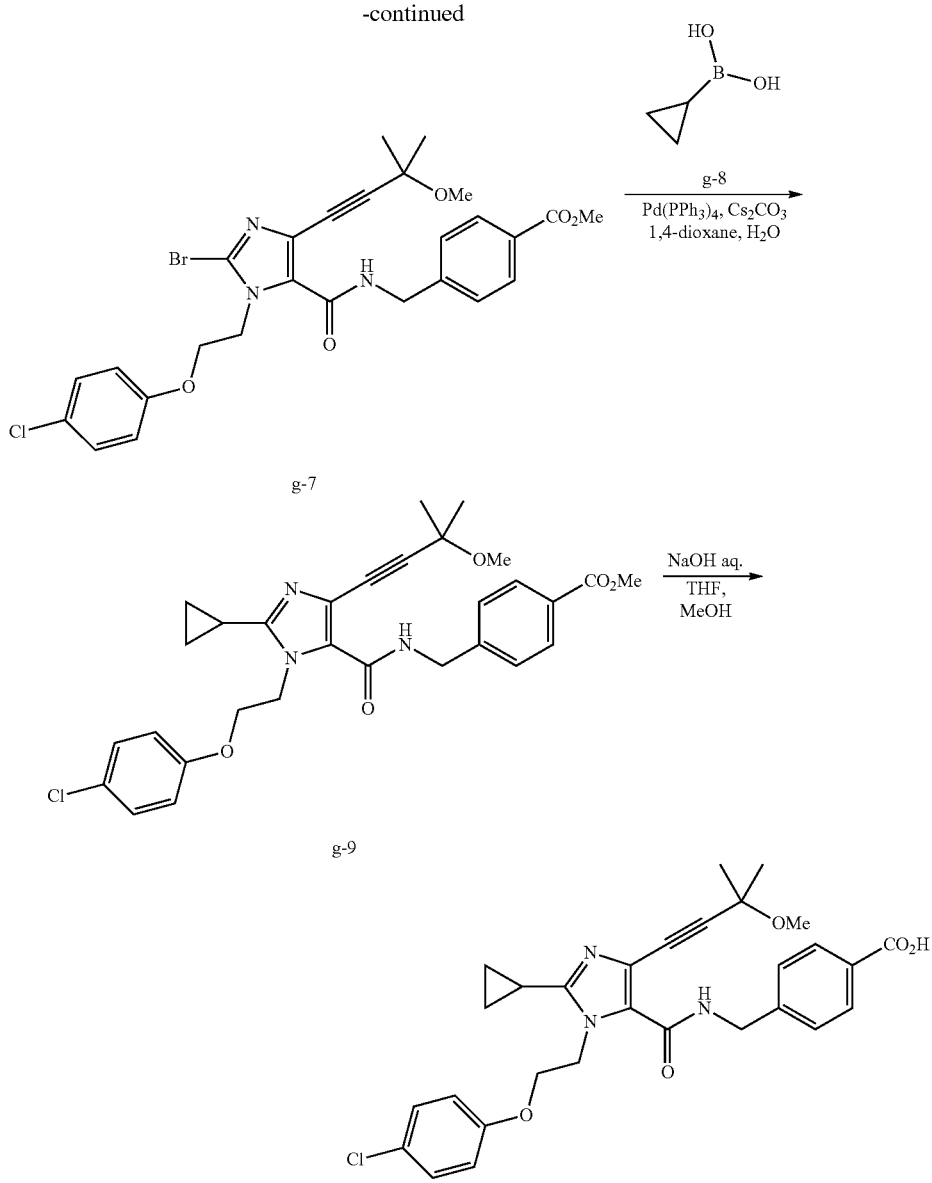

(1) To a solution in carbon tetrachloride (10 mL) of methyl 1-[2-(4-chlorophenoxy)ethyl]-1H-imidazole-5-carboxylate (g-1) (1.00 g, 3.56 mmol) as obtained by the same method as in Examples 1~3, NBS (1.27 g, 7.12 mmol) and 2,2'-azobis(isobutyronitrile) (29 mg, 0.18 mmol) were added and the resulting mixture was stirred at 60° C. for 5 hours. The reaction mixture was cooled to room temperature and after adding a saturated aqueous solution of sodium hydrogensulfite, extraction was conducted with chloroform. The organic layer was successively washed with a saturated aqueous solution of sodium hydrogensulfite, water and saturated brine and then dried over anhydrous sodium sulfate. The solvents were distilled off under reduced pressure and the residue was purified by silica gel column chromatography (n-hexane:ethyl acetate=1:1) to give methyl 2-bromo-1-[2-(4-chlorophenoxy)ethyl]-1H-imidazole-5-carboxylate (g-2) (amount, 398 g; yield, 31%).

(2) To a solution of the foregoing compound (g-2) (388 mg, 1.08 mmol) in a solvent mixture of THF (1.4 mL) and methanol (1.4 mL), an aqueous solution (2.7 mL, 11 mmol) of 4 mol/L sodium hydroxide was added and the resulting mixture was stirred at room temperature for 3 hours. To the reaction mixture, 2 mol/L hydrochloric acid was added and the precipitating solids were recovered by filtration and washed with water. The resulting solids were dried under reduced pressure to give 2-bromo-1-[2-(4-chlorophenoxy) ethyl]-1H-imidazole-5-carboxylic acid (g-3) (amount, 325 mg; yield, 87%).

(3) To a solution of the foregoing compound (g-3) (314 mg, 0.909 mmol) in DMF (9.1 mL), methyl 4-aminomethylbenzoate hydrochloride (f-5) (220 mg, 1.09 mmol), DIPEA (0.397 mL, 2.27 mmol) and HATU (380 mg, 1.00 mmol) were added and the resulting mixture was stirred overnight at room temperature. To the reaction mixture, water was added and extraction was conducted with ethyl acetate. The organic layer was successively washed with water and saturated brine and dried over anhydrous sodium sulfate. The solvents were distilled off under reduced pressure and the residue was purified by silica gel column chromatography (chloroform:methanol=10:1) to give methyl 4-({2-bromo-1-[2-(4-chlorophenoxy)ethyl]-1H-imidazole-5-carboxamido}methyl)benzoate (g-4) (amount, 398 mg; yield, 89%).

(4) To a solution of the foregoing compound (g-4) (175 mg, 0.354 mmol) in DMF (3.5 mL), N-iodosuccinimide (NIS) (399 mg, 1.77 mmol) and TFA (0.41 mL) were added and the resulting mixture was stirred overnight at 100° C. The reaction mixture was cooled to room temperature and after adding a saturated aqueous solution of sodium hydrogensulfite, extraction was conducted with ethyl acetate. The organic layer was successively washed with a saturated aqueous solution of sodium hydrogensulfite, water and saturated brine and then dried over anhydrous sodium sulfate. The solvents were distilled off under reduced pressure and the residue was purified by silica gel column chromatography (n-hexane:ethyl acetate=1:1) to give methyl 4-({2-bromo-1-[2-(4-chlorophenoxy)ethyl]-4-iodo-1H-imidazole-5-carboxamido}methyl)benzoate (g-5) (amount, 88.8 mg; yield, 41%).

(5) To a solution of the foregoing compound (g-5) (84.1 mg, 0.136 mmol) in DMF (1 mL), triethylamine (0.35 mL) was added and the resulting mixture was degassed. To the reaction mixture, 2-methyl-3-butyn-2-ol (a-9) (0.023 mL, 0.23 mmol), dichlorobis(triphenylphosphine)palladium (4.8 mg, 0.0068 mmol) and copper iodide (2.6 mg, 0.014 mmol) were added and the resulting mixture was stirred at room temperature for 2 hours. To the reaction mixture, water was added and extraction was conducted with ethyl acetate. The organic layer was successively washed with water and saturated brine and dried over anhydrous sodium sulfate. The solvents were distilled off under reduced pressure and the residue was purified by silica gel column chromatography (n-hexane:ethyl acetate=1:1) to give methyl 4-({2-bromo-1-[2-(4-chlorophenoxy)ethyl]-4-(3-hydroxy-3-methyl-1-butyn-1-yl)-1H-imidazole-5-carboxamido}methyl)benzoate (g-6) (amount, 120 mg; yield, 75%).

(6) To a solution of the foregoing compound (g-6) (49 mg, 0.085 mmol) in methanol (1.0 mL), MsOH (0.028 mL, 0.42 mmol) was added and the resulting mixture was stirred at 60° C. for 5 hours. The reaction mixture was cooled to room temperature and after adding a saturated aqueous solution of sodium hydrogencarbonate, extraction was conducted with ethyl acetate. The organic layer was successively washed with water and saturated brine and dried over anhydrous sodium sulfate. The solvents were distilled off under reduced pressure and the residue was purified by silica gel column chromatography (n-hexane:ethyl acetate=1:1) to give methyl 4-({2-bromo-1-[2-(4-chlorophenoxy)ethyl]-4-(3-methoxy-3-methyl-1-butyn-1-yl)-1H-imidazole-5-carboxamido}methyl)benzoate (g-7) (amount, 38 mg; yield, 76%).

(7) To a solution of the foregoing compound (g-7) in a solvent mixture of 1,4-dioxane (1.0 mL) and water (0.10 mL), cyclohexylboronic acid monohydrate (g-8) (32 mg, 0.31 mmol) was added and the reaction mixture was degassed. Cesium carbonate (60 mg, 0.18 mmol) and tetrakis(triphenylphosphine)palladium (7.1 mg, 6.1 mop were added and the resulting mixture was stirred overnight at 100° C. The reaction mixture was cooled to room temperature and after adding a saturated aqueous solution of ammonium chloride, extraction was conducted with ethyl acetate. The organic layer was successively washed with water and saturated brine and dried over anhydrous sodium sulfate. The solvents were distilled off under reduced pressure and the residue was purified by silica gel column chromatography (n-hexane:ethyl acetate=1:1) to give methyl 4-({1-[2-(4-chlorophenoxy)ethyl]-2-cyclopropyl-4-(3-methoxy-3-methyl-1-butyn-1-yl)-1H-imidazole-5-carboxamido}methyl)benzoate (g-9) (amount, 21 mg; yield, 64%).

(8) To a solution of the foregoing compound (g-9) (20 mg, 0.037 mmol) in a solvent mixture of THF (0.50 mL) and methanol (0.50 mL), an aqueous solution (46 μL, 0.19 mmol) of 4 mol/L sodium hydroxide was added and the resulting mixture was stirred at room temperature for 3 hours. To the reaction mixture, 2 mol/L hydrochloric acid was added to adjust pH to about 5 and extraction was conducted with ethyl acetate. The organic layer was successively washed with water and saturated brine and dried over anhydrous sodium sulfate. The solvents were distilled off under reduced pressure and the residue was purified by silica gel column chromatography (chloroform:methanol=10:1) to give 4-({1-[2-(4-chlorophenoxy)ethyl]-2-cyclopropyl-4-(3-methoxy-3-methyl-1-butyn-1-yl)-1H-imidazole-5-carboxamido}methyl)benzoic acid (Compound 47) (amount, 20 mg; yield, 100%). The structural formula of Compound 47 and the data on its properties will be shown later in Table 1.

Example 10

4-{[2-Chloro-1-(4-fluorobenzyl)-4-(3-methoxy-3-methyl-1-butyn-1-yl)-1H-imidazole-5-carboxamido]methyl}benzoic acid (Compound 56)

Compound 56 was produced according to the reaction scheme depicted below:

[Formula 31]

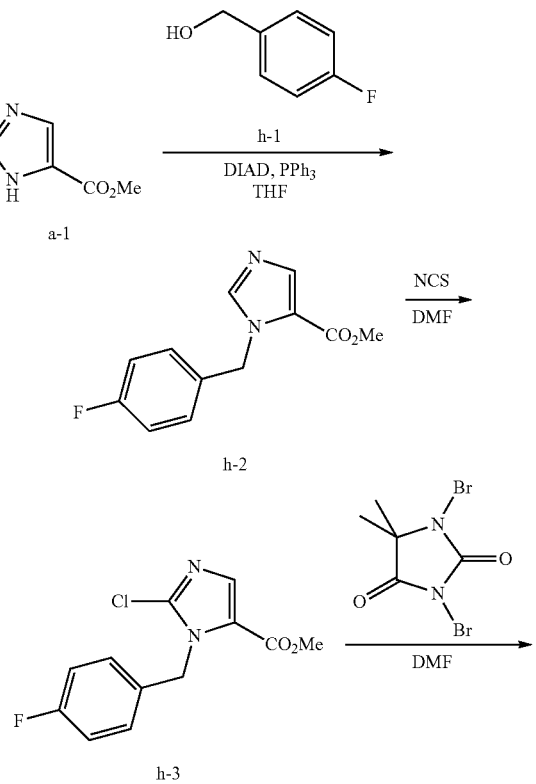

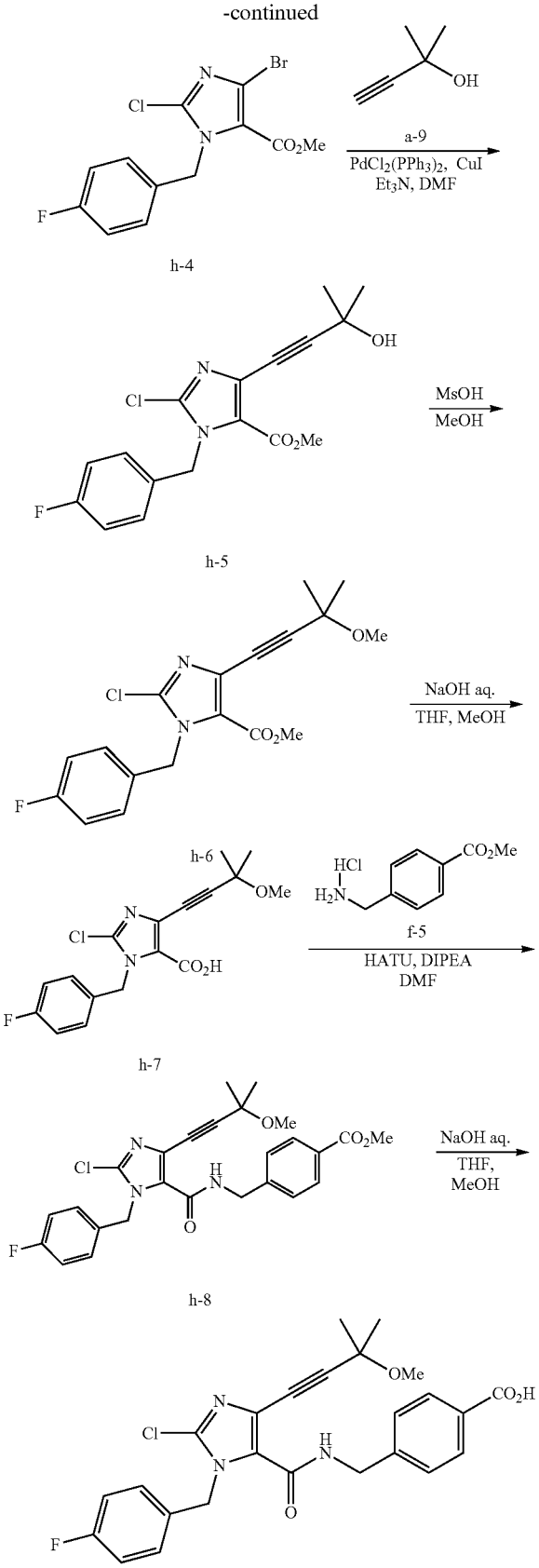

(1) To a solution of methyl 4-imidazole carboxylate (a-1) (1.2 g, 9.5 mmol) and (4-fluorophenyl)methanol (h-1) (1.2 mL, 11 mmol) in THF (12 mL), PPh$_3$ (3.0 g, 11 mmol) and DIAD (2.2 mL, 11 mmol) were added and the resulting mixture was stirred overnight at room temperature. The solvent was distilled off under reduced pressure and ethyl acetate and n-hexane were added; the resulting solids were recovered by filtration. The solvents in the filtrate were distilled off under reduced pressure and the residue was purified by silica gel column chromatography (n-hexane:ethyl acetate=90:10~50:50) to give methyl 1-(4-fluorobenzyl)-1H-imidazole-5-carboxylate (h-2) (amount, 1.6 g; yield, 73%).

(2) A solution of the foregoing compound (h-2) (1.6 g, 7.0 mmol) and NCS (1.0 g, 7.7 mmol) in DMF (11 mL) was stirred overnight at room temperature. To the reaction mixture, a saturated aqueous solution of sodium hydrogencarbonate was added and after extraction with ethyl acetate, the organic layer was washed with water and saturated brine, followed by drying over anhydrous sodium sulfate. The solvents in the organic layer were distilled off under reduced pressure and the residue was purified by silica gel column chromatography (n-hexane:ethyl acetate=90:10~50:50) to give methyl 2-chloro-1-(4-fluorobenzyl)-1H-imidazole-5-carboxylate (h-3) (amount, 0.96 g; yield, 52%).

(3) A solution of the foregoing compound (h-3) (0.96 g, 3.6 mmol) and 1,3-dibromo-5,5-dimethylimidazoline-2,4-dione (1.0 g, 3.6 mmol) in DMF (7.0 mL) was stirred overnight at 60° C. To the stirred solution, 1,3-dibromo-5,5-dimethylimidazoline-2,4-dione (1.0 g, 3.6 mmol) was further added and the resulting mixture was stirred for 4 hours. To the reaction mixture, a saturated aqueous solution of sodium thiosulfate and a saturated aqueous solution of sodium hydrogencarbonate were added and extraction was conducted with ethyl acetate; the organic layer was washed with water and saturated brine and then dried over anhydrous sodium sulfate. The solvents in the organic layer were distilled off under reduced pressure and the residue was purified by silica gel column chromatography (n-hexane:ethyl acetate=90:10~50:50) to give methyl 4-bromo-2-chloro-1-(4-fluorobenzyl)-1H-imidazole-5-carboxylate (h-4) (amount, 0.82 g; yield, 66%).

(4) A solution of the foregoing compound (h-4) (0.66 g, 1.9 mmol), copper iodide (36 mg, 0.19 mmol) and triethylamine (3.3 mL, 24 mmol) in DMF (10 mL) was degassed and, thereafter, dichlorobis(triphenylphosphine)palladium (66 mg, 0.094 mmol) and 2-methyl-3-butyn-2-ol (0.55 mL, 5.7 mmol) were added sequentially and the resulting mixture was stirred overnight at 60° C. in an argon atmosphere. To the stirred solution, water and ethyl acetate were added and the resulting mixture was filtered through Celite; the organic layer in the filtrate was washed with saturated brine and then dried over anhydrous sodium sulfate. The solvents in the organic layer were distilled off under reduced pressure and the residue was purified by silica gel column chromatography (n-hexane:ethyl acetate=70:30~30:70) to give methyl 2-chloro-1-(4-fluorobenzyl)-4-(3-hydroxy-3-methyl-1-butyn-1-yl)-1H-imidazole-5-carboxylate (h-5) (amount, 0.45 g; yield, 68%).

(5) To a solution of the foregoing compound (h-5) (0.45 g, 1.3 mmol) in methanol (8.5 mL), MsOH (0.41 mL, 6.3 mmol) was added and the resulting mixture was stirred at 60° C. for 2 hours. To the reaction mixture, a saturated aqueous solution of sodium hydrogencarbonate was added and after extraction with chloroform, the organic layer was dried over anhydrous sodium sulfate. The solvents in the organic layer were distilled off under reduced pressure and the residue was purified by silica gel column chromatography (n-hexane:ethyl acetate=90:10~50:50) to give methyl 2-chloro-1-(4-fluorobenzyl)-4-(3-methoxy-3-methyl-1-butyn-1-yl)-1H-imidazole-5-carboxylate (h-6) (amount, 0.34 g; yield, 73%).

(6) To a solution of the foregoing compound (h-6) (0.34 g, 0.94 mmol) in a solvent mixture of THF (3.5 mL) and methanol (3.5 mL), an aqueous solution (1.4 mL, 2.8 mmol) of 2 mol/L sodium hydroxide was added dropwise and the resulting mixture was stirred at room temperature for 2 hours. To the reaction mixture, 2 mol/L hydrochloric acid was added for neutralization and thereafter the solvents were distilled off under reduced pressure; to the residue, chloroform and water were added and the organic layer was dried over anhydrous sodium sulfate. The solvents in the organic layer were distilled off under reduced pressure to give 2-chloro-1-(4-fluorobenzyl)-4-(3-methoxy-3-methyl-1-butyn-1-yl)-1H-imidazole-5-carboxylic acid (h-7) (amount, 0.35 g; yield, 100%).

(7) To a solution of the foregoing compound (h-7) (0.12 g, 0.33 mmol) and methyl 4-aminomethylbenzoate hydrochloride (f-5) (67 mg, 0.33 mmol) in DMF (1.5 mL), DIPEA (0.15 mL, 0.83 mmol) was added dropwise and then HATU (0.14 g, 0.37 mmol) was added and the resulting mixture was stirred overnight room temperature. To the reaction mixture, water was added and extraction was conducted with ethyl acetate; the organic layer was washed with saturated brine and then dried over anhydrous sodium sulfate. The solvents in the organic layer were distilled off under reduced pressure and the residue was purified by silica gel column chromatography (n-hexane:ethyl acetate=70:30~30:70) to give methyl 4-{[2-chloro-1-(4-fluorobenzyl)-4-(3-methoxy-3-methyl-1-butyn-1-yl)-1H-imidazole-5-carboxamido]methyl}benzoate (h-8) (amount, 0.10 g; yield, 63%).

(8) To a solution of the foregoing compound (h-8) (4.8 g, 9.6 mmol) in a solvent mixture of THF (24 mL) and methanol (24 mL), an aqueous solution (24 mL, 96 mmol) of 4 mol/L sodium hydroxide was added dropwise and the resulting mixture was stirred at room temperature for 5 hours. To the reaction mixture, 3 mol/L hydrochloric acid was added for neutralization and thereafter the precipitating solids were recovered by filtration to give 4-{[2-chloro-1-(4-fluorobenzyl)-4-(3-methoxy-3-methyl-1-butyn-1-yl)-1H-imidazole-5-carboxamido]methyl}benzoic acid (Compound 56) (amount, 4.3 g; yield, 93%). The structural formula of Compound 56 and the data on its properties will be shown later in Table 1.

(9) In the same way as Example 10, Compounds 48~55 and 57 also listed later in Table 1 were produced from the respectively corresponding starting materials. Also in the same way as Example 10, Compounds 58 and 59 also listed later in Table 1 were produced from the respectively corresponding starting materials, provided that the reaction for converting a hydroxyl group to a methoxy group as from compound (h-5) to compound (h-6) was not carried out.

Example 11

4-(1-{2-Chloro-4-(3-methoxy-3-methyl-1-butyn-1-yl)-1-[4-(trifluoromethyl)benzyl]-1H-imidazole-5-carboxamido}cyclopropyl)benzoic acid (Compound 42)

Compound 42 was produced according to the reaction scheme depicted below:

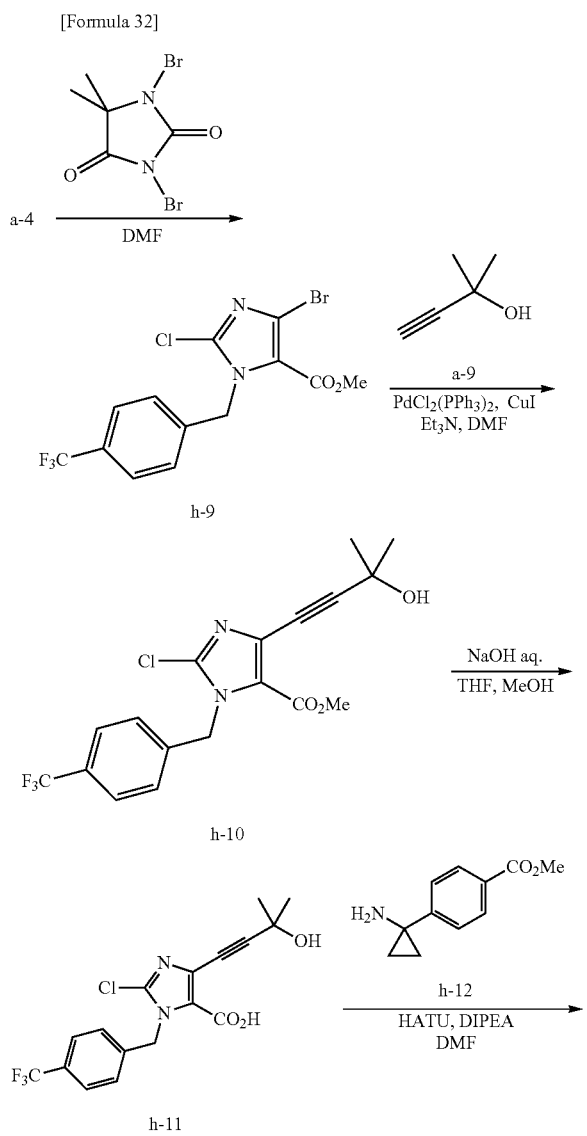

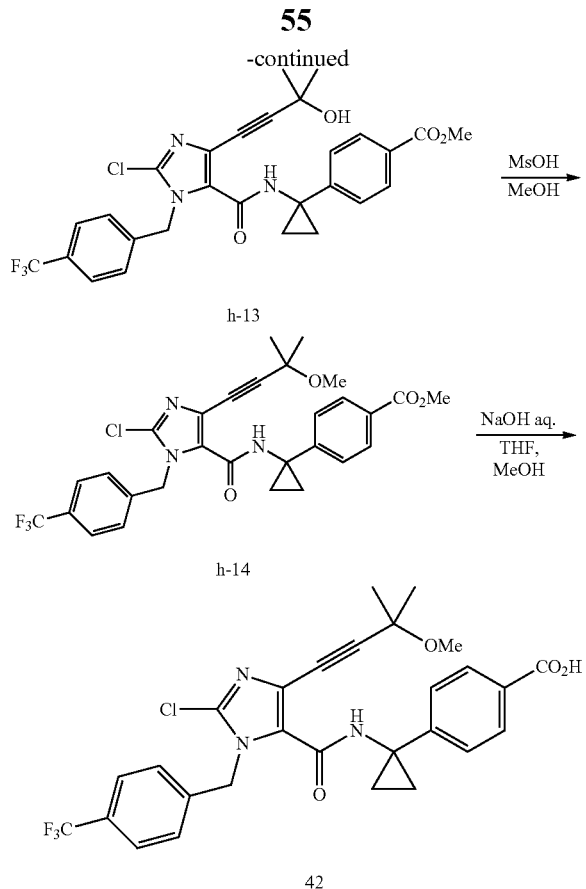

(1) A solution in DMF (42 mL) of compound (a-4) (4.0 g, 13 mmol) as obtained by the method of Example 1 and 1,3-dibromo-5,5-dimethylimidazoline-2,4-dione (7.2 g, 25 mmol) was stirred at 60° C. for 12 hours. To the stirred solution, 1,3-dibromo-5,5-dimethylimidazoline-2,4-dione (3.6 g, 13 mmol) was further added and the resulting mixture was stirred at 60° C. for 6 hours. To the stirred solution, a saturated aqueous solution of sodium thiosulfate and a saturated aqueous solution of sodium hydrogencarbonate were added and extraction was conducted with ethyl acetate; the organic layer was washed with water and saturated brine and then dried over anhydrous sodium sulfate. The solvents in the organic layer were distilled off under reduced pressure and the residue was purified by silica gel column chromatography (n-hexane:ethyl acetate=97:3~76:24) to give methyl 4-bromo-2-chloro-1-[4-(trifluoromethyl)benzyl]-1H-imidazole-5-carboxylate (h-9) (amount, 3.9 g; yield, 79%).

(2) A solution of the foregoing compound (h-9) (0.30 g, 0.77 mmol), copper iodide (14 mg, 0.075 mmol) and triethylamine (1.5 mL, 11 mmol) in DMF (4.5 mL) was degassed and, thereafter, dichlorobis(triphenylphosphine)palladium (53 mg, 0.075 mmol) and 2-methyl-3-butyn-2-ol (a-9) (0.22 mL, 2.3 mmol) were sequentially added and the resulting mixture was stirred overnight at 60° C. in an argon atmosphere. To the stirred solution, water and ethyl acetate were added and the resulting mixture was filtered through Celite; the organic layer in the filtrate was washed with saturated brine and then dried over anhydrous sodium sulfate. The solvents in the organic layer were distilled off under reduced pressure and the residue was purified by silica gel column chromatography (n-hexane:ethyl acetate=90:10~30:70) to give methyl 2-chloro-4-(3-hydroxy-3-methyl-1-butyn-1-yl)-1-[4-(trifluoromethyl)benzyl]-1H-imidazole-5-carboxylate (h-10) (amount, 0.22 g; yield, 72%).

(3) To a solution of the foregoing compound (h-10) (0.22 g, 0.55 mmol) in a solvent mixture of THF (2 mL) and methanol (2 mL), an aqueous solution (0.55 mL, 1.1 mmol) of 2 mol/L sodium hydroxide was added dropwise and the resulting mixture was stirred at room temperature for an hour. To the reaction mixture, 2 mol/L hydrochloric acid was added for neutralization and thereafter the solvents were distilled off under reduced pressure; to the residue, chloroform and water were added and the organic layer was dried over anhydrous sodium sulfate. The solvents in the organic layer were distilled off under reduced pressure to give 2-chloro-4-(3-hydroxy-3-methyl-1-butyn-1-yl)-1-[4-(trifluoromethyl)benzyl]-1H-imidazole-5-carboxylic acid (h-11) (amount, 0.21 g, yield, 100%).

(4) To a solution of the foregoing compound (h-11) (0.21 g, 0.55 mmol) and methyl 4-(1-aminocyclopropyl)benzoate (h-12) (0.12 g, 0.60 mmol) in DMF (3.2 mL), DIPEA (0.24 mL, 1.4 mmol) was added dropwise and, thereafter, HATU (0.23 g, 0.60 mmol) was added and the resulting mixture was stirred overnight at room temperature. To the reaction mixture, water was added and extraction was conducted with ethyl acetate; the organic layer was washed with saturated brine and then dried over anhydrous sodium sulfate. The solvents in the organic layer were distilled off under reduced pressure and the residue was purified by silica gel column chromatography (n-hexane:ethyl acetate=70:30~0:100) to give methyl 4-(1-{2-chloro-4-(3-hydroxy-3-methyl-1-butyn-1-yl)-1-[4-(trifluoromethyl)benzyl]-1H-imidazole-5-carboxamido}cyclopropyl)benzoate (h-13) (amount, 0.26 g; yield, 84%).

(5) To a solution of the foregoing compound (h-13) (98 mg, 0.18 mmol) in methanol (2 mL), MsOH (0.057 mL, 0.88 mmol) was added and the resulting mixture was stirred overnight at 60° C. To the reaction mixture, a saturated aqueous solution of sodium hydrogencarbonate was added and after extraction with chloroform, the organic layer was dried over anhydrous sodium sulfate. The solvents in the organic layer were distilled off under reduced pressure and the residue was purified by silica gel column chromatography (n-hexane:ethyl acetate=70:30~30:70) to give methyl 4-(1-{2-chloro-4-(3-methoxy-3-methyl-1-butyn-1-yl)-1-[4-(trifluoromethyl)benzyl]-1H-imidazole-5-carboxamido}cyclopropyl)benzoate (h-14) (amount, 96 mg; yield, 95%).

(6) To a solution of the foregoing compound (h-14) (96 mg, 0.17 mmol) in a solvent mixture of THF (1 mL) and methanol (1 mL), an aqueous solution (0.25 mL, 0.50 mmol) of 2 mol/L sodium hydroxide was added dropwise and the resulting mixture was stirred at 50° C. for 2 hours. To the reaction mixture, 1 mol/L hydrochloric acid was added for neutralization and, thereafter, ethyl acetate was added and the organic layer was dried over anhydrous sodium sulfate. The solvents in the organic layer were distilled off under reduced pressure and purification by silica gel column chromatography (chloroform:methanol=98:2~90:10) gave 4-(1-{2-chloro-4-(3-methoxy-3-methyl-1-butyn-1-yl)-1-[4-(trifluoromethyl)benzyl]-1H-imidazole-5-carboxamido cyclopropyl}benzoic acid (Compound 42) (amount, 58 mg; yield, 62%). The structural formula of Compound 42 and the data on its properties will be shown later in Table 1.

Example 12

4-(1-{2-Chloro-4-(3-methoxy-3-methyl-1-butyn-1-yl)-1-(4-methylbenzyl)-1H-imidazole-5-carboxamido}cyclopropyl)benzoic acid (Compound 67)

Compound 67 was produced according to the reaction scheme depicted below:

[Formula 33]

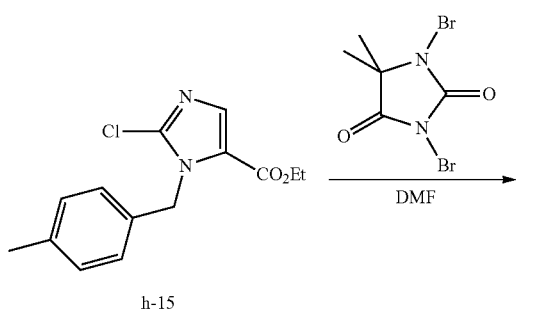

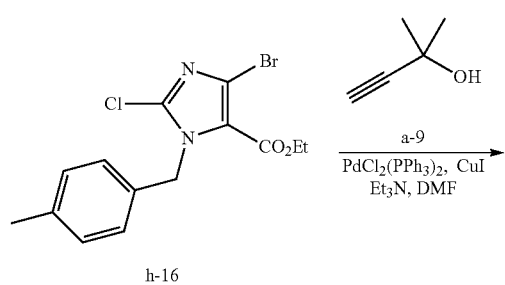

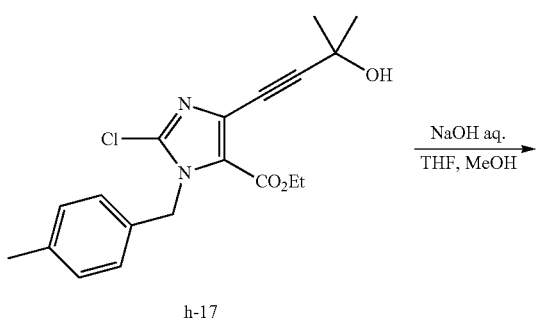

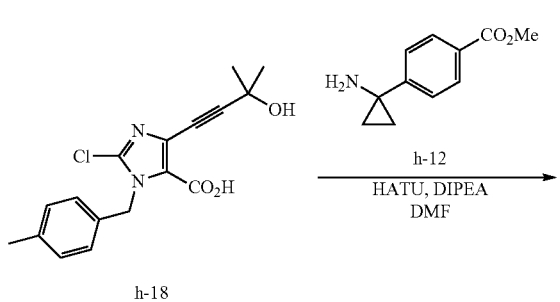

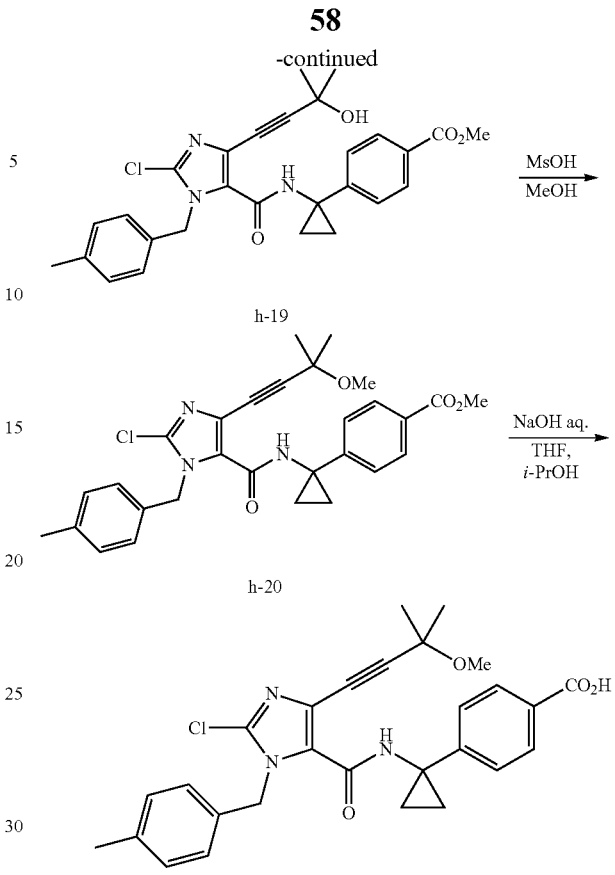

(1) A solution of ethyl 2-chloro-1-(4-methylbenzyl)-1H-imidazole-5-carboxylate (h-15) (7.5 g, 27 mmol) and 1,3-dibromo-5,5-dimethylimidazoline-2,4-dione (20 g, 67 mmol) in DMF (67 mL) was stirred at 60° C. for 5 hours. To the stirred solution, a saturated aqueous solution of sodium thiosulfate and a saturated aqueous solution of sodium hydrogencarbonate were added and extraction was conducted with ethyl acetate; the organic layer was washed with water and saturated brine and then dried over anhydrous sodium sulfate. The solvents in the organic layer were distilled off under reduced pressure and the residue was purified by silica gel column chromatography (n-hexane:ethyl acetate=2:1) to give ethyl 4-bromo-2-chloro-1-(4-methylbenzyl)-1H-imidazole-5-carboxylate (h-16) (amount, 5.6 g; yield, 58%).

(2) A solution of the foregoing compound (h-16) (5.5 g, 15 mmol), copper iodide (29 mg, 0.15 mmol) and triethylamine (32 mL, 230 mmol) in DMF (0.65 mL) was degassed and, thereafter, dichlorobis(triphenylphosphine)palladium (0.22 g, 0.31 mmol) and 2-methyl-3-butyn-2-ol (a-9) (3.0 mL, 31 mmol) were sequentially added and the resulting mixture was stirred at 90° C. for 20 hours in an argon atmosphere. To the stirred mixture, a saturated aqueous solution of sodium hydrogencarbonate was added and extraction was conducted with ethyl acetate; the organic layer was washed with water and saturated brine and then dried over anhydrous sodium sulfate. The solvents in the organic layer were distilled off under reduced pressure and the residue was purified by silica gel column chromatography (n-hexane:ethyl acetate=2:1) to give ethyl 2-chloro-4-(3-hydroxy-3-methyl-1-butyn-1-yl)-1-(4-methylbenzyl)-1H-imidazole-5-carboxylate (h-17) (amount, 4.2 g; yield, 75%).

(3) To a solution of the foregoing compound (h-17) (4.1 g, 11 mmol) in a solvent mixture of THF (16 mL) and methanol (16 mL), an aqueous solution (14 mL, 57 mmol) of 4 mol/L sodium hydroxide was added dropwise and the resulting mixture was stirred at room temperature for 2 hours. To the reaction mixture, 2 mol/L hydrochloric acid was added for neutralization and the precipitating solids were recovered by filtration to give 2-chloro-4-(3-hydroxy-3-methyl-1-butyn-1-yl)-1-(4-methylbenzyl)-1H-imidazole-5-carboxylic acid (h-18) (amount, 3.8 g; yield, 100%).

(4) To a solution of the foregoing compound (h-18) (3.0 g, 8.9 mmol) and methyl 4-(1-aminocyclopropyl)benzoate (h-12) (2.0 g, 11 mmol) in DMF (22 mL), DIPEA (3.9 mL, 22 mmol) was added dropwise; thereafter, HATU (3.7 g, 9.8 mmol) was added and the resulting mixture was stirred overnight at room temperature. The reaction mixture was added to water and thereafter the precipitating solids were recovered by filtration to give methyl 4-(1-{2-chloro-4-(3-hydroxy-3-methyl-1-butyn-1-yl)-1-(4-methylbenzyl)-1H-imidazole-5-carboxamido}cyclopropyl)benzoate (h-19) (amount, 4.2 g; yield, 93%).

(5) To a solution of the foregoing compound (h-19) (4.1 g, 8.1 mmol) in methanol (20 mL), MsOH (2.6 mL, 40 mmol) was added and the resulting mixture was stirred at 60° C. for 5 hours. The reaction mixture was added to a saturated aqueous solution of sodium hydrogencarbonate and the precipitating solids were recovered by filtration; thereafter, purification was conducted by silica gel column chromatography (n-hexane:ethyl acetate=1:1), giving methyl 4-(1-{2-chloro-4-(3-methoxy-3-methyl-1-butyn-1-yl)-1-(4-methylbenzyl)-1H-imidazole-5-carboxamido}cyclopropyl)benzoate (h-20) (amount, 3.3 g; yield, 78%).

(6) To a solution of the foregoing compound (h-20) (3.3 g, 6.3 mmol) in a solvent mixture of THF (9 mL) and isopropanol (9 mL), an aqueous solution (7.8 mL, 31 mmol) of 4 mol/L sodium hydroxide was added dropwise and the resulting mixture was stirred at 90° C. for 5 hours. To the reaction mixture, 2 mol/L hydrochloric acid was added and the precipitating solids were recovered by filtration; thereafter, purification was conducted by silica gel column chromatography (chloroform:methanol=10:1), giving 4-(1-{2-chloro-4-(3-methoxy-3-methyl-1-butyn-1-yl)-1-(4-methylbenzyl)-1H-imidazole-5-carboxamido}cyclopropyl) benzoic acid (Compound 67) (amount, 2.1 g; yield, 67%). The structural formula of Compound 67 and the data on its properties will be shown later in Table 1.

(7) Compound (h-19) was hydrolyzed by the same method as in (6) of Example 12, yielding Compound 68 identified later in Table 1.

Example 13 trans-4-({1-[2-(4-Chlorophenoxy)ethyl]-2-(difluoromethyl)-4-(3-methoxy-3-methyl-1-butyn-1-yl)-1H-imidazole-5-carboxamido}methyl)cyclohexanecarboxylic acid (Compound 63)

After making compound (i-5) according to the reaction scheme depicted below, the same procedures as described in Examples 1~3 were employed to produce Compound 63.

[Formula 34]

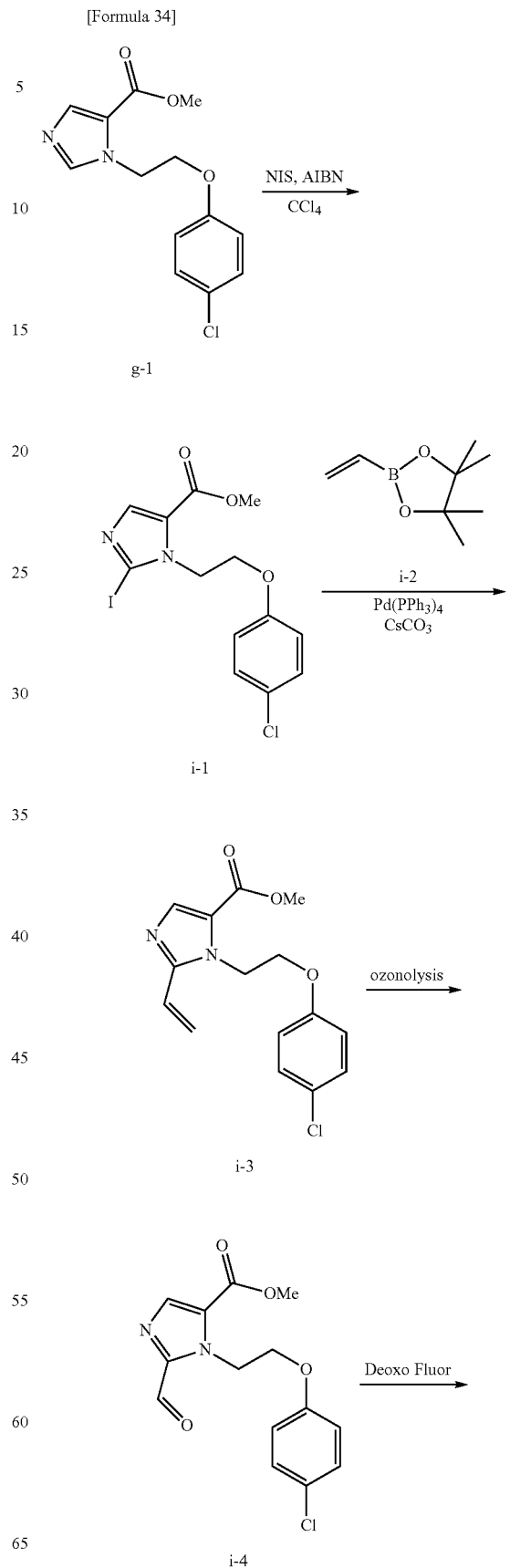

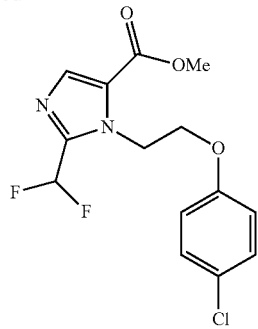

i-5

(1) To a solution in carbon tetrachloride (150 mL) of methyl 1-[2-(4-chlorophenoxy)ethyl]-1H-imidazole-5-carboxylate (g-1) (4.1 g, 15 mmol) as obtained in the same way as Examples 1~3, NIS (3.3 g, 15 mmol) and 2,2'-azobis (isobutyronitrile) (0.12 g, 0.73 mmol) were added and the resulting mixture was stirred overnight at 60° C. The reaction mixture was sequentially washed with a saturated aqueous solution of sodium hydrogencarbonate and a saturated aqueous solution of sodium thiosulfate; after extraction with ethyl acetate, the organic layer was dried over anhydrous sodium sulfate. The solvents in the organic layer were distilled off under reduced pressure and the residue was purified by silica gel column chromatography (n-hexane: ethyl acetate=1:1) to give methyl 1-[2-(4-chlorophenoxy) ethyl]-2-iodo-1H-imidazole-5-carboxylate (i-1) (amount, 3.7 g; yield, 62%).

(2) To a solution of the foregoing compound (i-1) (0.50 g, 1.2 mmol) in a solvent mixture of 1,4-dioxane (9.0 mL) and water (2.0 mL), vinylboronic acid pinacol ester (i-2) (0.63 mL, 3.7 mmol) was added and thereafter the reaction mixture was degassed. To the reaction mixture, tetrakis (triphenylphosphine)palladium (0.14 g, 0.12 mmol) and cesium carbonate (1.2 g, 3.7 mmol) were added and the resulting mixture was stirred at 110° C. for 30 minutes in a fused tube under microwave irradiation. To the reaction mixture, water was added and extraction was conducted with ethyl acetate; the organic layer was washed with water and then dried over anhydrous sodium sulfate. The solvents in the organic layer were distilled off under reduced pressure and the residue was purified by silica gel column chromatography (n-hexane:ethyl acetate=1:1) to give methyl 1-[2-(4-chlorophenoxy)ethyl]-2-vinyl-1H-imidazole-5-carboxylate (i-3) (amount, 0.16 mg; yield, 42%).

(3) A solution of the foregoing compound (i-3) (80 mg, 0.26 mmol) in a solvent mixture of dichloromethane (1.3 mL) and methanol (1.3 mL) was bubbled with ozone for an hour under stirring at −78° C. To the reaction mixture, dimethyl sulfide (96 μL) was added and then the mixture was brought to room temperature and stirred for an additional 3 hours. The solvents were distilled off under reduced pressure and the residue was purified by silica gel column chromatography (n-hexane:ethyl acetate=1:1) to give methyl 1-[2-(4-chlorophenoxy)ethyl]-2-formyl-1H-imidazole-5-carboxylate (i-4) (amount, 74 mg; yield, 92%).

(4) A solution of the foregoing compound (i-4) (50 mg, 0.16 mmol) in dichloromethane (0.81 mL) was cooled to 0° C. To the cooled solution, ethanol (5 μL) and bis(2-methoxyethyl)aminosulfate trifluoride (Deoxo Fluor®) (36 μL, 0.19 mmol) were added and the resulting mixture was stirred at 0° C. for 3 hours. To the reaction mixture, water was added and extraction was conducted with chloroform; the organic layer was washed with water and then dried over anhydrous sodium sulfate. The solvents in the organic layer were distilled off under reduced pressure and the residue was purified by silica gel column chromatography (n-hexane: ethyl acetate=1:1) to give methyl 1-[2-(4-chlorophenoxy) ethyl]-2-(difluoromethyl)-1H-imidazole-5-carboxylate (i-5) (amount, 45 mg; yield, 84%).

(5) Compound 63 was obtained by the same methods as in Examples 1~3 and Example 4, except that compound (a-4) was replaced by compound (i-5).

Compound 64 was obtained by the same methods as in Examples 1~3 and Example 4, except that compound (a-4) was replaced by compound (i-5), and compound (a-6) by compound (f-5). The structural formulas of Compounds 63 and 64 and the data on their properties will be shown later in Table 1.

Example 14 trans-4-({2-Chloro-1-[4-(difluoromethyl)benzyl]-4-(3-methoxy-3-methyl-1-butyn-1-yl)-1H-imidazole-5-carboxamido}methyl)cyclohexanecarboxylic acid (Compound 60)

After synthesizing [4-(difluoromethyl)phenyl]methanol (j-3) according to the reaction scheme depicted below, the same production method as described in Example 10 was applied to produce Compound 60.

[Formula 35]

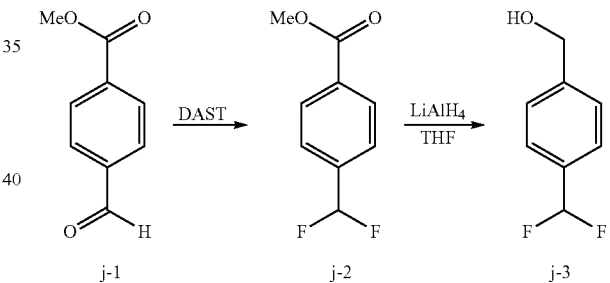

Described below is the method for producing [4-(difluoromethyl)phenyl]methanol (j-3).

(1) A solution of methyl 4-formylbenzoate (j-1) (0.90 g, 5.5 mmol) in (diethylamino)sulfate trifluoride (DAST) (3.6 mL, 27 mmol) was stirred overnight at room temperature. The reaction mixture was cooled to 0° C. and water was added dropwise. Extraction was conducted with ethyl acetate and the organic layer was washed with water and then dried over anhydrous sodium sulfate. The solvents in the organic layer were distilled off under reduced pressure and the residue was purified by silica gel column chromatography (n-hexane:ethyl acetate=1:1) to give methyl 4-(difluoromethyl)benzoate (j-2) (amount, 0.98 g; yield, 96%).

(2) A solution of the foregoing compound (j-2) (1.0 g, 5.4 mmol) in THF (27 mL) was cooled to 0° C. To the cooled solution, lithium aluminum hydride (0.20 g, 5.4 mmol) was added and the resulting mixture was stirred overnight at room temperature. To the reaction mixture, anhydrous sodium sulfate was added, followed by filtration through Celite. The solvent in the filtrate was distilled off under reduced pressure to give [4-(difluoromethyl)phenyl]methanol (j-3) (amount, 0.60 g; yield, 70%).

(3) Compound 60 was obtained by the same method as Example 10, except that compound (h-1) was replaced by compound (j-3), and compound (f-5) by compound (a-6). The structural formula of Compound 60 and the data on its properties will be shown later in Table 1.

Example 15

Trans-4-({2-chloro-1-[2-(4-chlorophenoxy)ethyl]-4-(4-hydroxy-3,3-dimethyl-1-butyn-1-yl)-1H-imidazole-5-carboxamido}methyl)cyclohexanecarboxylic acid (Compound 61)

(1) 1-{[2,2-Dimethyl-3-butyn-1-yl]oxy]methyl}-4-methoxybenzene (Compound k-4)

Compound (k-4) was produced according to the reaction scheme depicted below:

[Formula 36]

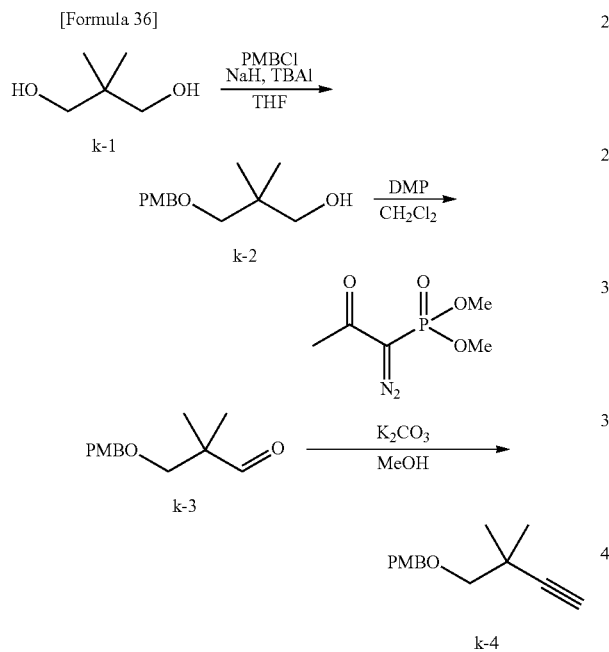

(2) A solution of 2,2-dimethylpropane-1,3-diol (k-1) (1.0 g, 9.6 mmol) in THF (120 mL) was cooled to 0° C. and after adding sodium hydride (60% in oil, 0.38 g, 9.6 mmol), the resulting mixture was stirred at 0° C. for 50 minutes. Then, tetra-n-butylammonium iodide (3.6 g, 120 mmol) and p-methoxybenzyl chloride (PMBCl) (1.5 g, 9.6 mmol) were sequentially added, followed by stirring at room temperature for 6 hours. To the reaction mixture, a saturated aqueous solution of ammonium chloride was added and extraction was conducted with ethyl acetate; thereafter, the solvents in the organic layer were distilled off under reduced pressure and the residue was purified by silica gel column chromatography (n-hexane:ethyl acetate=70:30~0:100) to give 3-[(4-mehoxybenzyl)oxy]-2,2-dimethylpropane-1-ol (k-2) (amount, 1.5 g; yield, 70%).

(3) To a solution of the foregoing compound (k-2) (1.5 g, 6.7 mmol) in dichloromethane (33 mL), Dess-Martin periodinane (3.4 g, 8.0 mmol) was added under ice cooling and the resulting mixture was stirred at room temperature for 4 hours. To the reaction mixture, saturated sodium thiosulfate was added and after extraction with ethyl acetate, the organic layer was dried over anhydrous sodium sulfate. The solvents in the organic layer were distilled off under reduced pressure and the residue was purified by silica gel column chromatography (n-hexane:ethyl acetate=80:20~20:80) to give 3-[(4-methoxybenzyl)oxy]-2,2-dimethylpropanal (k-3) (amount, 1.4 g; yield, 95%).

(4) To a solution of the foregoing compound (k-3) (0.70 g, 3.2 mmol) in methanol (13 mL), potassium carbonate (1.3 g, 9.5 mmol) and dimethyl (1-diazo-2-oxopropyl)phosphonate (0.66 mL, 4.4 mmol) were added and the resulting mixture was stirred at room temperature for 2 hours. To the reaction mixture, ethyl acetate was added and the organic layer was successively washed with water and saturated brine and then dried over anhydrous sodium sulfate. The solvents in the organic layer were distilled off under reduced pressure and the residue was purified by silica column chromatography (n-hexane:ethyl acetate=80:20~20:80) to give 1-{[2,2-dimethyl-3-butyn-1-yl]oxy]methyl}-4-methoxybenzene (k-4) (amount, 0.66 g; yield, 95%).

(5) Methyl trans-4-({2-chloro-1-[2-(4-chlorophenoxy)ethyl]-4-(4-hydroxy-3,3-dimethyl-1-butyn-1-yl)-1H-imidazole-5-carboxamido}methyl)cyclohexanecarboxylate (Compound k-6)

Using the foregoing compound (k-4), the same method as Example 1 was applied to produce methyl trans-4-[(2-chloro-1-[2-(4-chlorophenoxy)ethyl]-4-{4-[(4-methoxybenzyl)oxy]-3,3-dimethyl-1-butyn-1-yl}-1H-imidazole-5-carboxamido)methyl]cyclohexanecarboxylate (k-5). Subsequently, in accordance with the reaction scheme depicted below, the p-methoxybenzyl group was removed from the foregoing compound (k-5) to thereby produce compound (k-6):

[Formula 37]

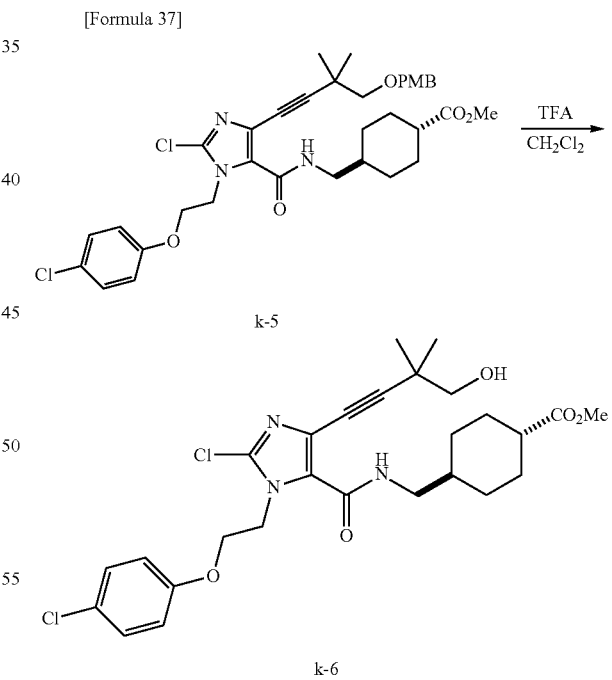

(6) To a solution of the foregoing compound (k-5) (0.14 g, 0.22 mmol) in dichloromethane (2.1 mL), TFA (0.17 mL, 2.2 mmol) was added dropwise and the resulting mixture was stirred at room temperature for 4 hours. To the reaction mixture, a saturated aqueous solution of sodium hydrogencarbonate was added for neutralization and, thereafter, chloroform was added and the organic layer was dried over anhydrous sodium sulfate. The solvents in the organic layer were distilled off under reduced pressure to give methyl trans-4-({2-chloro-1-[2-(4-chlorophenoxy)ethyl]-4-(4-hydroxy-3,3-dimethyl-1-butyn-1-yl)-1H-imidazole-5-carboxamido}methyl)cyclohexanecarboxylate (k-6) (amount, 83 mg; yield, 70%).

(7) In the same way as Example 1(7), Compound (k-6) was hydrolyzed to produce Compound 61.

Also in the same way as Example 15, Compound 65 was produced from the corresponding starting material. The structural formulas of Compounds 61 and 65 and the data on their properties will be shown later in Table 1.

Example 16 trans-4-({2-Chloro-1-[2-(4-chlorophenoxy)ethyl]-4-(4-methoxy-3,3-dimethyl-1-butyn-1-yl)-1H-imidazole-5-carboxamido}methyl)cyclohexanecarboxylate (Compound 62)

Compound (k-6) synthesized in Example 15 was processed in accordance with the reaction scheme depicted below, producing methyl trans-4-({2-chloro-1-[2-(4-chlorophenoxy)ethyl]-4-(4-methoxy-3,3-dimethyl-1-butyn-1-yl)-1H-imidazole-5-carboxamido}methyl)cyclohexanecarboxylate (Compound k-7):

[Formula 38]

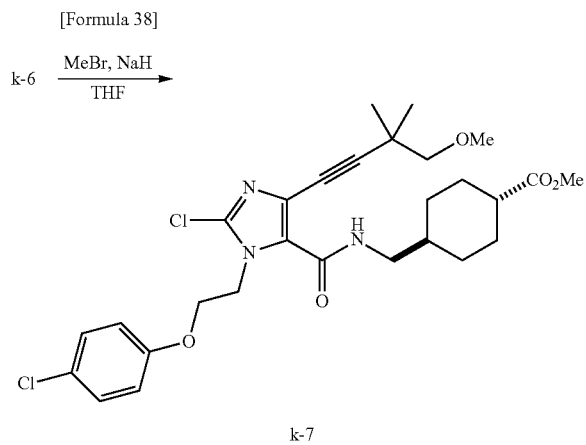

(1) To a solution of the foregoing compound (k-6) (0.14 g, 0.25 mmol) in THF (2.4 mL), sodium hydride (60% in oil, 21 mg, 0.52 mmol) was added and the resulting mixture was stirred at 0° C. for 30 minutes; thereafter, bromomethane (0.18 mL, 0.37 mmol) was added to the reaction mixture which was then stirred at room temperature for 4 hours. To the reaction mixture, a saturated aqueous solution of ammonium chloride and chloroform were added and the organic layer was dried over anhydrous sodium sulfate. The solvents in the organic layer were distilled off under reduced pressure to give methyl trans-4-({2-chloro-1-[2-(4-chlorophenoxy)ethyl]-4-(4-methoxy-3,3-dimethyl-1-butyn-1-yl)-1H-imidazole-5-carboxamido}methyl)cyclohexanecarboxylate (k-7) (amount, 25 mg; yield, 18%).

(2) In the same way as Example 1(7), compound (k-7) was hydrolyzed to produce Compound 62. The structural formula of Compound 62 and the data on its properties will be shown later in Table 1.

Example 17

6-({2-Chloro-4-(3-hydroxy-3-methyl-1-butyn-1-yl)-1-[4-(trifluoromethyl)benzyl]-1H-imidazole-5-carboxamido}methyl)nicotinic acid (Compound 6)

Methyl 6-(aminomethyl)nicotinate hydrochloride (l-2) was produced according to the reaction scheme depicted below:

[Formula 39]

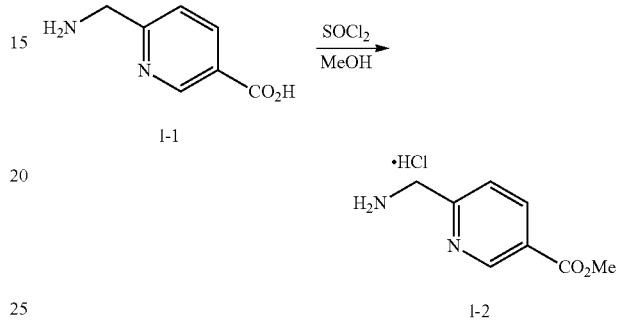

(1) To a solution of 6-(aminomethyl)nicotinic acid (l-1) (201 mg, 1.32 mmol) in methanol (5.0 mL), thionyl chloride (0.950 mL, 13.2 mmol) was added and the resulting mixture was stirred overnight at 70° C. The solvent was distilled off under reduced pressure to give methyl 6-(aminomethyl)nicotinate hydrochloride (l-2) as a crude product.

(2) Compound 6 was produced by the same method as in Examples 1~3, except that compound (a-6) was replaced by compound (l-2). The structural formula of Compound 6 and the data on its properties will be shown later in Table 1.

Example 18 trans-4-({2-Chloro-4-(3-hydroxy-3-methyl-1-butyn-1-yl)-1-[4-(trifluoromethyl)benzyl]-1H-imidazole-5-carboxamido}methyl)-1-(2H-tetrazol-5-yl)cyclohexane (Compound 8)

(1) Trans-4-(2H-tetrazol-5-yl)cyclohexylmethanamine hydrochloride (m-3)

Compound (m-3) was produced according to the reaction scheme depicted below:

[Formula 40]

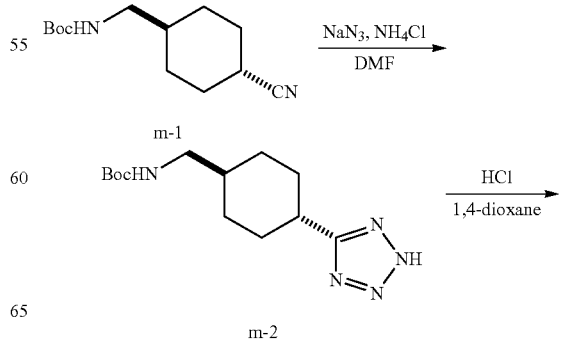

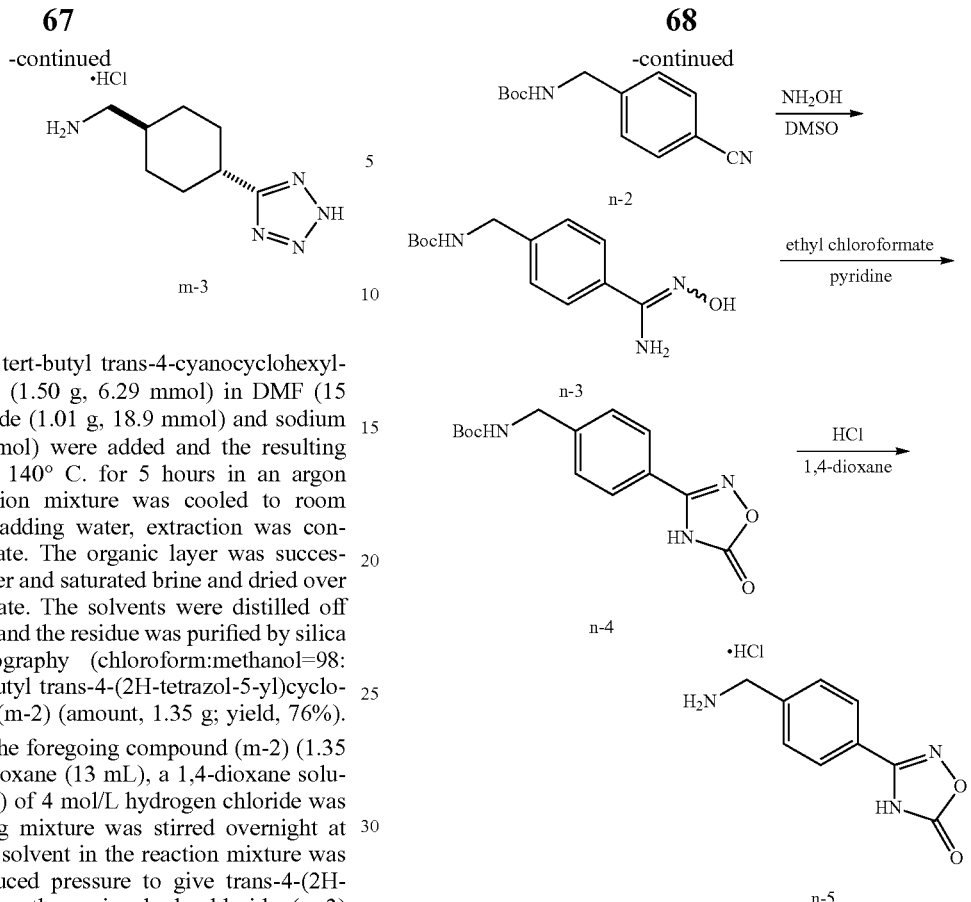

(1) To a solution of tert-butyl trans-4-cyanocyclohexyl-methylcarbamate (m-1) (1.50 g, 6.29 mmol) in DMF (15 mL), ammonium chloride (1.01 g, 18.9 mmol) and sodium azide (1.23 g, 18.9 mmol) were added and the resulting mixture was stirred at 140° C. for 5 hours in an argon atmosphere. The reaction mixture was cooled to room temperature and after adding water, extraction was conducted with ethyl acetate. The organic layer was successively washed with water and saturated brine and dried over anhydrous sodium sulfate. The solvents were distilled off under reduced pressure and the residue was purified by silica gel column chromatography (chloroform:methanol=98:2~90:10) to give tert-butyl trans-4-(2H-tetrazol-5-yl)cyclo-hexylmethylcarbamate (m-2) (amount, 1.35 g; yield, 76%).

(2) To a solution of the foregoing compound (m-2) (1.35 g, 4.80 mmol) in 1,4-dioxane (13 mL), a 1,4-dioxane solution (40 mL, 160 mmol) of 4 mol/L hydrogen chloride was added and the resulting mixture was stirred overnight at room temperature. The solvent in the reaction mixture was distilled off under reduced pressure to give trans-4-(2H-tetrazol-5-yl)cyclohexylmethanamine hydrochloride (m-3) (amount, 1.09 g; yield, 100%).

(3) Compound 8 was produced by the same method as in Example 1, except that compound (a-6) was replaced by the foregoing compound (m-3).

Also Compound 7 was produced by the same method as in Example 1, except that 4-(2H-tetrazol-5-yl)phenylmethanamine hydrochloride prepared in the same way as compound (m-3) was substituted for compound (a-6). The structural formulas of these Compounds 7 and 8 and the data on their properties will be shown later in Table 1.

Example 19

3-[4-({2-Chloro-4-(3-hydroxy-3-methyl-1-butyn-1-yl)-1-[4-(trifluoromethyl)benzyl]-1H-imidazole-5-carboxamido}methyl)-phenyl]-1,2,4-oxadiazol-5(4H)-one (Compound 9)

3-[4-(Aminomethyl)phenyl]-1,2,4-oxadiazol-5(4H)-one hydrochloride (n-5) was produced according to the reaction scheme depicted below:

[Formula 41]

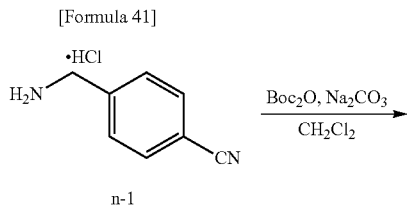

(1) To a solution of 4-aminomethylbenzonitrile hydrochloride (n-1) (5.00 g, 29.7 mmol) in dichloromethane (167 mL), sodium carbonate (7.54 g, 71.2 mmol) was added. The reaction mixture was cooled to 0° C. and di-tert-butyl dicarbonate (7.57 mL, 32.6 mmol) was added; the resulting mixture was brought to room temperature at which it was stirred overnight. To the reaction mixture, water was added and extraction was conducted with ethyl acetate. The organic layer was successively washed with water and saturated brine and dried over anhydrous sodium sulfate. The solvents were distilled off under reduced pressure and the residue was purified by silica gel (NH) column chromatography (n-hexane:ethyl acetate=1:1) to give tert-butyl 4-cyanobenzylcarbamate (n-2) (amount, 6.48 g; yield, 94%).

(2) To a solution of hydroxylamine hydrochloride (2.24 g, 32.3 mmol) in dimethyl sulfoxide (10.6 mL), triethylamine (4.51 mL, 32.4 mmol) was added and the resulting mixture was stirred at room temperature for an hour. The precipitating salt was filtered and washed with THF. The THF was distilled off under reduced pressure and after adding the foregoing compound (n-2) (1.50 g, 6.46 mmol), the resulting mixture was stirred at 75° C. for 15 hours. The reaction mixture was cooled to room temperature and after adding water, extraction was conducted with ethyl acetate. The organic layer was successively washed with water and saturated brine and dried over anhydrous sodium sulfate. The solvents were distilled off under reduced pressure to give tert-butyl 4-(N'-hydroxycarbamimidoyl)benzylcarbamate (n-3) (amount, 1.70 g; yield, 99%).

(3) A solution of the foregoing compound (n-3) (1.46 g, 5.50 mmol) in pyridine (27.5 mL) was cooled to 0° C. To the cooled solution, ethyl chloroformate (0.550 mL, 5.78 mmol)

was added and after one-hour stirring at 0° C., the reaction temperature was raised to 100° C. at which further stirring was done overnight. The reaction mixture was cooled to room temperature and after adding water, extraction was conducted with ethyl acetate. The organic layer was successively washed with water and saturated brine and dried over anhydrous sodium sulfate. The solvents were distilled off under reduced pressure and the residue was purified by silica gel column chromatography (n-hexane:ethyl acetate=1:1) to give tert-butyl 4-(5-oxo-4,5-dihydro-1,2,4-oxadiazol-3-yl) benzylcarbamate (n-4) (amount, 1.14 g; yield, 71%).

(4) To a solution of the foregoing compound (n-4) (147 mg, 0.504 mmol) in 1,4-dioxane (1.5 mL), a 1,4-dioxane solution (1.50 mL, 6.00 mmol) of 4 mol/L hydrogen chloride was added and the resulting mixture was stirred at room temperature for an hour. The solvent was distilled off under reduced pressure to give 3-[4-(aminomethyl)phenyl]-1,2,4-oxadiazol-5(4H)-one hydrochloride (n-5) (122 mg, 100%).

(5) Compound 9 was produced by the same method as in Example 1, except that compound (a-6) was replaced by compound (n-5). The structural formula of Compound 9 and the data on its properties will be shown later in Table 1.

TABLE 1

| Compound No. | Structural formula | NMR, MASS |
| --- | --- | --- |
| 1 | | $^1$H-NMR (CDCl3) δ: 0.95-1.05 (2H, m), 1.33-1.48 (2H, m), 1.50-1.60 (1H, m), 1.63 (6H, s), 1.82-1.91 (2H, m), 2.01-2.09 (2H, m), 2.18-2.30 (1H, m), 3.24 (2H, dd, J = 6.4, 6.4 Hz), 5.78 (2H, s), 7.20-7.28 (3H, m), 7.57 (2H, d, J = 8.2 Hz).<br>ESI-MS m/z: 524 (M − H)$^-$. |
| 2 | | $^1$H-NMR (CD3OD) δ: 1.44 (6H, s), 4.56 (2H, s), 5.69 (2H, s), 7.31 (2H, d, J = 7.8 Hz), 7.37 (2H, d, J = 8.7 Hz), 7.63 (2H, d, J = 8.2 Hz), 7.95 (2H, d, J = 8.7 Hz).<br>ESI-MS m/z: 520 (M + H)$^+$. |
| 3 | | $^1$H-NMR (DMSO-d6) δ: 1.42 (3H, d, J = 6.9 Hz), 1.44 (3H, s), 1.46 (3H, s), 5.00-5.08 (1H, m), 5.46-5.56 (2H, m), 5.60 (1H, s), 7.22 (2H, d, J = 7.8 Hz), 7.42 (2H, d, J = 8.2 Hz), 7.65 (2H, d, J = 8.2 Hz), 7.83 (2H, d, J = 8.2 Hz).<br>ESI-MS m/z: 534 (M + H)$^+$. |
| 4 | | $^1$H-NMR (CD3OD) δ: 1.35-1.39 (4H, m), 1.55 (6H, s), 5.63 (2H, s), 7.14 (2H, d, J = 8.7 Hz), 7.27 (2H, d, J = 7.8 Hz), 7.65 (2H, d, J = 8.2 Hz), 7.85 (2H, d, J = 8.2 Hz).<br>ESI-MS m/z: 546 (M + H)$^+$. |

TABLE 1-continued

| Compound No. | Structural formula | NMR, MASS |
|---|---|---|
| 5 | | ¹H-NMR (CD3OD) δ: 1.40 (6H, s), 2.53 (3H, s), 4.50-4.54 (2H, m), 5.71 (2H, s), 7.16 (1H, d, J = 8.2 Hz), 7.21 (1H, s), 7.30 (2H, d, J = 8.2 Hz), 7.61 (2H, d, J = 8.2 Hz), 7.85 (1H, d, J = 7.8 Hz), 8.39-8.45 (1H, m). ESI-MS m/z: 534 (M + H)⁺. |
| 6 | | ¹H-NMR (CD3OD) δ: 1.54 (6H, s), 4.88 (2H, s), 5.70 (2H, s), 7.29 (2H, d, J = 7.8 Hz), 7.38 (1H, d, J = 5.5 Hz), 7.62 (2H, d, J = 8.2 Hz), 8.49 (1H, d, J = 5.5 Hz), 9.02 (1H, s). ESI-MS m/z: 521 (M + H)⁺. |
| 7 | | ¹H-NMR (CD3OD) δ: 1.45 (6H, s), 4.58-4.61 (2H, m), 5.70 (2H, s), 7.32 (2H, d, J = 8.2 Hz), 7.52 (2H, d, J = 8.7 Hz), 7.62 (2H, d, J = 8.2 Hz), 7.97 (2H, d, J = 8.7 Hz), 8.50-8.55 (1H, m). ESI-MS m/z: 542 (M − H)⁻. |
| 8 | | ¹H-NMR (CD3OD) δ: 1.11-1.22 (2H, m), 1.51-1.62 (8H, m), 1.62-1.73 (1H, m), 1.89-1.97 (2H, m), 2.06-2.15 (2H, m), 2.92-3.02 (1H, m), 3.21-3.27 (2H, m), 5.70 (2H, s), 7.32 (2H, d, J = 7.8 Hz), 7.65 (2H, d, J = 8.2 Hz), 8.01-8.08 (1H, m). ESI-MS m/z: 550 (M + H)⁺. |
| 9 | | ¹H-NMR (DMSO-d6) δ: 1.39 (6H, s), 4.49 (2H, d, J = 6.0 Hz), 5.55-5.61 (3H, m), 7.29 (2H, d, J = 7.8 Hz), 7.45 (2H, d, J = 8.2 Hz), 7.68-7.76 (4H, m), 8.64(1H, t, J = 6.4 Hz). ESI-MS: m/z 558 (M − H)⁻. |

TABLE 1-continued

| Compound No. | Structural formula | NMR, MASS |
|---|---|---|
| 10 | | $^1$H-NMR (CDCl3) δ: 0.92-1.05 (2H, m), 1.37-1.60 (9H, m), 1.82-1.91 (2H, m), 2.00-2.09 (2H, m), 2.20-2.32 (1H, m), 3.24 (2H, dd, J = 6.4, 6.4 Hz), 3.40 (3H, s), 5.77 (2H, s), 7.22 (1H, t, J = 6.0 Hz), 7.27 (2H, d, J = 8.2 Hz), 7.57 (2H, d, J = 8.2 Hz). ESI-MS m/z: 540 (M + H)$^+$. |
| 11 | | $^1$H-NMR (CDCl3) δ: 0.93-1.04 (2H, m), 1.21 (3H, t, J = 6.9 Hz), 1.37-1.50 (2H, m), 1.50-1.61 (7H, m), 1.82-1.92 (2H, m), 2.00-2.10 (2H, m), 2.21-2.30 (1H, m), 3.24 (2H, dd, J = 6.4, 6.4 Hz), 3.65 (2H, q, J = 7.0 Hz), 5.77 (2H, s), 7.21-7.29 (3H, m), 7.57 (2H, d, J = 8.2 Hz). ESI-MS m/z: 554 (M + H)$^+$. |
| 12 | | $^1$H-NMR (CDCl3) δ: 0.93-1.07 (2H, m), 1.20 (6H, d, J = 6.4 Hz), 1.35-1.48 (2H, m), 1.50-1.58 (7H, m), 1.83-1.91 (2H, m), 2.01-2.09 (2H, m), 2.22-2.33 (1H, m), 3.21-3.28 (2H, m), 4.03-4.14 (1H, m), 5.77 (2H, s), 7.20-7.30 (3H, m), 7.58 (2H, d, J = 8.2 Hz). ESI-MS m/z: 568 (M + H)$^+$. |
| 13 | | $^1$H-NMR (CDCl3) δ: 0.19-0.24 (2H, m), 0.53-0.57 (2H, m), 0.94-1.07 (3H, m), 1.37-1.47 (2H, m), 1.51-1.61 (7H, m), 1.81-1.90 (2H, m), 2.01-2.10 (2H, m), 2.22-2.32 (1H, m), 3.24 (2H, dd, J = 6.4, 6.4 Hz), 3.42 (2H, d, J = 6.9 Hz), 5.77 (2H, s), 7.21-7.29 (3H, m), 7.58 (2H, d, J = 8.2 Hz). ESI-MS m/z: 580 (M + H)$^+$. |
| 14 | | $^1$H-NMR (CDCl3) δ: 0.95-1.08 (2H, m), 1.37-1.49 (2H, m), 1.50-1.62 (1H, m), 1.72 (3H, s), 1.77 (3H, s), 1.85-1.92 (2H, m), 1.98-2.09 (2H, m), 2.21-2.32 (1H, m), 3.25 (2H, dd, J = 6.4, 6.4 Hz), 5.76 (2H, s), 7.09 (1H, t, J = 5.7 Hz), 7.26 (2H, d, J = 7.8 Hz), 7.57 (2H, d, J = 8.2 Hz). ESI-MS m/z: 528 (M + H)$^+$. |

TABLE 1-continued

| Compound No. | Structural formula | NMR, MASS |
|---|---|---|
| 15 | | $^1$H-NMR (CDCl3) δ: 0.92-1.14 (8H, m), 1.34-1.47 (2H, m), 1.47-1.60 (1H, m), 1.72-1.90 (6H, m), 1.99-2.07 (2H, m), 2.21-2.30 (1H, m), 3.23 (2H, dd, J = 6.4, 6.4 Hz), 5.77 (2H, s), 7.22-7.29 (3H, m), 7.57 (2H, d, J = 8.2 Hz). ESI-MS m/z: 554 (M + H)$^+$. |
| 16 | | $^1$H-NMR (CDCl3) δ: 0.94-1.07 (2H, m), 1.36-1.48 (2H, m), 1.49-1.60 (1H, m), 1.76-1.95 (6H, m), 2.00-2.08 (6H, m), 2.20-2.32 (1H, m), 3.24 (2H, dd, J = 6.4, 6.4 Hz), 5.77 (2H, s), 7.23-7.29 (3H, m), 7.57 (2H, d, J = 8.2 Hz). ESI-MS m/z: 552 (M + H)$^+$. |
| 17 | | $^1$H-NMR (CDCl3) δ: 0.92-1.05 (2H, m), 1.20-2.15 (17H, m), 2.20-2.35 (1H, m), 3.23 (2H, dd, J = 6.4, 6.4 Hz), 5.77 (2H, s), 7.23-7.32 (3H, m), 7.57 (2H, d, J = 8.2 Hz). ESI-MS m/z: 566 (M + H)$^+$. |
| 18 | | $^1$H-NMR (CDCl3) δ: 0.91-1.05 (2H, m), 1.22-1.29 (3H, m), 1.33-1.47 (2H, m), 1.48-1.63 (7H, m), 1.83-1.91 (2H, m), 1.98-2.08 (2H, m), 2.19-2.30 (1H, m), 2.61 (2H, q, J = 7.5 Hz), 3.22 (2H, dd, J = 6.4, 6.4 Hz), 5.73 (2H, s), 7.08 (2H, d, J = 7.8 Hz), 7.25-7.31 (1H, m), 7.55 (2H, d, J = 8.2 Hz). ESI-MS m/z: 520 (M + H)$^+$. |
| 19 | | $^1$H-NMR (CDCl3) δ: 0.92-1.06 (2H, m), 1.22-1.31 (3H, m), 1.33-1.47 (2H, m), 1.48-1.60 (7H, m), 1.83-1.91 (2H, m), 1.98-2.10 (2H, m), 2.19-2.31 (1H, m), 2.61 (2H, q, J = 7.5 Hz), 3.22 (2H, dd, J = 6.4, 6.4 Hz), 3.42 (3H, s), 5.73 (2H, s), 7.08 (2H, d, J = 7.8 Hz), 7.25-7.31 (1H, m), 7.55 (2H, d, J = 8.2 Hz). ESI-MS m/z: 534 (M + H)$^+$. |

TABLE 1-continued

| Compound No. | Structural formula | NMR, MASS |
|---|---|---|
| 20 | | $^1$H-NMR (DMSO-d6) δ: 0.85-0.89 (4H, m), 1.36 (6H, s), 1.98-2.02 (1H, m), 4.48 (2H, d, J = 6.4 Hz), 5.50 (1H, s), 5.74 (2H, s), 7.24 (2H, d, J = 7.8 Hz), 7.32 (2H, d, J = 8.2 Hz), 7.70 (2H, d, J = 8.3 Hz), 7.84 (2H, d, J = 8.2 Hz), 8.27 (1H, t, J = 6.4 Hz). ESI-MS: m/z 526 (M + H)$^+$. |
| 21 | | $^1$H-NMR (DMSO-d6) δ: 0.84-0.95 (2H, m), 1.16-1.27 (2H, m), 1.45 (6H, s), 1.70-1.74 (2H, m), 1.84-1.88 (2H, m), 2.10 (1H, tt, J = 12.1, 3.3 Hz), 2.26 (3H, s), 2.49-2.52 (1H, m), 3.07 (2H, t, J = 6.4 Hz), 5.44 (2H, s), 5.54 (1H, s), 6.99 (2H, d, J = 8.2 Hz), 7.13 (2H, d, J = 8.2 Hz), 8.05 (1H, t, J = 6.0 Hz), 12.03 (1H, s). ESI-MS m/z: 472 (M + H)$^+$. |
| 22 | | $^1$H-NMR (CDCl3) δ: 0.92-1.06 (2H, m), 1.35-1.49 (2H, m), 1.49-1.60 (7H, m), 1.81-1.90 (2H, m), 2.00-2.10 (2H, m), 2.21-2.34 (4H, m), 3.25 (2H, dd, J = 6.4, 6.4 Hz), 3.39 (3H, s), 5.67 (2H, s), 7.06-7.13 (5H, m). ESI-MS: m/z 486 (M + H)$^+$. |
| 23 | | $^1$H-NMR (DMSO-d6) δ: 0.84-0.95 (2H, m), 1.16-1.29 (3H, m), 1.45 (6H, s), 1.70-1.74 (2H, m), 1.84-1.88 (2H, m), 2.07-2.15 (1H, m), 3.07 (2H, t, J = 6.4 Hz), 5.47 (2H, s), 5.56 (1H, s), 7.16-7.20 (4H, m), 8.04 (1H, t, J = 6.0 Hz), 12.04 (1H, br s). ESI-MS m/z: 476 (M + H)$^+$. |
| 24 | | $^1$H-NMR (CDCl3) δ: 0.93-1.07 (2H, m), 1.36-1.48 (2H, m), 1.50-1.66 (7H, m), 1.84-1.92 (2H, m), 2.00-2.09 (2H, m), 2.22-2.32 (1H, m), 3.25 (2H, dd, J = 6.4, 6.4 Hz), 5.66 (2H, s), 7.11 (2H, d, J = 8.2 Hz), 7.19 (1H, t, J = 6.0 Hz), 7.26-7.29 (2H, m). ESI-MS m/z: 492, 494 (M + H)$^+$. |

TABLE 1-continued

| Compound No. | Structural formula | NMR, MASS |
|---|---|---|
| 25 | | $^1$H-NMR (CDCl3) δ: 0.92-1.07 (2H, m), 1.35-1.49 (2H, m), 1.49-1.60 (7H, m), 1.81-1.91 (2H, m), 2.00-2.10 (2H, m), 2.21-2.40 (1H, m), 3.25 (2H, dd, J = 6.4, 6.4 Hz), 3.40 (3H, s), 5.67 (2H, s), 7.13 (2H, d, J = 8.7 Hz), 7.17 (1H, t, J = 6.0 Hz), 7.28 (2H, d, J = 8.2 Hz). ESI-MS: m/z 506 (M + H)$^+$. |
| 26 | | $^1$H-NMR (CDCl3) δ: 0.93-1.06 (2H, m), 1.34-1.48 (2H, m), 1.49-1.58 (1H, m), 1.63 (6H, s), 1.82-1.90 (2H, m), 1.96-2.04 (2H, m), 2.19-2.28 (1H, m), 3.25 (2H, dd, J= 6.4, 6.4 Hz), 3.66 (3H, s), 5.77 (2H, s), 7.19 (1H, t, J = 6.0 Hz), 7.35 (1H, d, J = 7.3 Hz), 7.43 (1H d, J = 7.8 Hz), 7.55 (1H, d, J = 7.8 Hz). ESI-MS m/z: 526 (M + H)$^+$. |
| 27 | | $^1$H-NMR (CDCl3) δ: 0.93-1.06 (2H, m), 1.35-1.48 (2H, m), 1.53-1.63 (7H, m), 1.83-1.91 (2H, m), 2.00-2.08 (2H, m), 2.21-2.31 (1H, m), 3.25 (2H, dd, J = 6.4, 6.4 Hz), 5.70 (2H, s), 6.82-6.87 (1H, m), 6.92-6.99 (2H, m), 7.18-7.23 (1H, m), 7.24-7.31 (1H, m). ESI-MS m/z: 576 (M + H)$^+$. |
| 28 | | $^1$H-NMR (CDCl3) δ: 0.93-1.06 (2H, m), 1.34-1.48 (2H, m), 1.49-1.59 (7H, m), 1.82-1.90 (2H, m), 2.01-2.09 (2H, m), 2.21-2.32 (1H, m), 3.25 (2H, dd, J = 6.4, 6.4 Hz), 3.40 (3H, s), 5.71 (2H, s), 6.84-6.89 (1H, m), 6.94-7.00 (2H, m), 7.18 (1H, t, J = 6.0 Hz), 7.24-7.31 (1H, m). ESI-MS m/z: 490 (M + H)$^+$. |
| 29 | | $^1$H-NMR (CD3OD) δ: 0.94-1.07 (2H, m), 1.31-1.43 (2H, m), 1.51-1.61 (7H, m), 1.78-1.86 (2H, m), 1.94-2.02 (2H, m), 2.16-2.26 (1H, m), 3.18 (2H, dd, J = 6.4, 6.4 Hz), 5.56 (2H, s), 6.95-7.00 (1H, m), 7.09-7.16 (1H, m), 7.20-7.28 (1H, m), 7.96-8.02 (1H, m). ESI-MS m/z: 494 (M + H)$^+$. |

TABLE 1-continued

| Compound No. | Structural formula | NMR, MASS |
|---|---|---|
| 30 | | ¹H-NMR (CDCl3) δ: 0.95-1.08 (2H, m), 1.36-1.49 (2H, m), 1.51-1.60 (7H, m), 1.84-1.93 (2H, m), 2.02-2.10 (2H, m), 2.23-2.33 (1H, m), 3.26 (2H, dd, J = 6.4, 6.4 Hz), 3.40 (3H, s), 5.66 (2H, s), 6.94-6.99 (1H, m), 7.00-7.15 (2H, m), 7.22 (1H, t, J = 6.4 Hz).<br>ESI-MS m/z: 508 (M + H)⁺. |
| 31 | | ¹H-NMR (CDCl3) δ: 0.95-1.09 (2H, m), 1.37-1.50 (2H, m), 1.51-1.68 (7H, m), 1.85-1.93 (2H, m), 2.00-2.09 (2H, m), 2.22-2.32 (1H, m), 3.25 (2H, dd, J = 6.4, 6.4 Hz), 5.80 (2H, s), 7.26-7.31 (1H, m), 7.65 (1H, d, J = 8.2 Hz), 7.73 (1H, dd, J = 8.3, 1.8 Hz), 8.65 (1H, d, J = 1.8 Hz).<br>ESI-MS m/z: 527 (M + H)⁺. |
| 32 | | ¹H-NMR (CDCl3) δ: 0.93-1.06 (2H, m), 1.34-1.48 (2H, m), 1.49-1.58 (1H, m), 1.63 (6H, s), 1.82-1.90 (2H, m), 1.96-2.04 (2H, m), 2.19-2.28 (1H, m), 3.25 (2H, dd, J = 6.4, 6.4 Hz), 3.66 (3H, s), 5.77 (2H, s), 7.19 (1H, t, J = 6.0 Hz), 7.35 (1H, d, J = 7.3 Hz), 7.43 (1H d, J = 7.8 Hz), 7.55 (1H, d, J = 7.8 Hz).<br>ESI-MS m/z: 473 (M + H)⁺. |
| 33 | | ¹H-NMR (DMSO-d6) δ: 0.92-1.03 (2H, m), 1.20-1.32 (2H, m), 1.46-1.55 (7H, m), 1.79-1.94 (4H, m), 2.09-2.17 (1H, m), 2.19 (3H, s), 2.29 (3H, s), 2.96 (2H, t, J = 7.4 Hz), 3.13 (2H, dd, J = 6.4, 6.4 Hz), 4.35 (2H, t, J = 7.4 Hz), 5.58 (1H, s), 6.82 (2H, d, J = 6.8 Hz), 6.97 (2H, dd, J = 7.8, 7.4 Hz), 7.04 (2H, d, J = 7.4 Hz), 7.87 (1H, t, J = 6.0 Hz), 12.03 (1H, s).<br>ESI-MS: m/z 500 (M + H)⁺. |
| 34 | | ¹H-NMR (DMSO-d6) δ: 0.98-1.04 (2H, m), 1.19-1.24 (2H, m), 1.46-1.56 (7H, m), 1.78-1.95 (4H, m), 2.08-2.20 (1H, m), 2.92 (2H, t, J = 6.9 Hz), 3.12 (2H, dd, J = 6.4, 6.4 Hz), 4.42 (2H, t, J = 7.3 Hz), 5.58 (1H, s), 7.11 (2H, d, J = 8.2 Hz), 7.34 (2H, d, J = 8.2 Hz), 7.91 (1H, t, J = 6.0 Hz), 12.03 (1H, s).<br>ESI-MS: m/z 504 (M − H)⁻. |

TABLE 1-continued

| Compound No. | Structural formula | NMR, MASS |
|---|---|---|
| 35 | | ¹H-NMR (DMSO-d6) δ: 0.95-1.04 (2H, m), 1.20-1.32 (2H, m), 1.46-1.55 (7H, m), 1.78-1.92 (4H, m), 2.10-2.21 (1H, m), 2.91 (2H, t, J = 6.9 Hz), 3.11 (2H, dd, J = 6.4, 6.4 Hz), 3.29 (3H, s), 4.38 (2H, t, J = 6.9 Hz), 7.12 (2H, d, J = 8.7 Hz), 7.34 (2H, d, J = 8.3 Hz), 8.14 (1H, t, J = 6.0 Hz), 12.04 (1H, s). ESI-MS: m/z 520 (M + H)⁺. |
| 36 | | ¹H-NMR (DMSO-d6) δ: 0.98-1.04 (2H, m), 1.19-1.24 (2H, m), 1.46-1.56 (7H, m), 1.78-1.95 (4H, m), 2.08-2.20 (1H, m), 2.92 (2H, t, J = 6.9 Hz), 3.12 (2H, dd, J = 6.4, 6.4 Hz), 4.42 (2H, t, J = 7.3 Hz), 5.58 (1H, s), 7.11 (2H, d, J = 8.2 Hz), 7.34 (2H, d, J = 8.2 Hz), 7.91 (1H, t, J = 6.0 Hz), 12.03 (1H, s). ESI-MS: m/z 556 (M + H)⁺. |
| 37 | | ¹H-NMR (DMSO-d6) δ: 0.92-1.03 (2H, m), 1.20-1.31 (2H, m), 1.46-1.52 (7H, m), 1.78-1.95 (4H, m), 2.10-2.18 (1H, m), 2.96 (2H, t, J = 6.9 Hz), 3.11 (2H, dd, J = 6.4, 6.4 Hz), 3.29 (3H, s), 4.39 (2H, t, J = 6.8 Hz), 7.23 (2H, d, J = 8.7 Hz), 7.29 (2H, d, J = 8.2 Hz), 8.15 (1H, t, J = 6.0 Hz), 12.04 (1H, s). ESI-MS: m/z 568 (M − H)⁻. |
| 38 | | ¹H-NMR (DMSO-d6) δ: 0.90-1.00 (2H, m), 1.19-1.29 (3H, m), 1.45 (6H, s), 1.78-1.89 (7H, m), 2.09 (3H, s), 2.10-2.18 (2H, m), 2.21 (3H, s), 3.12 (2H, t, J = 6.4 Hz), 4.28 (2H, t, J = 7.1 Hz), 5.56 (1H, s), 6.92-6.98 (3H, m), 8.04 (1H, t, J = 6.0 Hz), 12.03 (1H, br s). ESI-MS m/z: 512(M − H)⁻. |

TABLE 1-continued

| Compound No. | Structural formula | NMR, MASS |
|---|---|---|
| 39 | | $^1$H-NMR (DMSO-d6) δ: 0.90-1.02 (2H, m), 1.18-1.32 (2H, m), 1.45-1.55 (7H, m), 1.78-1.92 (4H, m), 2.08-2.18 (1H, m), 3.11 (2H, dd, J = 6.4, 6.4 Hz), 4.21 (2H, t, J = 5.0 Hz), 4.62 (2H, t, J = 5.0 Hz), 5.54 (1H, s), 6.89 (2H, d, J = 9.2 Hz), 7.30 (2H, d, J = 9.2 Hz), 8.02 (1H, t, J = 6.0 Hz), 12.02 (1H, s). ESI-MS: m/z 522 (M + H)$^+$. |
| 40 | | $^1$H-NMR (DMSO-d6) δ: 0.91-1.02 (2H, m), 1.20-1.29 (2H, m), 1.45-1.55 (7H, m), 1.76-1.92 (4H, m), 3.09 (2H, dd, J = 6.4, 6.4 Hz), 3.28 (3H, s), 4.20 (2H, t, J = 5.0 Hz), 4.59 (2H, t, J = 5.0 Hz), 6.89 (2H, d, J = 8.7 Hz), 7.31 (2H, d, J = 8.7 Hz), 8.26 (1H, t, J = 6.0 Hz), 12.02 (1H, s). ESI-MS: m/z 536 (M + H)$^+$. |
| 41 | | $^1$H-NMR (CDCl3) δ: 1.38 (6H, s), 3.28 (3H, s), 4.64 (2H, d, J = 6.0 Hz), 5.80 (2H, s), 7.28 (2H, d, J = 8.2 Hz), 7.38 (2H, d, J = 8.7 Hz), 7.54-7.62 (3H, m), 8.07 (2H, d, J = 8.7 Hz). ESI-MS m/z: 534 (M + H)$^+$. |
| 42 | | $^1$H-NMR (CDCl3) δ: 1.39-1.47 (4H, m), 1.55 (6H, s), 3.39 (3H, s), 5.74 (2H, s), 7.19 (2H, d, J = 8.2 Hz), 7.28 (2H, d, J = 8.2 Hz), 7.56 (2H, d, J = 8.2 Hz), 7.83 (1H, s), 7.97 (2H, d, J = 8.7 Hz). ESI-MS m/z: 560 (M + H)$^+$. |
| 43 | | $^1$H-NMR (CDCl3) δ: 1.57 (6H, s), 1.74 (6H, s), 3.44 (3H, s), 5.64 (2H, s), 7.20 (2H, d, J = 7.8 Hz), 7.40 (1H, s), 7.42 (2H, d, J = 8.7 Hz), 7.54 (2H, d, J = 7.8 Hz), 8.01 (2H, d, J = 8.7 Hz). ESI-MS: m/z 562 (M + H)$^+$. |

TABLE 1-continued

| Compound No. | Structural formula | NMR, MASS |
|---|---|---|
| 44 | | $^1$H-NMR (DMSO-d6) δ: 1.36 (6H, s), 4.21 (2H, t, J = 5.0 Hz), 4.54 (2H, d, J = 6.0 Hz), 4.63 (2H, t, J = 5.0 Hz), 5.52 (1H, s), 6.86 (2H, d, J = 8.7 Hz), 7.29 (2H, d, J = 9.2 Hz), 7.48 (2H, d, J = 8.3 Hz), 7.89 (2H, d, J = 8.2 Hz), 8.65 (1H, t, J = 6.4 Hz). ESI-MS: m/z 516 (M + H)$^+$. |
| 45 | | $^1$H-NMR (DMSO-d6) δ: 1.34 (6H, s), 3.19 (3H, s), 4.20 (2H, t, J = 5.0 Hz), 4.52 (2H, d, J = 6.0 Hz), 4.62 (2H, t, J = 5.0 Hz), 6.86 (2H, d, J = 9.2 Hz), 7.29 (2H, d, J = 9.2 Hz), 7.47 (2H, d, J = 8.7 Hz), 7.89 (2H, d, J = 8.7 Hz), 8.87 (1H, t, J = 6.0 Hz). ESI-MS: m/z 530 (M + H)$^+$. |
| 46 | | $^1$H-NMR (CD3OD) δ: 0.95-1.00 (4H, m), 1.38 (6H, s), 1.91-2.00 (1H, m), 3.29 (3H, s), 4.55 (2H, br, s), 5.80 (2H, s), 7.27 (2H, d, J = 8.2 Hz), 7.35 (2H, d, J = 8.2 Hz), 7.63 (2H, d, J = 8.2 Hz), 7.94 (2H, d, J = 8.2 Hz). ESI-MS m/z: 540 (M + H)$^+$. |
| 47 | | $^1$H-NMR (CDCl3) δ: 1.03-1.08 (2H, m), 1.12-1.17 (2H, m), 1.36 (6H, s), 2.08-2.18 (1H, m), 3.25 (3H, s), 4.33 (2H, t, J = 5.0 Hz), 4.67 (2H, d, J = 5.5 Hz), 4.89 (2H, d, J = 5.0 Hz), 6.76 (2H, d, J = 9.2 Hz), 7.20 (2H, d, J = 9.2 Hz), 7.44 (2H, d, J = 8.2 Hz), 7.74 (1H, t, J = 5.5 Hz), 8.07 (2H, d, J = 8.2 Hz). ESI-MS: m/z 536 (M + H)$^+$. |
| 48 | | $^1$H-NMR (CDCl3) δ: 0.95-1.05 (2H, m), 1.37-1.60 (9H, m), 1.83-1.92 (2H, m), 2.01-2.10 (2H, m), 2.22-2.32 (1H, m), 3.26 (2H, t, J = 6.4 Hz), 3.40 (3H, s), 5.71 (2H, s), 7.12-7.29 (5H, m). ESI-MS m/z: 556 (M + H)$^+$. |

TABLE 1-continued

| Compound No. | Structural formula | NMR, MASS |
|---|---|---|
| 49 | | ¹H-NMR (CDCl3): 1.37 (6H, s), 3.27 (3H, s), 4.65 (2H, d, J = 6.0 Hz), 5.66 (2H, s), 7.10 (2H, d, J = 8.2 Hz), 7.19 (2H, d, J = 8.7 Hz), 7.31 (2H, d, J = 7.9 Hz), 7.56 (1H, t, J = 5.7 Hz), 8.06 (2H, d, J = 7.9 Hz).<br>ESI-MS m/z: 550 (M + H)⁺. |
| 50 | | ¹H-NMR (CDCl3): 1.50 (3H, s), 1.51 (3H, s), 1.59 (3H, d, J = 6.9 Hz), 3.38 (3H, s), 5.21-5.31 (1H, m), 5.60 (1H, d, J = 15.6 Hz), 5.75 (1H, d, J = 15.6 Hz), 7.13 (2H, d, J = 8.2 Hz), 7.20 (2H, d, J = 8.6 Hz), 7.43 (2H, d, J = 8.2 Hz), 7.48 (1H, d, J = 7.3 Hz), 8.08 (2H, d, J = 8.2 Hz).<br>ESI-MS m/z: 564 (M + H)⁺. |
| 51 | | ¹H-NMR (CDCl3) δ: 0.95-1.05 (2H, m), 1.37-1.48 (3H, m), 1.55 (6H, s), 1.85-1.89 (2H, m), 2.03-2.07 (2H, m), 2.23-2.31 (1H, m), 3.25 (2H, t, J = 6.4 Hz), 3.40 (3H, s), 5.69 (2H, s), 6.48 (1H, t, JH-F = 73.7 Hz), 7.06 (2H, d, J = 8.7 Hz), 7.17-7.22 (3H, m).<br>ESI-MS m/z: 538 (M + H)⁺. |
| 52 | | ¹H-NMR (CDCl3) δ: 1.38 (6H, s), 3.28 (3H, s), 4.66 (2H, d, J = 6.0 Hz), 5.71 (2H, s), 6.50 (1H, t, JH-F = 73.5 Hz), 7.07 (2H, d, J = 8.2 Hz), 7.22 (2H, d, J = 8.7 Hz), 7.39 (2H, d, J = 8.2 Hz), 7.55 (1H, t, J = 6.0 Hz), 8.07 (2H, d, J = 8.2 Hz).<br>ESI-MS m/z: 532 (M + H)⁺. |
| 53 | | ¹H-NMR (CDCl3) δ: 0.95-1.05 (2H, m), 1.37-1.48 (3H, m), 1.56 (6H, s), 1.85-1.89 (2H, m), 2.03-2.07 (2H, m), 2.23-2.31 (1H, m), 3.25 (2H, t, J = 6.4 Hz), 3.40 (3H, s), 5.72 (2H, s), 6.49 (1H, t, JH-F = 73.5 Hz), 6.95 (1H, s), 7.00-7.05 (2H, m), 7.19 (1H, t, J = 6.0 Hz), 7.31 (1H, dd, J = 8.0, 8.0 Hz).<br>ESI-MS m/z: 538 (M + H)⁺. |

TABLE 1-continued

| Compound No. | Structural formula | NMR, MASS |
|---|---|---|
| 54 | | $^1$H-NMR (CDCl3) δ: 1.39 (6H, s), 3.28 (3H, s), 4.66 (2H, d, J = 5.5 Hz), 5.74 (2H, s), 6.49 (1H, t, JH-F = 73.7 Hz), 6.98 (1H, s), 7.02-7.07 (2H, m), 7.32 (1H, dd, J = 8.0, 8.0 Hz), 7.39 (2H, d, J = 8.2 Hz), 7.56 (1H, t, J = 5.7 Hz), 8.07 (2H, d, J = 8.2 Hz). ESI-MS m/z: 532 (M + H)$^+$. |
| 55 | | $^1$H-NMR (CDCl3) δ: 0.95-1.05 (2H, m), 1.37-1.59 (9H, m), 1.82-1.91 (2H, m), 2.01-2.10 (2H, m), 2.22-2.31 (1H, m), 3.26 (2H, t, J = 6.4 Hz), 3.40 (3H, s), 5.67 (2H, s), 6.96-7.02 (2H, m), 7.14-7.22 (3H, m). ESI-MS m/z: 490 (M + H)$^+$. |
| 56 | | $^1$H-NMR (CDCl3) δ: 1.38 (6H, s), 3.27 (3H, s), 4.66 (2H, d, J = 5.5 Hz), 5.70 (2H, s), 6.99-7.04 (2H, m), 7.20-7.23 (2H, m), 7.39 (2H, d, J = 8.7 Hz), 7.54 (1H, t, J = 5.7 Hz), 8.07 (2H, d, J = 8.2 Hz). ESI-MS m/z: 484 (M + H)$^+$. |
| 57 | | $^1$H-NMR (CDCl3) δ: 1.50 (3H, s), 1.51 (3H, s), 1.59 (3H, d, J = 6.9 Hz), 3.38 (3H, s), 5.24-5.32 (1H, m), 5.57 (1H, d, J = 15.1 Hz), 5.70 (1H, d, J = 15.1 Hz), 6.94-6.99 (2H, m), 7.14-7.21 (2H, m), 7.40-7.48 (3H, m), 8.08 (2H, d, J = 8.2 Hz). ESI-MS m/z: 498 (M + H)$^+$. |
| 58 | | $^1$H-NMR (CD3OD) δ: 1.53 (3H, s), 1.54 (3H, s), 1.60 (3H, d, J = 6.9 Hz), 4.09-4.22 (2H, m), 4.65-4.75 (2H, m), 5.21 (1H, q, J = 6.9 Hz), 6.72 (2H, d, J = 9.6 Hz), 7.19 (2H, d, J = 9.6 Hz), 7.54 (2H, d, J = 8.2 Hz), 7.99 (2H, d, J = 8.2 Hz). ESI-MS m/z: 530 (M + H)$^+$. |

TABLE 1-continued

| Compound No. | Structural formula | NMR, MASS |
|---|---|---|
| 59 | 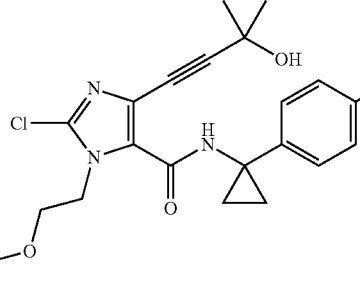 | ¹H-NMR (CD3OD) δ: 1.41-1.51 (4H, m), 1.55 (6H, s), 4.22 (2H, t, J = 5.3 Hz), 4.73 (2H, t, J = 5.0 Hz), 6.80 (2H, d, J = 9.8Hz), 7.21 (2H, d, J = 9.6 Hz), 7.38 (2H, d, J = 8.7 Hz), 7.92 (2H, d, J = 8.5 Hz). ESI-MS m/z: 542 (M + H)⁺. |
| 60 | 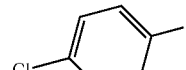 | ¹H-NMR (CDCl3) δ: 0.92-1.07 (2H, m), 1.34-1.48 (2H, m), 1.48-1.62 (7H, m), 1.80-1.91 (2H, m), 1.98-2.10 (2H, m), 2.20-2.31 (1H, m), 3.24 (2H, t, J = 6.4 Hz), 3.40 (3H, s), 5.75 (2H, s), 6.61 (1H, t, J = 56.3 Hz), 7.19 (1H, t, J = 5.7 Hz), 7.24 (2H, d, J = 7.8 Hz), 7.45 (2H, d, J = 7.8 Hz). ESI-MS m/z: 522 (M + H)⁺. |
| 61 | 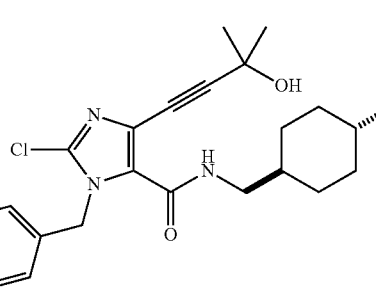 | ¹H-NMR (CDCl3) δ: 0.95-1.08 (2H, m), 1.27-1.50 (8H, m), 1.52-1.65 (1H, m), 1.87-2.10 (4H, m), 2.20-2.34 (1H, m), 3.25 (2H, t, J = 6.4 Hz), 3.53 (2H, s), 4.24 (2H, t, J = 5.0 Hz), 4.82 (2H, t, J = 4.8 Hz), 6.74 (2H, d, J = 9.2 Hz), 7.19 (2H, d, J = 9.2 Hz), 7.53 (1H, t, J = 6.0 Hz). ESI-MS m/z: 536 (M + H)⁺. |
| 62 | 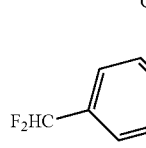 | ¹H-NMR (CDCl3) δ: 0.91-1.05 (2H, m), 1.28-1.66 (9H, m), 1.80-1.89 (2H, m), 1.98-2.09 (2H, m), 2.20-2.31 (1H, m), 3.22 (2H, t, J = 6.4 Hz), 3.31 (2H, s), 3.40 (3H, s), 5.78 (2H, s), 7.25 (2H, d, J = 7.8 Hz), 7.56 (1H, t, J = 8.2 Hz). ESI-MS m/z: 554 (M + H)⁺. |
| 63 | 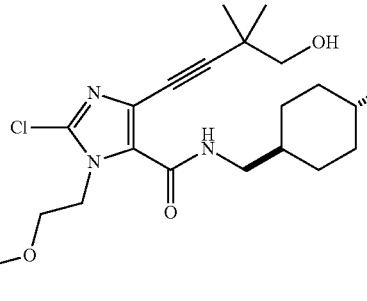 | ¹H-NMR (CDCl3) δ: 0.98-1.12 (2H, m), 1.38-1.51 (2H, m), 1.52-1.66 (7H, m), 1.85-1.95 (2H, m), 2.02-2.12 (2H, m), 2.22-2.34 (1H, m), 3.29 (2H, t, J = 6.4 Hz), 3.39 (3H, s), 4.27 (2H, t, J = 5.3 Hz), 4.95 (2H, t, J = 5.3 Hz), 6.74 (2H, d, J = 8.7 Hz), 6.91 (1H, t, JH-F = 52.6 Hz), 7.20 (2H, d, J = 8.7 Hz), 7.34 (1H, t, J = 5.9 Hz). ESI-MS m/z: 552 (M + H)⁺. |

TABLE 1-continued

| Compound No. | Structural formula | NMR, MASS |
|---|---|---|
| 64 | | ¹H-NMR (CDCl3) δ: 1.38 (6H, s), 3.27 (3H, s), 4.28 (2H, t, J = 5.0 Hz), 4.69 (2H, d, J = 5.9 Hz), 4.98 (2H, t, J = 5.3 Hz), 6.73 (2H, d, J = 9.1 Hz), 6.91 (1H, t, JH-F = 52.6 Hz), 7.20 (2H, d, J = 9.1 Hz), 7.45 (2H, d, J = 7.8 Hz), 7.70 (1H, t, J = 5.9 Hz), 8.08 (2H, d, J = 7.8 Hz). ESI-MS m/z: 546 (M + H)⁺. |
| 65 | | ¹H-NMR (CD3OD) δ: 0.92-1.03 (2H, m), 1.28-1.61 (9H, m), 1.80-1.88 (2H, m), 1.98-2.08 (2H, m), 2.20-2.30 (1H, m), 3.22 (2H, t, J = 6.4 Hz), 3.55 (2H, s), 5.77 (2H, s), 7.25 (2H, d, J = 9.6 Hz), 7.46 (1H, t, J = 6.2 Hz), 7.56 (2H, d, J = 8.2 Hz). ESI-MS m/z: 540 (M + H)⁺. |
| 66 | | ¹H-NMR (CDCl3) δ: 0.95-1.05 (2H, m), 1.37-1.48 (3H, m), 1.54 (6H, s), 1.85-1.89 (2H, m), 2.03-2.07 (2H, m), 2.24-2.30 (1H, m), 3.26 (2H, t, J = 6.4 Hz), 3.39 (3H, s), 3.77 (3H, s), 5.64 (2H, s), 6.82 (2H, d, J = 8.7 Hz), 7.12 (1H, t, J = 6.2 Hz), 7.17 (2H, d, J = 8.7 Hz). ESI-MS m/z: 502 (M + H)⁺. |
| 67 | | ¹H-NMR (DMSO-d6) δ: 1.22-1.34 (4H, m), 1.45 (6H, s), 2.32 (3H, s), 3.28 (3H, s), 5.37 (2H, s), 6.98 (2H, d, J = 8.2 Hz), 7.10 (2H, d, J = 8.2 Hz), 7.17 (2H, d, J = 8.2 Hz), 7.73 (2H, d, J = 8.7 Hz), 9.15 (1H, s). ESI-MS m/z: 506 (M + H)⁺. |
| 68 | | ¹H-NMR (DMSO-d6) δ: 1.27-1.34 (4H, m), 1.45 (6H, s), 2.31 (3H, s), 5.38 (2H, s), 5.56 (1H, s), 6.97 (2H, d, J = 8.2 Hz), 7.10 (2H, d, J = 8.7 Hz), 7.16 (2H, d, J = 8.2 Hz), 7.74 (2H, d, J = 8.7 Hz), 8.97 (1H, s). ESI-MS m/z: 492 (M + H)⁺. |

TABLE 1-continued

| Compound No. | Structural formula | NMR, MASS |
|---|---|---|
| 69 | (structure: 2-chloro-1-(4-trifluoromethylbenzyl)-4-(3-methoxy-1-propynyl)imidazole-5-carboxamide linked to N-CH2-C6H4-CO2H) | $^1$H-NMR (DMSO-d6) δ: 3.27 (3H, s), 4.31 (2H, s), 4.48 (2H, d, J = 6.0 Hz), 5.56 (2H, s), 7.30 (2H, d, J = 8.2 Hz), 7.35 (2H, d, J = 8.2 Hz), 7.71 (2H, d, J = 8.2 Hz), 7.85 (2H, d, J = 8.2 Hz), 8.95 (1H, t, J = 6.0 Hz). ESI-MS m/z: 506 (M + H)$^+$. |

Test Example 1

Test for Evaluating the Rat EP4 Receptor Antagonistic Action by the Reporter Assay Method The first step was the cloning of the rat EP4 receptor. Total RNA was prepared from the kidney extracted from rats. With the total RNA used as a template, the rat EP4 receptor gene was cloned by RT-PCR and its translated region was integrated into the expression vector pShooter (Invitrogen) to prepare a rat EP4 receptor expressing vector (ratEP4-pShooter).

In the next step, rat EP4 receptor expressing cells for use in the reporter assay were prepared. COS-7 cells (derived from the kidney of *Cercopithecus aethiops*) were cultured in Dulbecco's Modified Eagle Medium (DMEM) (supplemented with 10% fetal bovine serum) in a 75-cm$^2$ cell culture flask. After the cells proliferated to a subconfluent state, the medium was removed and rinsed with phosphate buffered physiological saline (PBS). Trypsin-EDTA and a growth medium were used to recover the cells, which were then centrifuged. The supernatant was removed and the cells were suspended in DMEM. The cell suspension was seeded on a 96-well plate at a density of 2×10$^4$ cells/100 μL/well and cultured. The DMEM was mixed with Plus reagent, Lipofectamine 2000, the rat EP4 receptor expressing vector (ratEP4-pShooter) and a CRE-LUC reporter vector (CLONTECH) to prepare a transfection solution. Three hours after the seeding of the cells, 50 μL of the medium was removed and 50 μL/well of the transfection solution was added, followed by culture overnight. Negative control cells were prepared using pShooter in place of the receptor expressing vector. The cells were seeded on a 96-well plate for reporter assay and cultured.

The medium on the 96-well plate was removed and a test compound was added in an amount of 50 μL/well. After ca. 30-min culture, a PGE$_2$ solution (2×10$^{-8}$ mol/L) was added in an amount of 50 μL/well (final concentration of PGE$_2$: 1×10$^{-8}$ mol/L). As a PGE$_2$-free control, there were provided wells to which a test medium had been added in an amount of 50 μL/well. About three hours later, the medium was removed and reporter assay was performed in accordance with the protocol accompanying the Steady-Glo Luciferase Assay System kit. Luminous intensity was measured with a microplate reader (Fusion-FPα, PerkinElmer) and EP4 receptor antagonistic activity (%) was determined by the following calculation formula:

$$EP4 \text{ receptor antagonistic activity } (\%) = [1-(RLU(A,X)-RLU(0))/(RLU(PGE_2)-RLU(0))] \times 100$$

RLU(A,X): Luminous intensity expressed in relative luminescence units (RLU) for the case where the test compound (A) X (mol/L) and PGE$_2$ 10$^{-8}$ mol/L were both added;

RLU(PGE$_2$): Luminous intensity for the case where only PGE$_2$ 10$^{-8}$ mol/L was added;

RLU(0): Luminous intensity for the case where neither test compound nor PGE$_2$ was added.

In addition, a dose-response curve was plotted from the EP4 receptor antagonistic activities at varying concentrations of each test compound and using the following approximation formula, the IC$_{50}$ (the concentration of the test compound required to inhibit the PGE$_2$ inducing activity by 50%) was calculated to determine the intensity of the compound's EP4 receptor antagonistic activity. The results are shown in Table 2:

$$Y = Bottom + (Top - Bottom)/\{1 + 10^{\wedge}(Log\ IC_{50} - Log\ X)\}$$

Bottom: 0
Top: 100
X: Concentration of the test compound (mol/L)
Y: EP4 receptor antagonistic activity (%)

TABLE 2

Intensity of EP4 Receptor Antagonistic Activity

| Compound No. | IC$_{50}$ (nmol/L) |
|---|---|
| 1 | 23.8 |
| 2 | 14.1 |
| 4 | 3.0 |
| 10 | 10.9 |
| 16 | 7.3 |
| 20 | 64.6 |
| 21 | 26.4 |
| 22 | 11.8 |
| 39 | 35.0 |
| 40 | 9.5 |
| 41 | 8.4 |
| 42 | 1.7 |
| 44 | 17.5 |
| 45 | 5.1 |
| 47 | 34.7 |
| 50 | 1.1 |
| 51 | 7.9 |
| 52 | 7.9 |
| 54 | 16.1 |
| 56 | 49.9 |
| 60 | 10.2 |
| 61 | 26.6 |
| 64 | 26.1 |
| 67 | 2.1 |
| 68 | 6.1 |

(Values are each a geometric mean of three cases.)

Test Example 2

Test for Evaluating the Anti-Inflammatory Effect on Carrageenin Induced Paw Edema in Rats The animals were Wistar male rats (7-week old). The paw volume of the right hind leg was measured with a paw volume meter (PLETHYSMOMETER, Ugo Basile Model 7141 or 7150). One hour after orally administering a test compound at a dose of 10 mg/5 mL/kg, a carrageenin treatment group was given a 1 w/v % carrageenin solution and a non-treatment group given distilled water, each administered subcutaneously to the footpad of the right hind leg at a dose of 0.1 mL. Four hours after the treatment with carrageenin (or distilled water), the paw volume was measured and the change in paw volume from the pre-treatment value was calculated. The anti-inflammatory effect of the test compound was confirmed using the percent paw edema suppression (see below) as an indicator. In the present experimental models, Cerecoxib (COX inhibitor already available on the market as an anti-inflammatory/analgesic agent) was used as a positive control. Cerecoxib, when administered in the present models, exhibited maximum efficacy at doses of 10~30 mg/kg and the percent paw edema suppression as defined below had values of 32~37(%) at the maximum efficacy:

Percent paw edema suppression (%)=[(paw volume change in the control group−paw volume in each treatment group)/(paw volume change in the control group−paw volume change in the non-treatment group)]×100

The results for compounds of the present invention are given in Table 3. The 4-alkynylimidazole derivatives of the present invention were verified to have an anti-inflammatory effect in view of their percent paw edema suppression.

TABLE 3

Anti-Inflammatory Effect on Carrageenin Induced Paw Edema in Rats

| Compound No. | Percent paw edema suppression (%) |
|---|---|
| 10 | 26 |
| 22 | 19 |
| 39 | 22 |
| 40 | 29 |
| 42 | 28 |
| 47 | 26 |

(Values are means of 5~8 cases.)

Test Example 3

Test for Evaluating Analgesic Effect on Carrageenin Induced Hyperalgesia in Rats The animals were SD male rats (5-week old). Before treatment with carrageenin (or distilled water), the rats were measured for nociceptive thresholds in their right hind leg by the Randall-Selitto method and divided into a carrageenin treatment group and a non-treatment group to provide uniformity in nociceptive threshold. The carrageenin treatment group was given a 1 w/v % carrageenin solution and the non-treatment group given distilled water, each administered subcutaneously to the footpad of the right hind leg at a dose of 0.1 mL. Five hours after the treatment, the nociceptive thresholds were measured and the individuals with decreased thresholds were selected and grouped such that there was no inter-group difference in threshold. Six hours after the treatment, each test compound was orally administered at a dose of 10 mg/5 mL/kg. The control group was administered 0.5% methylcellulose. Two hours after the administration of the test compound (8 hours after the treatment), the nociceptive threshold was measured. The animals in the test compound group that had nociceptive thresholds greater than [(the mean nociceptive threshold of the control group)+2×standard deviation] were found "effective animals" and the percent effectiveness of each compound was calculated.

The results are shown in Table 4. The 4-alkynylimidazole derivatives of the present invention were verified to have an analgesic effect in view of their percent effectiveness.

TABLE 4

Analgesic Effect on Carrageenin Induced Hyperalgesia in Rats

| Compound No. | Percent Effectiveness (%) |
|---|---|
| 10 | 100 |
| 22 | 83 |
| 39 | 100 |
| 40 | 100 |
| 42 | 83 |
| 44 | 50 |
| 45 | 50 |
| 47 | 67 |
| 67 | 100 |

(Values are means of 5~7 cases.)

Test Example 4

Test for Evaluating Anti-Inflammatory and Analgesic Effects on Adjuvant Induced Arthritis in Rats The animals were Lewis male rats (6-week old). An adjuvant solution (2 mg/mL) was administered intradermally to the footpad of the left hind leg of each animal at a dose of 0.1 mL to create an arthritis model. Paw volume was measured with a paw volume meter (PLETHYSMOMETER, Ugo Basile Model 7141). For evaluation of pain thresholds, a probe fitted to the sensor site of Pressure Application Measurement (PAM, Ugo Basile Model 38500) was used to turn the foot sole of a rat upward (dorsiflexion) until it gave an indication of pain or discomfort (vocalization) and the load being applied was measured. Eight days after the treatment with the adjuvant, the paw volume and pain threshold of each treated foot were measured and the animals were grouped for oral administration of each test compound (0.3 mg/kg) which was performed for nine days on a once-a-day schedule starting at day 9 and ending at day 17 after the treatment. At day 18 after the treatment, the paw volume and pain threshold of each untreated foot were measured.

The anti-inflammatory effect of the test compound was confirmed using the percent paw edema suppression as an indicator.

Percent paw edema suppression (%)=[(paw volume change in the control group−paw volume in each treatment group)/(paw volume change in the control group−paw volume change in the non-treatment group)]×100

As for the analgesic effect, the animals in the test compound group that had nociceptive thresholds greater than [(the mean nociceptive threshold of the control group)+2× standard deviation] were found "effective animals" and the percent effectiveness of each compound was calculated.

The results for the anti-inflammatory effect are given in Table 5 and that for the analgesic effect, in Table 6. The 4-alkynylimidazole derivatives of the present invention were verified to have an anti-inflammatory effect in view of their percent paw edema suppression, and an analgesic effect in view of their percent effectiveness.

TABLE 5

Anti-Inflammatory Effect on Adjuvant Induced Arthritis in Rats

| Compound No. | Percent paw edema suppression (%) |
| --- | --- |
| 1 | 54 |
| 2 | 21 |
| 10 | 82 |
| 21 | 53 |
| 22 | 90 |
| 42 | 88 |

(Values are means of 8~10 cases.)

TABLE 6

Analgesic Effect on Adjuvant Induced Arthritis in Rats

| Compound No. | Percent Effectiveness (%) |
| --- | --- |
| 1 | 30 |
| 2 | 38 |
| 10 | 78 |
| 21 | 20 |
| 22 | 60 |
| 42 | 90 |

(Values are means of 8~10 cases.)

Test Example 5

Test for Evaluating Analgesic Effect on Monoiodoacetic Acid Induced Joint Pain in Rats The animals were SD male rats (6 week-old). The right knee of each animal was treated intraarticularly with monoiodoacetic acid (MIA) to induce joint pain. Three days after the MIA treatment, a test compound (10 mg/kg) was administered orally and two hours later, the loads on the right and left hind legs were measured with an incapacitance tester (Linton). As it turned out, in the groups administered with Compounds 10, 22 and 42, the suppression of right knee joint pain was confirmed with the ratio between the loads on the right and left hind legs being taken as an indicator.

Consequently, it was also verified by Test Example 5 that the 4-alkynylimidazole derivatives of the present invention have a satisfactory analgesic effect.

INDUSTRIAL APPLICABILITY

The 4-alkynylimidazole derivatives (I) of the present invention have a superior EP4 receptor antagonistic action and are useful as pharmaceuticals specifically intended for the treatment of diseases associated with the EP4 receptor. For example, they are effective as anti-inflammatory and/or analgesic drugs for inflammatory diseases and diseases that involve various kinds of pains. In addition, they are also useful for the treatment of immune diseases that result from inflammations as evoked by tissue destruction due to the activation of Th1 cells and/or Th17 cells.

The invention claimed is:

1. A 4-alkynylimidazole derivative represented by the formula (I) or a pharmaceutically acceptable salt thereof:

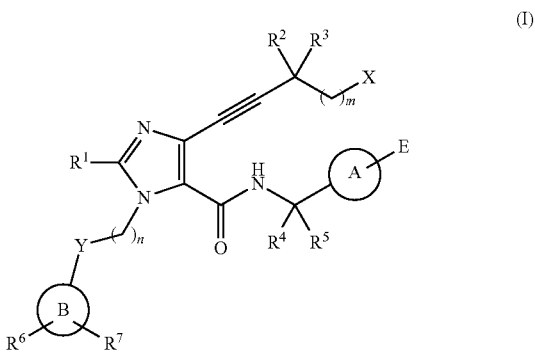

(I)

wherein ring A is an optionally substituted cycloalkyl, an optionally substituted aryl or an optionally substituted heteroaryl;
ring B is cycloalkyl, aryl or heteroaryl;
m is an integer of any one of 0~2;
n is an integer of any one of 1~3;
$R^1$ is a hydrogen atom, a $C_1$~$C_4$ alkyl group, a $C_1$~$C_4$ alkoxy group, a halogen atom, or a $C_1$~$C_4$ haloalkyl group;
$R^2$ and $R^3$ are each independently a hydrogen atom, a halogen atom or a $C_1$~$C_4$ alkyl group or may, taken together with the carbon atom to which $R^2$ and $R^3$ are adjacent, form a $C_3$~$C_6$ carbon ring;
$R^4$ and $R^5$ are each independently a hydrogen atom or a $C_1$~$C_4$ alkyl group or may, taken together with the carbon atom to which $R^4$ and $R^5$ are adjacent, form a $C_3$~$C_6$ carbon ring, and $R^6$ and $R^7$ are each independently a hydrogen atom, a $C_1$~$C_4$ alkyl group, a $C_1$~$C_4$ alkoxy group, a $C_1$~$C_4$ hydroxyalkyl group, a carboxyl group, a cyano group, a halogen atom, a $C_1$~$C_4$ haloalkyl group, or a $C_1$~$C_4$ haloalkoxy group;
X is —$OR^8$, —$NR^9R^{10}$ or a halogen atom;
$R^8$ is a hydrogen atom, a $C_1$~$C_4$ alkyl group or a $C_1$~$C_4$ haloalkyl group;
$R^9$ and $R^{10}$ are each independently a hydrogen atom or a $C_1$~$C_4$ alkyl group or may, taken together with the nitrogen atom to which $R^9$ and $R^{10}$ are adjacent, form a nitrogen-containing heterocycle, Y is a single bond, an oxygen atom or a sulfur atom; and
E is —$CO_2H$, —$CO_2P$ or bioisostere of a carboxyl group;
—$CO_2P$ is pharmaceutically acceptable ester prodrug.

2. The 4-alkynylimidazole derivative according to claim 1 or a pharmaceutically acceptable salt thereof, wherein in the foregoing formula (I), X is —$OR^8$ and m is 0.

3. The 4-alkynylimidazole derivative according to claim 1 or a pharmaceutically acceptable salt thereof, wherein in the foregoing formula (I), $R^2$ and $R^3$ are both a methyl group.

4. The 4-alkynylimidazole derivative according to claim 1 or a pharmaceutically acceptable salt thereof, wherein in the foregoing formula (I), $R^1$ is a methyl group, an ethyl group, a cyclopropyl group, a chlorine atom, a difluoromethyl group, or a trifluoromethyl group.

5. The 4-alkynylimidazole derivative according to claim 4 or a pharmaceutically acceptable salt thereof, wherein in the foregoing formula (I), $R^1$ is a chlorine atom.

6. The 4-alkynylimidazole derivative according to claim 1 or a pharmaceutically acceptable salt thereof, wherein in the foregoing formula (I), ring A is cyclohexyl substituted by E at the 4-position or phenyl substituted by E at the 4-position.

7. The 4-alkynylimidazole derivative according to claim 1 or a pharmaceutically acceptable salt thereof, wherein in the foregoing formula (I), E is —$CO_2H$ or tetrazolyl.

8. The 4-alkynylimidazole derivative according to claim 1 or a pharmaceutically acceptable salt thereof, wherein in the foregoing formula (I), ring B is phenyl, n is 1, and Y is a single bond.

9. The 4-alkynylimidazole derivative according to claim 8 or a pharmaceutically acceptable salt thereof, wherein in the foregoing formula (I), ring B is phenyl substituted by $R^6$ at the 4-position, $R^7$ is a hydrogen atom, and $R^6$ is any one of a $C_1$~$C_4$ alkyl group, a $C_1$~$C_4$ alkoxy group, a cyano group, a halogen atom, a $C_1$~$C_4$ haloalkyl group, and a $C_1$~$C_4$ haloalkoxy group.

10. The 4-alkynylimidazole derivative according to claim 1 or a pharmaceutically acceptable salt thereof, wherein the compound represented by the foregoing formula (I) is any one of:

[Formula 2]

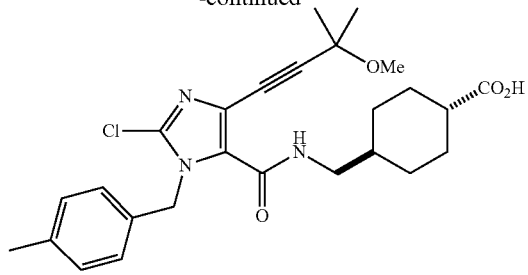

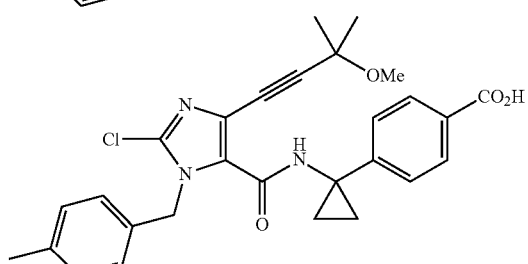

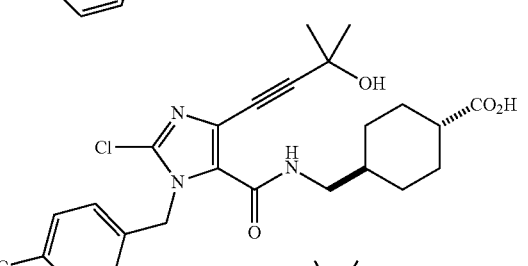

-continued

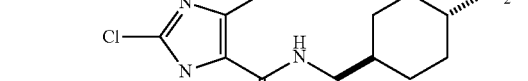

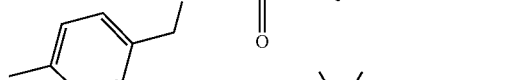

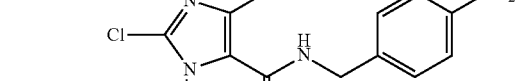

11. The 4-alkynylimidazole derivative according to claim 1 or a pharmaceutically acceptable salt thereof, wherein the compound represented by the foregoing formula (I) is:

12. A pharmaceutical composition comprising the 4-alkynylimidazole derivative according to claim 1 or a pharmaceutically acceptable salt thereof as an active ingredient and a pharmacologically acceptable carrier.

13. A method for antagonizing an EP4 receptor comprising administering to a subject in need thereof an effective amount of the 4-alkynylimidazole derivative according to claim 1 or a pharmaceutically acceptable salt thereof.

14. A method for treatment of a disease associated with an EP4 receptor-mediated action of PGE2 which is selected from the group consisting of arthritic pain, articular rheumatism, and osteoarthritis comprising administering to a subject in need of treatment an effective amount of the 4-alkynylimidazole derivative according to claim 1 or a pharmaceutically acceptable salt thereof.

15. The method according to claim 14, wherein the treatment is anti-inflammation and/or pain relieving.

* * * * *